(12) United States Patent
Faltys et al.

(10) Patent No.: US 12,290,695 B2
(45) Date of Patent: *May 6, 2025

(54) NEURAL STIMULATION DEVICES AND SYSTEMS FOR TREATMENT OF CHRONIC INFLAMMATION

(71) Applicant: SetPoint Medical Corporation, Valencia, CA (US)

(72) Inventors: Michael A. Faltys, Valencia, CA (US); Jesse M. Simon, Los Angeles, CA (US); Yiming Liu, Woburn, MA (US)

(73) Assignee: SetPoint Medical Corporation, Valencia, CA (US)

( * ) Notice: Subject to any disclaimer, the term of this patent is extended or adjusted under 35 U.S.C. 154(b) by 330 days.

This patent is subject to a terminal disclaimer.

(21) Appl. No.: 17/443,875

(22) Filed: Jul. 28, 2021

(65) Prior Publication Data

US 2021/0353949 A1    Nov. 18, 2021

Related U.S. Application Data

(60) Continuation of application No. 16/544,882, filed on Aug. 19, 2019, now Pat. No. 11,110,287, which is a (Continued)

(51) Int. Cl.
*A61N 1/36*     (2006.01)
*A61N 1/372*    (2006.01)
(Continued)

(52) U.S. Cl.
CPC ....... *A61N 1/3787* (2013.01); *A61N 1/36053* (2013.01); *A61N 1/3606* (2013.01);
(Continued)

(58) Field of Classification Search
CPC ................ A61N 1/3787; A61N 1/36053
(Continued)

(56) References Cited

U.S. PATENT DOCUMENTS 2,164,121 A   6/1939   Pescador
3,363,623 A   1/1968   Atwell
(Continued)

FOREIGN PATENT DOCUMENTS

CN    201230913 A   5/2009
CN    101528303 A   9/2009
(Continued)

OTHER PUBLICATIONS

US 6,184,239 B1, 02/2001, Puskas (withdrawn)
(Continued)

*Primary Examiner* — Nicole F Lavert
(74) *Attorney, Agent, or Firm* — Shay Glenn LLP

(57) ABSTRACT

A system for treating chronic inflammation may include an implantable microstimulator, a wearable charger, and optionally an external controller. The implantable microstimulator may be implemented as a leadless neurostimulator implantable in communication with a cervical region of a vagus nerve. The microstimulator can address several types of stimulation including regular dose delivery. The wearable charger may be worn around the subject's neck to rapidly (<10 minutes per week) charge an implanted microstimulator. The external controller may be configured as a prescription pad that controls the dosing and activity of the microstimulator.

22 Claims, 56 Drawing Sheets

Related U.S. Application Data continuation of application No. 16/005,191, filed on Jun. 11, 2018, now Pat. No. 10,384,068, which is a division of application No. 14/887,192, filed on Oct. 19, 2015, now Pat. No. 9,993,651, which is a continuation of application No. 14/508,940, filed on Oct. 7, 2014, now Pat. No. 9,162,064, which is a continuation of application No. 14/082,047, filed on Nov. 15, 2013, now Pat. No. 8,855,767, which is a division of application No. 12/978,250, filed on Dec. 23, 2010, now Pat. No. 8,612,002.

(60) Provisional application No. 61/306,849, filed on Feb. 22, 2010, provisional application No. 61/289,946, filed on Dec. 23, 2009.

(51) Int. Cl.
 *A61N 1/375* (2006.01)
 *A61N 1/378* (2006.01)
 *A61N 1/05* (2006.01)

(52) U.S. Cl.
 CPC ..... *A61N 1/36125* (2013.01); *A61N 1/36142* (2013.01); *A61N 1/37205* (2013.01); *A61N 1/37235* (2013.01); *A61N 1/375* (2013.01); *A61N 1/3756* (2013.01); *A61N 1/0556* (2013.01); *A61N 1/36175* (2013.01)

(58) Field of Classification Search
 USPC .......................................................... 607/60
 See application file for complete search history.

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,690,693 A | 11/1997 | Wang et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |

(56) References Cited

U.S. PATENT DOCUMENTS

| | | |
|---|---|---|
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 * | 5/2004 | Loeb et al. ............. A61N 1/39 607/41 |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,612,002 B2 | 12/2013 | Faltys et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |

(56) References Cited

U.S. PATENT DOCUMENTS

| | | |
|---|---|---|
| 9,403,001 B2 | 8/2016 | Simon et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075694 A1 | 4/2005 | Schmeling et al. |
| 2005/0075698 A1 | 4/2005 | Phillips et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |

(56) References Cited

U.S. PATENT DOCUMENTS

| | | |
|---|---|---|
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Paris et al. |
| 2007/0021814 A1 | 1/2007 | Inman et al. |
| 2007/0025608 A1 | 2/2007 | Armstrong |
| 2007/0027482 A1 | 2/2007 | Paris et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Enrico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234780 A1 | 9/2008 | Smith |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0131995 A1 | 5/2009 | Sloan et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Enrico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |

(56) References Cited

U.S. PATENT DOCUMENTS

| | | |
|---|---|---|
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0215632 A1 | 8/2010 | Boss et al. |
| 2010/0219796 A1 | 9/2010 | Kallmyer |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0042574 A1 | 2/2011 | Nishino et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0301658 A1 | 12/2011 | Yoo et al. |
| 2011/0301667 A1 | 12/2011 | Olson et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1 | 7/2012 | Kisker et al. |
| 2012/0185020 A1 | 7/2012 | Simon et al. |
| 2012/0296176 A1 | 11/2012 | Herbst |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0317580 A1 | 11/2013 | Simon et al. |
| 2014/0046407 A1 | 2/2014 | Ben-Ezra et al. |
| 2014/0213926 A1 | 7/2014 | Vaidyanathan |
| 2014/0371818 A1 | 12/2014 | Bond et al. |
| 2015/0233904 A1 | 8/2015 | Nayak |
| 2015/0241447 A1 | 8/2015 | Zitnik et al. |
| 2016/0114165 A1 | 4/2016 | Levine et al. |
| 2016/0250097 A9 | 9/2016 | Tracey et al. |
| 2016/0331952 A1 | 11/2016 | Faltys et al. |
| 2016/0367808 A9 | 12/2016 | Simon et al. |
| 2017/0202467 A1 | 7/2017 | Zitnik et al. |
| 2017/0245379 A1 | 8/2017 | Kang |
| 2018/0001096 A1 | 1/2018 | Faltys et al. |
| 2018/0117320 A1 | 5/2018 | Levine et al. |
| 2018/0289970 A1 | 10/2018 | Faltys et al. |
| 2019/0046799 A1 | 2/2019 | Levine et al. |
| 2019/0111263 A1 | 4/2019 | Levine et al. |
| 2019/0192847 A1 | 6/2019 | Faltys et al. |
| 2019/0275328 A1 | 9/2019 | Zitnik et al. |
| 2020/0094055 A1 | 3/2020 | Manogue |
| 2020/0206515 A1 | 7/2020 | Faltys et al. |
| 2020/0238078 A1 | 7/2020 | Faltys et al. |
| 2020/0330760 A1 | 10/2020 | Levine et al. |
| 2021/0251848 A1 | 8/2021 | Tracey et al. |
| 2022/0040483 A1 | 2/2022 | Levine et al. |
| 2022/0118257 A1 | 4/2022 | Huston et al. |
| 2022/0193413 A1 | 6/2022 | Levine et al. |
| 2022/0212001 A1 | 7/2022 | Faltys et al. |
| 2022/0212012 A1 | 7/2022 | Manogue |
| 2022/0362555 A1 | 11/2022 | Zitnik et al. |
| 2023/0019961 A1 | 1/2023 | Huston et al. |
| 2023/0117074 A1 | 4/2023 | Zanos et al. |
| 2023/0144580 A1 | 5/2023 | Manogue |
| 2023/0241387 A1 | 8/2023 | Levine et al. |
| 2023/0321445 A1 | 10/2023 | Zanos et al. |
| 2024/0215900 A1 | 7/2024 | Levine et al. |
| 2024/0299745 A1 | 9/2024 | Levine et al. |

FOREIGN PATENT DOCUMENTS

| | | | |
|---|---|---|---|
| CN | 101578067 A | 11/2009 | |
| CN | 101868280 A | 10/2010 | |
| DE | 2628045 A1 | 1/1977 | |
| DE | 3736664 A1 | 5/1989 | |
| DE | 20316509 U1 | 4/2004 | |
| EP | 0438510 B1 | 8/1996 | |
| EP | 0726791 B1 | 6/2000 | |
| EP | 1001827 B1 | 1/2004 | |
| EP | 2213330 A2 | 8/2010 | |
| EP | 2073896 B1 | 10/2011 | |
| GB | 04133 | 2/1910 | |
| GB | 2073428 A | 10/1981 | |
| KR | 20050039445 A | 4/2005 | |
| WO | WO93/01862 A1 | 2/1993 | |
| WO | WO97/30998 A1 | 8/1997 | |
| WO | WO98/20868 A1 | 5/1998 | |
| WO | WO00/27381 A2 | 5/2000 | |
| WO | WO00/47104 A2 | 8/2000 | |
| WO | WO01/00273 A1 | 1/2001 | |
| WO | WO01/08617 A1 | 2/2001 | |
| WO | WO01/89526 A1 | 11/2001 | |
| WO | WO02/44176 A1 | 6/2002 | |
| WO | WO02/057275 A1 | 7/2002 | |
| WO | WO03/072135 A2 | 9/2003 | |
| WO | WO2004/000413 A2 | 12/2003 | |
| WO | WO2004/064918 A1 | 8/2004 | |
| WO | WO2006/073484 A1 | 7/2006 | |
| WO | WO2006/076681 A2 | 7/2006 | |
| WO | WO-2007059343 A2 * | 5/2007 | ............. A61N 1/375 |
| WO | WO2007/133718 A2 | 11/2007 | |
| WO | WO2010/005482 A1 | 1/2010 | |
| WO | WO2010/067360 A2 | 6/2010 | |
| WO | WO2010/118035 A2 | 10/2010 | |
| WO | WO2016/134197 A1 | 8/2016 | |

OTHER PUBLICATIONS

De Jonge et al.; Stimulation of the vagus nerve attenuates macrophage activation by activating the Jak2-STAT3 signaling pathway; Nature Immunology; 6(8); pp. 844-851; Aug. 2005.

Levine et al.; U.S. Appl. No. 17/728,765 entitled "Systems and methods for stimulating and/or monitoring loci in the brain to treat inflammation and to enhance vagus nerve stimulation," filed Apr. 25, 2022.

Faltys et al.; U.S. Appl. No. 17/751,505 entitled "Implantable neurostimulator having power control and thermal regulation and methods of use," filed May 23, 2022.

Levine et al.; U.S. Appl. No. 18/151,407 entitled "Control of vagal stimulation," filed Jan. 6, 2023.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al., "On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

(56) References Cited

OTHER PUBLICATIONS

Benoist, et al., "Mast cells in autoimmune disease" Nature., vol. 420(19): pp. 875-878, Dec. 2002.
Benthem et al.; Parasympathetic inhibition of sympathetic neural activity to the pancreas; Am.J.Physiol Endocrinol.Metab; 280(2); pp. E378-E381; Feb. 2001.
Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.
Bernik et al., Vagus nerve stimulation attenuates endotoxic shock and cardiac TNF production, 87th Clinical Congress of the American College of Surgeons, New Orleans, LA, Oct. 9, 2001.
Bernik et al., Vagus nerve stimulation attenuates LPS-induced cardiac TNF production and myocardial depression IN shock, New York Surgical Society, New York, NY, Apr. 11, 2001.
Bernik, et al., Pharmacological stimulation of the cholinergic anti-inflammatory pathway, The Journal of Experimental Medicine, vol. 195, No. 6, pp. 781-788, Mar. 18, 2002.
Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. Vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Biggio et al.; Chronic vagus nerve stimulation induces neuronal plasticity in the rat hippocampus; Int. J. Neurpsychopharmacol.; vol. 12; No. 9; pp. 1209-1221; Oct. 2009.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135 (2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioligal aspects and therapeutic approaches, abstacts and program, Fourth international Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, Thieme Medical Publishers; pp. 189-204, © 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al.; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.
Corcoran, et al., The effects of vagus nerve stimulation on pro- and anti-inflammatory cytokines in humans: a preliminary report, NeuroimmunoModulation, vol. 12(5), pp. 307-309, Sep. 2005.
DAS, Critical advances in spticemia and septic shock, Critical Care, vol. 4, pp. 290-296, Sep. 7, 2000.
Del Signore et al.; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.

(56) References Cited

OTHER PUBLICATIONS

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.

Goyal et al., Nature of the vagal inhibitory innervation to the lower esophageal sphincter, Journal of Clinical Investigation, vol. 55, pp. 1119-1126, May 1975.

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzas infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass" Journal of Thoracic and Cardiovascular Surgery, Mosby-Year Book, inc., St. Louis, MO, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;, vol. 13; No. 2; pp. 93-122; Apr.-Jun. 1982.

Kanai, T. et al., Interleukin-18 and Crohn's disease, Digestion, vol. 63, suppl. 1, pp. 37-42, (year of pub, sufficiently earlier than effective US filing date and any foreign priority date) 2001.

Katagiri, M., et al., Increased cytokine production by gastric mucosa in patients with helicobacter pylori infection, J. Clin, Gastroenterol., vol. 25, Suppl. 1, pp. S211-S214, 1997.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kawashima, et al., Extraneuronal cholinergic system in lymphocytes, Pharmacology & Therapeutics, vol. 86, pp. 29-48, Apr. 2000.

Kees et al; via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from

(56) References Cited

OTHER PUBLICATIONS the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85, (year of pub. sufficiently earlier than effective US filing date and any foreign priority date) 1973.
Kuznik, et al., "Blood Coagulation in stimulation of the vagus nerve in cats," Biull. Eskp. Biol. Med., vol. 78 (7): pp. 7-9, (year of pub. sufficiently earlier than effective US filing date and any foreign priority date) 1974.
Kuznik, et al., "Heart as an efferent regulator of the process of blood coagulation and fibrinolysis," Kardiologiia. vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologila, vol. 13(4): pp. 145-154, Apr. 1973.
Kuznik, et al., "Secretion of blood coagulation factors into saliva under conditions of hypo-and hypercoagulation," Voprosy Meditsinskol Khimii, vol. 19(1): pp. 54-57; (year of pub. sufficiently earlier than effective US filing date and any foreign priority date) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin Exp. Immunol., vol. 100, pp. 139-144, Apr. 1995.
LeNovere, N. et al., Molecular evolution of the nicotinic acetylcholine receptor: an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.
Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibrinolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al., "Treatment of Botkin's disease with heparin," Klin. Med., vol. 51(3): pp. 113-117, Mar. 1973.
Pavlov et al; Controlling inflammation: the cholinergic anti-inflammatory pathway; Biochem. Soc. Trans.; 34(Pt 6); pp. 1037-1040; Dec. 2006.
Pavlov et al.; The cholinergic anti-inflammatory pathway; Brain, Behavior, and Immunity; 19; p. 493-499; Nov. 2005.
Palov et al.; The cholinergic anti-inflammatory pathway: a missing link in neuroimmunomodulation; Molecular Medicine; 9(5); pp. 125-134; May 2003.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.

(56) References Cited

OTHER PUBLICATIONS

Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiogram the Action of the Vagus Nerve on the Human Heart; J Exp Med; 14(3):217-234; Sep. 1911.
Romanovsky, A. A., et al., The vagus nerve in the thermoregulatory response to systemic inflammation, Am. J. Physiol., vol. 273, No. 1 (part 2), pp. R407-R413, Jul. 1, 1997.
Saghizadeh et al., The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.
Suter et al.; Do glial cells control pain ?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparison between chinese blended medicine "Shosefryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J. et al., Shock and tissue injury induced by recombinant human cachectin, Science, vol. 234, pp. 470-474, Oct. 24, 1986.
Tracey, K. J.; Reflex control of immunity; Nat Rev Immunol; 9(6); pp. 418-428; Jun. 2009.
Tracey, K.J., The inflammatory reflex, Nature, vol. 420, pp. 853-859, Dec. 19-26, 2002.
Tsutsui, H., et al., Pathophysiologi inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Der Horst et al.; Stressing the role of FoxO proteins in lifespan and disease; Nat Rev Mol Cell Biol.; vol. 8; No. 6; pp. 440-450; Jun. 2007.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.

(56) References Cited

OTHER PUBLICATIONS

Ventureyra, Transcutaneous vagus nerve stimulation for partial onset seizure therapy, Child's Nerv Syst, vol. 16(2), pp. 101-102, Feb. 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetylase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Zamotrinsky et al.; Vagal neurostimulation in patients with coronary artery disease; Auton. Neurosci., 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhang et al.; Roles of SIRT1 in the acute and restorative phases following induction of inflammation.; J Biol Chem.; vol. 285; No. 53; pp. 41391-41401; Dec. 2010.
Levine et al.; U.S. Appl. No. 17/337,292 entitled "Closed-loop vagus nerve stimulation," filed Jun. 2, 2021.
Huston et al.; U.S. Appl. No. 18/355,401 entitled "Methods for reducing bleeding in hemophilia by vagus nerve stimualtion to prime platelets," filed Jul. 19, 2023.
Gautron et al.; Neurobiology of inflammation-associated anorexia; Frontiers in Neuroscience; 3(59); 10 pages; Jan. 8, 2010.
Li et al.; U.S. Appl. No. 18/645,129 entitled "System and methods of stimulation at trigeminaly innervated regions for disorders of cerebral perfusion," filed Apr. 24, 2024.
Levine et al.; U.S. Appl. No. 18/730,753 entitled "Treatment of inflammatory disorders," filed Jul. 19, 2024.
Hebb et al.; Creating the Feedback Loop: Closed-Loop Neurostimulation; Neurosurgery Clinics of North America; 25(1); pp. 187-204; Jan. 28, 2014.
Calle et al.; U.S. Appl. No. 18/562,283 entitled "Neurostimulation parameter authentication and expiration system for nuerostimulation," filed Nov. 17, 2023.
Levine et al.; U.S. Appl. No. 18/431,974 entitled "Vagus nerve stimulation pre-screening test," filed Feb. 3, 2024.
Zitnik et al.; U.S. Appl. No. 18/604,465 entitled "Batteryless implantable microsimulators," filed Mar. 13, 2024.
Levine; U.S. Appl. No. 18/605,809 entitled "Bimodal vagus nerve simulation to treat neurodegenerative disorders," filed Mar. 14, 2024.

* cited by examiner

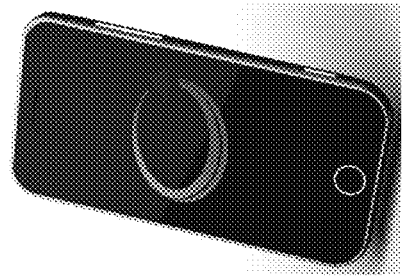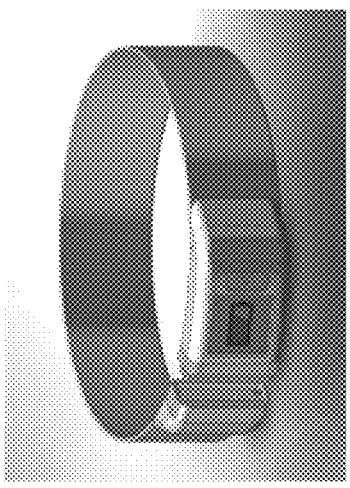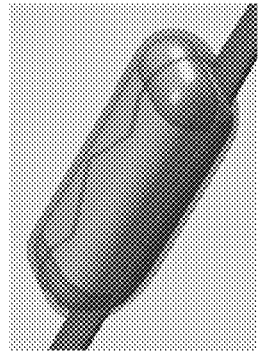
FIG. 1B

FIG. 1D
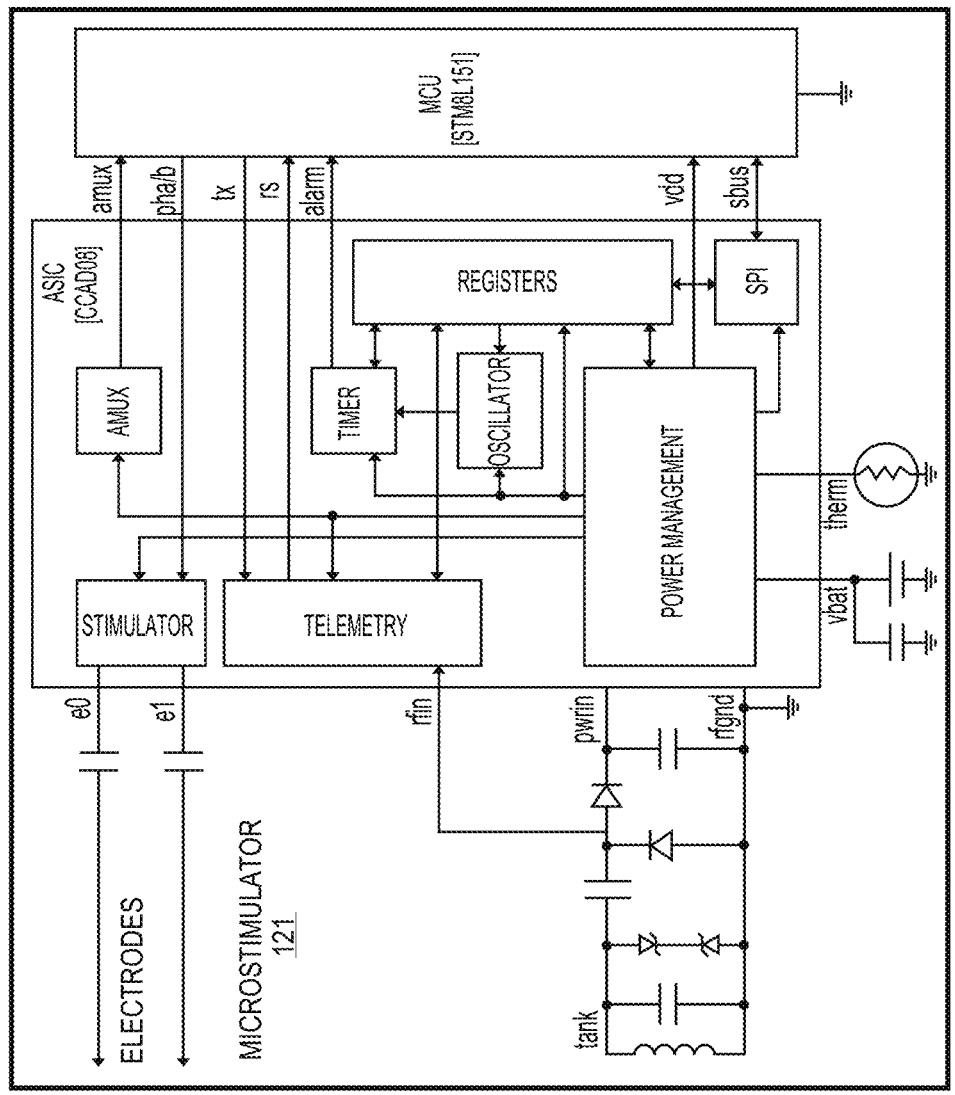
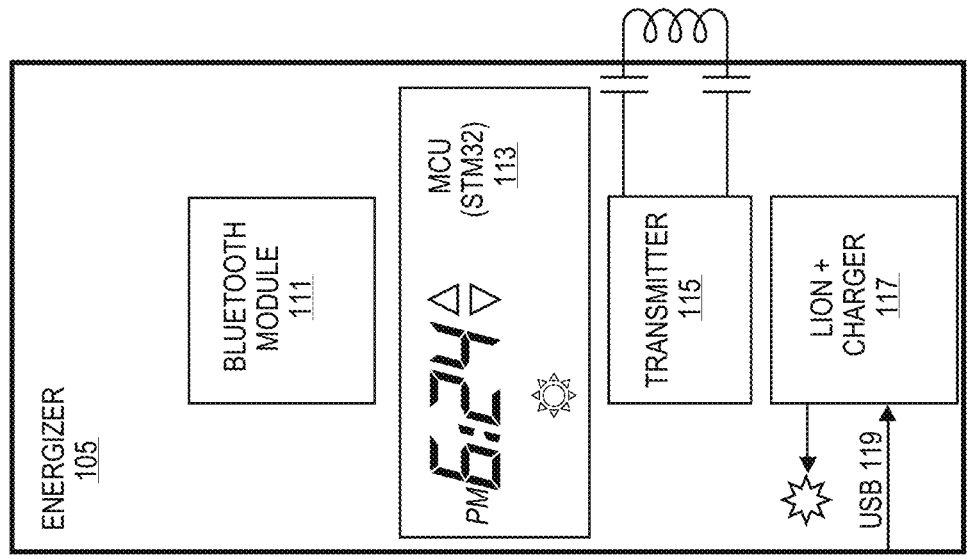

FIG. 5A
FIG. 5B
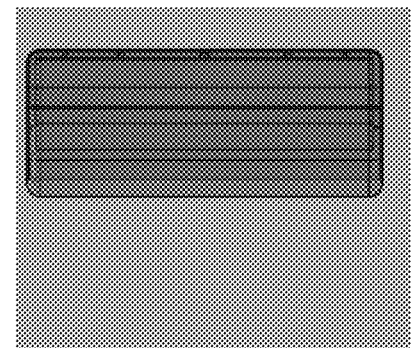
FIG. 5C
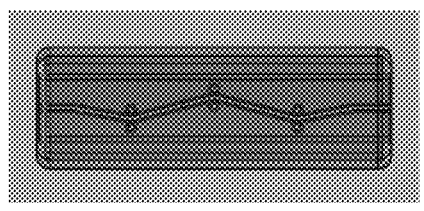
FIG. 5D

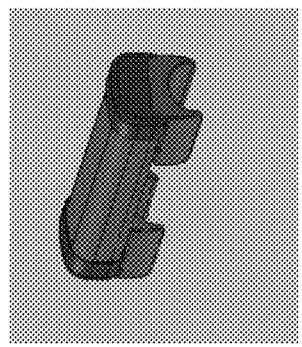
FIG. 6A
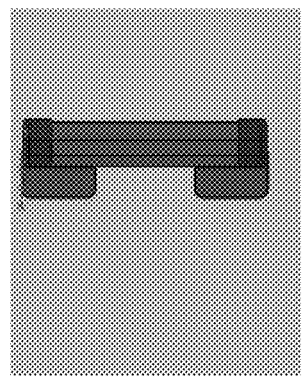
FIG. 6B
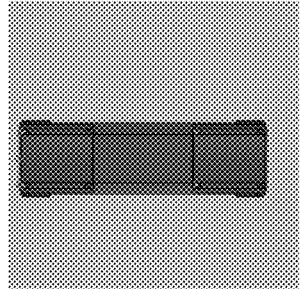
FIG. 6C
FIG. 6D

NEURAL STIMULATION DEVICES AND SYSTEMS FOR TREATMENT OF CHRONIC INFLAMMATION

CROSS REFERENCE TO RELATED APPLICATIONS

This patent application is a continuation of U.S. patent application Ser. No. 16/544,882, filed on Aug. 19, 2019, titled "NEURAL STIMULATION DEVICES AND SYSTEMS FOR TREATMENT OF CHRONIC INFLAMMATION," now U.S. Patent Publication No. US-2020-0324125-A1, which is a continuation of U.S. patent application Ser. No. 16/005,191, filed on Jun. 11, 2018, titled "NEURAL STIMULATION DEVICES AND SYSTEMS FOR TREATMENT OF CHRONIC INFLAMMATION," now U.S. Pat. No. 10,384,068, which is a divisional application of U.S. patent application Ser. No. 14/887,192, titled "NEURAL STIMULATION DEVICES AND SYSTEMS FOR TREATMENT OF CHRONIC INFLAMMATION," filed on Oct. 19, 2015, now U.S. Pat. No. 9,993,651, which is a continuation of U.S. patent application Ser. No. 14/508,940, titled "NEURAL STIMULATION DEVICES AND SYSTEMS FOR TREATMENT OF CHRONIC INFLAMMATION," filed on Oct. 7, 2014, now U.S. Pat. No. 9,162,064, which is a continuation of U.S. patent application Ser. No. 14/082,047, titled "NEURAL STIMULATION DEVICES AND SYSTEMS FOR TREATMENT OF CHRONIC INFLAMMATION," filed on Nov. 15, 2013, now U.S. Pat. No. 8,855,767, which is a divisional of U.S. patent application Ser. No. 12/978,250, titled "NEURAL STIMULATION DEVICES AND SYSTEMS FOR TREATMENT OF CHRONIC INFLAMMATION," filed on Dec. 23, 2010, now U.S. Pat. No. 8,612,002, which claims priority to U.S. Provisional Patent Application Nos. 61/289,946, titled "LEADLESS CUFF MICROSTIMULATOR STIMULATOR," filed on Dec. 23, 2009; and 61/306,849, titled "NEURAL STIMULATION DEVICES AND SYSTEMS FOR TREATMENT OF CHRONIC INFLAMMATION," filed on Feb. 22, 2010, each of which is herein incorporated by reference in their entirety.

This patent application may also be related to abandoned U.S. patent application Ser. No. 12/874,171, titled "PRESCRIPTION PAD FOR TREATMENT OF INFLAMMATORY DISORDERS" and U.S. patent application Ser. No. 12/797,452, titled "NERVE CUFF WITH POCKET FOR LEADLESS STIMULATOR," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to systems and devices for treatment of chronic inflammation. In particular, described herein are systems including an implantable microstimulators adapted for electrically stimulating one or more nerves (e.g., the vagus nerve) to treat chronic inflammation by modulation of the inflammatory response (via the nicotinic cholinergic anti-inflammatory pathway); a charging/programming device for communicating with the implanted microstimulator; and a controller (which may be integrated with or separate from the charging/programming device, for controlling the activity of the microstimulator and other system components as described below.

BACKGROUND

Implantable electrical stimulation devices have been developed for therapeutic treatment of a wide variety of diseases and disorders. For example, implantable cardioverter defibrillators (ICDs) have been used in the treatment of various cardiac conditions. Spinal cord stimulators (SCS), or dorsal column stimulators (DCS), have been used in the treatment of chronic pain disorders including failed back syndrome, complex regional pain syndrome, and peripheral neuropathy. Peripheral nerve stimulation (PNS) systems have been used in the treatment of chronic pain syndromes and other diseases and disorders. Functional electrical stimulation (FES) systems have been used to restore some functionality to otherwise paralyzed extremities in spinal cord injury patients.

Typical implantable electrical stimulation systems may include one or more programmable electrodes on a lead that are connected to an implantable pulse generator (IPG) that contains a power source and stimulation circuitry. However, these systems can be difficult and/or time consuming to implant, as the electrodes and the IPG are usually implanted in separate areas and therefore the lead must be tunneled through body tissue to connect the IPG to the electrodes. Also, leads are susceptible to mechanical damage over time, particularly as they are usually thin and long.

Recently, small implantable neural stimulator technology, i.e. microstimulators, having integral electrodes attached to the body of a stimulator has been developed to address the disadvantages described above. This technology allows the typical IPG, lead and electrodes described above to be replaced with a single integral device. Integration of the lead has several advantages including reduction of surgery time by eliminating, for example, the need for implanting the electrodes and IPG in separate places, the need for a device pocket, the need for tunneling to the electrode site, and requirements for strain relief ties on the lead itself. Reliability may therefore be increased significantly, especially in soft tissue and across joints because active components, such as lead wires, are now part of the rigid structure and are not subject to the mechanical damage due to repeated bending or flexing over time.

Unfortunately, the currently developed leadless devices tend to be larger and more massive than desirable, and even than traditional electrode/lead assemblies, making it difficult to stably position such devices in the proper position with respect to the nerve. Without device stability, the nerve and/or surrounding muscle or tissue can be damaged due to movement of the assembly. Further these devices require long charging times, and are often difficult to control (e.g., program) and regulate.

There remains a need for a leadless integral device that is stably positioned on the nerve, and can provide for removal and/or replacement of the stimulation device with relative ease.

In addition, prior art microstimulators have typically been designed to be injectable. Injectable stimulators rely not only on the accuracy of positioning, but the resulting arbitrary flows of current due to the in-situ heterogeneous tissues hosting the device. Current flows induced by non-shielded electrodes will vary in most situations with movements (e.g. neck movement, etc.) making control of the relationship with the target (and therefore reliable stimulation of the target) all but impossible. In situations where the target thresholds are extremely low and the thresholds to invoke undesirable side effects are very high, an unshielded electrode from an injectable stimulator may be acceptable. However, for most situations, the target neuron is surrounded by tissues that are susceptible to unintended stimulation. While convenient to implant, these unshielded microstimulators are unacceptable for most applications. By containing the microstimulator in an isolated space with the nerve, the therapy window may be greatly increased.

Neurostimulator applications to this point have also been constrained to pulse generating applications where a constant pulse train is presented to the neural tissue. This pulse train may be gated or modulated to evoke the desired response and transfer the appropriate information to the target tissues. In other applications, such as FES, stimulation is presented to actuate muscles on demand. However, a neurostimulator may be used in an entirely new paradigm that is more like a pharmaceutical or biologic agent, where a dose is presented and a pharmacokinetic or pharmacodynamic response is elicited. This type of neural stimulation may result in a drug-like response delivered through a prescription written (e.g., "programmed") by the administering physician. Delivering this type of stimulus typically requires short durations of stimulus followed by long durations of off-time, again typically administered in synchrony with the human circadian rhythm. Synchronizing such requires a sufficiently accurate real-time clock that initiates delivery of a stimulation dose.

Described herein are microstimulators and methods of using them that may address some of the needs identified above.

SUMMARY OF THE DISCLOSURE

Described herein are systems for the treatment of chronic inflammatory disorders that include an implantable microstimulator and an external charger/controller; in some variations a separate controller (e.g., "prescription pad") may also be included as part of the system.

In some variation, the microstimulator may include two (or more) parts that may assemble in-situ, in the operating room, or during the manufacturing process. The microstimulator (or "microstimulator system") may include a nerve cuff with or without integral electrodes, which may be called a POD ("Protection and Orientation Device," e.g., see FIGS. 5A-D and U.S. patent application Ser. No. 12/797,452, titled "NERVE CUFF WITH POCKET FOR LEADLESS STIMULATOR," now U.S. Pat. No. 8,886,339, previously incorporated by reference) that may enclose a portion of the neural tissue, and a microstimulator. The microstimulator (e.g., FIG. 4) generally includes integral contacts that make contact with the neural tissue, and if used in conjunction with a POD, may also make contact with the integral contacts within the POD.

The POD cuff electrode configuration of the stimulation device may allow the device to be stably positioned proximate a nerve, such as the vagus nerve. Furthermore, the cuff electrode configuration may also have the characteristics of driving most of the current into the nerve, while shielding surrounding tissues from unwanted stimulation.

In some embodiments, the nerve cuff generally includes a polymer cuff body or carrier, such as Silastic® cuff or sleeve, having a pocket or pouch defined therein for irremovably receiving a leadless stimulation device. The leadless stimulation device is positioned within the pocket or sleeve such that the electrodes of the device are positioned proximate the nerve to be stimulated and in alignment with integral contacts. The pocket can be defined by the space between the stimulation device and an inner surface of the cuff body or can comprise a pouch-like structure attached to the cuff body for containing the stimulation device. The nerve cuff can configured to be coupled to the nerve, or to a surrounding sheath that contains the nerve, or to both, depending on the desired level of stability.

The nerve cuff can be implanted by first dissecting the nerve to which it is to be connected, such as the vagus nerve, from its surrounding sheath, wrapping the nerve cuff around the nerve, optionally coupling or suturing the nerve cuff to one of either the nerve or the sheath and inserting the stimulation device within the pocket or pouch of the cuff body such that the stimulation device is proximate the nerve, or allowing the whole cuff and stimulation device to float along the axis of the nerve allowing fibrous encapsulate the device and eliminate or reduce movement of the device up and down along the nerve, and rotating around the neural axis.

The POD may be constructed with a biocompatible and durable polymer (FIGS. 5A-D). It is designed to be thin as possible to minimize displacement of nearby tissues to not be excessively more than the microstimulator itself. Other design goals include smooth and gradual transitions between surfaces to avoid anatomical damage or irritation. Support to easily allow replacement of the microstimulator; this can be enabled through top access over the nerve and securing device in the POD by sutures. Suture holes may be implemented to guide the surgeon, and embedded Dacron may be used to reinforce those openings. Mechanically (interlocking) and visually keyed (colored stripes) may be used so that when sutured shut, deformation or misalignment will not occur. Design should be such that over-tightening sutures do not compress the nerve leading to de-vascularization and eventual nerve death. In this embodiment, this is achieved by creating a rigid or semi-rigid nerve channel in the microstimulator itself. Nerve diameters of 2-4 mm from round to oval shapes require support; an oval shape is preferred in this implementation. The contacts should be protected from fibrous in growth via the POD as well as shielding non-target tissues. A polymeric material is choosing to further protect the surround the rigid MEB from soft tissue. The POD maintains co-axial alignment with the target nerve. The POD design is such that the POD may move up and down on nerve and may rotate around the nerve, and as mentioned earlier this is compensated through the use of non-coplanar antennae.

The POD may contain integral electrodes. This provides the opportunity to completely encircle the nerve. A platinum alloy may be embedded in the POD polymer. Since there can be significant flexing do to artery flexing or voluntary patient movements integrated contact ends must not be allowed to extrude from the polymer. A sharp metal object could seriously harm the patient. This possibility is avoided by integrating the electrode ends into the suture holes, so even of the polymer degrades the metal braids forming the contacts will not come loose.

The microstimulator (FIG. 4) itself may contain many innovations, in one embodiment it is composed of a ceramic such as Alumina/Zirconia® tube with biocompatible metal fittings such as Titanium/Niobium that are brazed to the ends of the ceramic tube (FIG. 7). These fittings receive metal lids that are laser welded creating a hermetic space inside the ceramic tube. The ceramic tube may contain one or more Nobel gases and the electronic hybrid (FIG. 8) in addition to a moisture absorbent material (e.g., "Getter") to absorb additional moisture for the purposes of hermetic leak testing and absorption of any moisture that may penetrate the hermetic barrier. The electronic assembly may make contact two the two end caps in one implementation by having gold plated spring contacts that press against the gold plated lids with sufficient to maintain contact even highly vibratory environments.

On the outside of the microstimulator the end caps may make electrical contact with either the nerve, or the integral POD electrodes, or both. In another embodiment electrodes may be welded to the end caps and these electrodes will make contact with either the nerve, or integral POD electrodes, or both.

The electronic assembly consists of a substrate (FIGS. 10 and 11), one or more antennae for receiving power, and sending and receiving power to and from outside charging and programming device, replenish able power source, and an electronic circuit than may autonomously stimulate the neural tissue.

In some variations, the substrate may be constructed from ceramic with palladium conductors laid down in a thick film process. Circuits are soldered or attached with conductive epoxy to the traces and in addition the battery, antennae, and spring contacts are fixated to the substrate.

Antennae may consist of any assembly that can receive power from the external electric field. These antennae have certain characteristics such a resonant frequency and a quality factor (Q). One implementation of such an antenna is a coil of wire with or without a ferrite core with to form an inductor with a defined inductance (FIGS. 8 and 9). This inductor may be coupled with a resonating capacitor and a resistive loss to form the resonant circuit. The frequency may be set to that of the radiated electric field to receive power and data from the external source. Data is transmitted back to the source by dynamically loading the resonant circuit with real or complex impedance. This can create a change in the load perceived by the external driver of the electrical field allowing data to be received from the implant. Another embodiment of antennae is a piezoelectric or magneto resistive element. The antenna may also be sized properly to receive sufficient power to charge the replenishable power source. In the case of planer antennas, multi-planer antennas can be implemented in the implant and/or externally in order to make the device tolerant to axial rotation (FIG. 9). For instance two antennae that are rotated 30 degrees) (30°) from one another will not achieve the coupling of two antennae on one plane but will maintain a degree of efficiency from any direction.

Electrical contact to the end caps may be made through spring contacts from a material such as beryllium copper and gold plated. In combination with gold plated end caps, this may form an extremely reliable connection and isolate the internal hybrid from mechanical and thermal shock. The static tension must be low enough not to warp the hybrid board over the life of the device, making implementation from a non-amorphous material essential. Another embodiment would be to insert the hybrid in a plastic carrier, and resistance weld connection wires from the end caps to the substrate before the end caps are welded shut.

That replenishable power source can be a battery, capacitor, and a hybrid battery capacitor device with sufficient capacity to power the implant for extended periods of operation. The power source may be rechargeable a number of times sufficiently to support the life of the device. In one implementation, a battery made from a lithium solid-state material will be used. This material results in a simple charger circuit that consists of a current limited voltage source that is applied in the presence of the externally generated electromagnetic field. All these battery technologies may be protected by an under voltage cutoff circuit that completely shuts down device current thus preventing the irreversible chemical changes that occur when a battery is discharged below its minimum voltage. Another characteristic of the power source that may be important is very low leakage or long "shelf-life". Depending on the battery technology it may be important to record that a battery has migrated to a voltage below its minimum voltage at which point that the battery should not be charged. This is enabled by measuring the voltage as soon as power is received on the antenna and shutting off battery charging, thus resulting in a system that can communicate with the external system and cannot be used to autonomously stimulate that patient.

The electrical circuits may consist of a power source charger with protection circuits, a state machine to control the device, an internal clock, stimulation current sources, protection from an overly intense electromagnetic field such as encountered by an over powered transmitter or the dynamic component of a MRI system, protection of external current generators such as those produced by monopolar electro-cautery, finally demodulation and modulation circuits for receiving and transmitting data, voltage measurement circuits for monitoring the system and the physiologic/electrode interface (FIGS. 12 and 13).

In one embodiment all the above circuits are implemented with an integrated circuit, along with discrete, in another embodiment it would consist of an integrated circuit, discrete components and a separate microcontroller that would contain read/write non-volatile memory for containing firmware, patient parameters, and required system state. The microcontroller may contain other functionality such as analog to digital converters for voltage measurement and digital to analog converters for driving the stimulus current sources.

Stimulus dosing may benefit from the use of a fairly accurate clock that generates with the time between stimuli, or ticks for a real-time clock that implements potentially far more complex dosage scenarios. Accurate clocks are typically implemented using piezoelectric crystals but these crystals can be large, expensive, and prone to damage. An alternate embodiment involves using a semiconductor junction to generate a reference voltage that in turn charges an RC circuit to produce a time reference. Typically these voltage references have significant variations due to integrated circuit parameters and temperature variations. The implant is in a temperature stable environment eliminating the need for temperature compensation. The wafer to wafer and die to die variations can be calibrated at a fixed temperature and scaled to 37 degrees centigrade during manufacturing or can be calibrated during the programming or charging process. The preferred implementation is to have an accurate time source in the charger, command the implant to produce a specific number of ticks before sending a message back to the charger. Then the charger would provide to the implant the actual duration of a tick. Still not being particular accurate over the period of, for example a year, whenever the charge is connected it can correct implant time. This model also allows the patient to move to different time zones without modifying potentially salient circadian component of the stimulation.

Power may be extracted from an antenna in the resonant circuit by rectifying using SiGe or appropriately fast low loss diodes, limiting the peak voltage with a zener diode to the maximum voltage that can be tolerated by the integrated circuit and capacitor, and then filtered by a capacitor. Data is transmitted back to the charger/programmer by either changing the Q of the resonant antenna circuit directly by loading the circuit dynamically.

Telemetry data is encoded on the envelope of the carrier. The carrier may be used as a clock source for the implant to decode the data. The envelope may be extracted by a non-linear element (e.g. diode) and then filtered to remove the carrier with a low pass filter that has a cutoff frequency between the bit rate and carrier frequency. This envelope signal may then be sliced by the long or short term average value to produce binary data and then is decoded.

Back telemetry data may be extracted from the charging antenna by dividing down the incoming differential voltage from the resonant circuit and demodulating. Demodulation may be performed by extracting the envelope by a non-linear element (e.g. diode) and then filtered to remove the carrier with a low pass filter that has a cutoff frequency between the bit rate and carrier frequency. This envelope signal may then be sliced by the long or short term average value to produce binary data and then is decoded.

The output of the slicer is routed to an asynchronous serial port that has an approximation of the bit clock generated by a laser trimmed and calibrated oscillator.

The external system that provides charging and programming of the system consists of a coil that generates an electromagnetic field of sufficient strength to penetrate through the patient's body to the location of the implanted device (FIG. 1). Data is communicated to the implant by modulating the amplitude of the carrier. Other implementations are possible where the carrier frequency or phase is modulated. Data is received by detecting minute changes caused by load shift keying implemented in the implant and demodulating the resultant signal. The coil is controlled by a microcontroller in the handheld or worn (e.g., on the neck) charger that is responsible for charging, programming, and checking device status. The charging/programmer may be further linked using a wired or wireless link to a prescription pad implemented on a mobile computing device. The prescription function may be implemented in an LCD screen of the charging device (FIG. 2).

The coil is part of a tuned resonant circuit set to a specific frequency, or allows shifting frequency to optimize the coupling coefficient between the external coil and the implant antenna. In the case of a fixed frequency it will be set to an allocated frequency band such as the International Scientific and Medical Band (125 KHz, 6.78 MHz, 13.56 MHz, or 27 MHz). In order to effectively transmit power and stay with allocated frequency bands the Q of the coil may be rather high. A class-E transmitter (FIG. 17) or Class-D (FIG. 19) is well suited to drive the coil since it has low parts count and has a very high efficiency. Since the coil is not perfect device and it is high sensitive the dielectric constant of the surround media many compensations must be made. First the coil may require shielding using a conductive media in close proximity to the coil wires, an electrically closed loop cannot be formed or the transmitting coil will be shorted out. Secondly as the transmitting coil is moved towards the skin and implant the dielectric constant will dramatically shift, this shift will cause a shift in the resonant frequency of the system. Two methods exist to 're-tune" the circuit: one is to shift the driving frequency along with the coil, this requires the implant to be part of the circuit, and the second method is to have a method to "re-tune" the circuit. This is a more practical approach in the case that the coupling coefficient is less than 2%, which is the typical case for a small and deeply implanted Microstimulator. The circuit may be dynamically tuned to maximize power transfer, and/or to minimize side-lobe radiation outside the allocated frequency band. Dynamically tuning the loop is typically achieved by using a variable inductor embedded in a PID controller (FIG. 18) optimized to maximize power transfer or minimize side lobe radiation. The voltages induced across this coil may be in the hundreds of volts, and currents can approach an ampere. The variable inductance technique is implemented by inducing a static flux into a series tuning inductor modifying the inductance. This is achieved by winding a primary and secondary on a ferromagnetic core and inducing a DC current through the secondary modifying the effective permittivity of the core shifting the primary inductance. In an embodiment the back telemetry modulation depth on the transmitting coil or power derived to the microstimulator would be measured in the receiving coil and a PID controller would adjust the inductance in the second coil.

Coil power to transmit data can either be shifted by modulating the modulating the 'collector' voltage or by gating the carrier on and off to the class-d power amplifier or both. One implementation is to digitally generate the carrier frequency using a phase accumulator (FIG. 39) oscillator that allows precise carrier frequency adjustment to aid in tuning the system to maximum the coupling coefficient.

Microstimulator electrode contacts may be designed to loosely couple to the nerve as not to constrict and thus damage the nerve, but to maintain as much nerve contact as possible. They should be constricted of an accepted physiologic electrode material such as a platinum iridium alloy. A rigid or semi-rigid structure allows the POD to be tightened without the possibility of compressing the nerve. In a rigid structure, several sizes may be made available to accommodate the sizes of nerves available (FIGS. 3A-3B). A semi-rigid structure allows the contacts to be bent to size. Different POD sizes are likely required to accommodate the rigid and semi-rigid structures. Flares and radii may be used to assure that the nerve will not be cut or scraped.

For example, described herein are systems for treating chronic inflammation in a patient. Such a system may include: an implantable microstimulator configured for implantation around a cervical portion of a vagus nerve to modulate inflammation by applying a low duty-cycle stimulation; a charger configured to be worn around the patient's neck and to charge the implantable micro stimulator; and an external controller configured to set a dose amplitude and dose interval for the microstimulator.

In some variations, the system also includes a POD for securing the microstimulator within the patient. The system may also be configured to charge the implantable microstimulator for less than about 10 minutes per week, 20 minutes per week, 30 minutes per week, etc.

In general, these systems may be configured for extremely low power usage, and be adapted for use in modulating inflammation by stimulation of the cervical vagus nerve, because (1) the stimulation is extremely low duty cycle stimulation (e.g., long off times, brief, relatively low-intensity on times (stimulation a few times/day for <a few minutes), which allows the use of solid-state batteries and less than on minute charging cycles following a full day of modulation; (2) the microstimulators typically use two electrodes and a non-traditional, hermetic feed-through that reduces complexity and size; (3) the microstimulator may use a single bipolar current source that is targeted to a specific nerve; and (4) ultra-small, ultra-low power microprocessors may be used.

In some variations of the system, the charger may be a belt-like loop that fastens around the patient's neck so that power may be transmitted by the loop to the implant. The external controller may be an electronic prescription pad.

As described in greater detail below, the implantable microstimulator may comprise a hermetically sealed capsule body having at least two conductive regions, the capsule body surrounding a resonator, battery and an electronic assembly sealed within the capsule body, wherein the electronic assembly is connected to the capsule body by a suspension configured to absorb mechanical shock. In this variation the electronic assembly may comprise power management circuitry configured to receive power from the resonator to charge the battery, and a microcontroller configured to control stimulation of the vagus nerve from the conductive regions of the capsule body.

For example, also described herein are systems for treating chronic inflammation in a patient including: an implantable microstimulator configured for implantation around a cervical portion of a vagus nerve to modulate inflammation by applying low duty-cycle stimulation to the vagus nerve; a POD configured to hold the implantable microstimulator in contact with a patient's vagus nerve; a charger configured to be worn around the patient's neck and to charge the implantable microstimulator implanted within the patient's neck region; and an external controller configured to communicate with the microstimulator through the charger and to thereby set the dose amplitude and dose interval for the microstimulator, wherein microstimulator is configured to continuously modulate inflammation while charging by the charger for less than 10 minutes per week. The system may be configured to charge the implantable microstimulator for less than about 10 minutes per day, 10 minutes per week, etc.

Any of the chargers or external controllers described herein may be used as part of a system.

Also described herein are leadless, implantable microstimulator devices for treating chronic inflammation, the device comprising: a hermetically sealed capsule body; at least two electrically conductive capsule regions, wherein each region electrically connects to an electrode for applying stimulation to a vagus nerve; a resonator within the sealed capsule body; a battery within the sealed capsule body; and an electronic assembly within the sealed capsule body, wherein the electronic assembly is connected to the capsule body by a suspension configured to absorb mechanical shock and make electrical contact; wherein the electronic assembly comprises power management circuitry configured to receive power from the resonator to charge the battery, and a microcontroller configured to control stimulation of the vagus nerve from the conductive capsule regions.

The capsule body may comprise a ceramic body with hermetically sealed titanium alloy ends and integral platinum-iridium electrodes attached thereto.

In some variations, the device further includes an over-temperature control including a thermister that is configured to shut the device down if the operating temperature exceeds a 41° C.

The battery may be a Lithium solid-state battery e.g., (LiPON). The device may also include voltage limiters to limit the amount of power that can charge the battery from the resonator. In some variations, the device includes load stabilizers to reduce communication errors due to power load fluctuations.

In some variations, the at least two electrically conductive capsule regions comprise the ends of the capsule body. For example, the at least two electrically conductive capsule regions may be made from a resistive titanium alloy to reduce magnetic afield absorption.

Any appropriate suspension may be used, such as a clips or springs.

In some variations, the microstimulator device further includes an H-bridge current source with capacitor isolation connecting each of the two electrically conductive capsule regions. The microstimulator may also include one or more temperature sensor configured to detune the resonator to prevent energy absorption if the temperature exceeds a predetermined value. In some variations the microstimulator includes an overvoltage sensor configured to detune the resonator to prevent energy absorption. The microstimulator may also include a current limiter configured to limit current from the resonator to enable reliable powerup.

Any appropriate resonator may be used with the microstimulator. For example, the resonator may be a coil and capacitor configured to resonate at about 131 KHz+/−2%. The resonator may comprise a ferrite coil wherein the ferromagnetic material is chosen to maximize permittivity in the operating range and minimize permittivity and energy absorption from higher frequency sources such as MRI and Diathermy devices.

The electronic assembly of the microstimulator may include telemetry circuitry configured to detect and demodulate control information from the resonator and communicate the control information with the microcontroller.

Also described herein are leadless, implantable microstimulator device for treating chronic inflammation by stimulation of a cervical region of a vagus nerve that include: a hermetically sealed capsule body having two electrically conductive capsule end regions separated by a central non-conductive region, wherein each conductive region is configured to electrically connect to an electrode for applying stimulation to a vagus nerve; a resonator, battery and electronic assembly within the sealed capsule body; a suspension connecting the electronic assembly to the capsule body to absorb mechanical shock; wherein the electronic assembly comprises power management circuitry configured to receive power from the resonator to charge the battery, and a microcontroller configured to control stimulation of the vagus nerve from the conductive capsule regions.

Also described herein are chargers. For example, a charger device configured to be worn around a patient's neck for charging a microstimulator implanted in the patient's neck may include: an energizer coil configured to fit around the patient's neck; a latch configured to releasably secure together two ends of the energizer coil to close the energizer coil and form a solenoid loop around the patient's neck; and a class-D amplifier driving the solenoid loop and configured to create a magnetic field of between about 40 and 100 A/m at a frequency of between about 120 and 140 KHz. The latch may comprise a plurality of pins making electrical connection between the ends of the energizer coil, the pins configured to maintain a low coil resistance and high Q.

In some variations, the class-D amplifier comprises a high efficiency class-D amplifier. The class-D amplifier may be configured to be driven at a variable frequency to maximize power transfer. The class-D amplifier output may be driven to optimize the microstimulator power absorption by measuring the back-telemetry modulation depth. In some variations, the class-D amplifier controls temperature and prevents telemetry channel saturation. The class-D amplifier driving the solenoid loop may be configured to create a magnetic field of between about 47-94 A/m at a frequency of between about 127-135 KHz.

The charger devices may also include a digitally compensated pwm circuit to modulate the magnetic field strength and tune the power. The device further comprising resonators that are adjustable to between about 127 KHz to 135 KHz. In some variations, the charger device also includes a telemetry system. The telemetry system may include a microprocessor configured to modulate a transmitter collector voltage to send data.

Any of the chargers described herein may also include one or more displays or indicators (e.g., lights).

Also described herein are charger devices configured to be worn around a patient's neck for charging a microstimulator implanted in the patient's neck. A charger device may include: a solenoid loop configured to be worn around the patient's neck; a class-D amplifier driving the solenoid loop and configured to create a magnetic field of between about 40 and 100 A/m at a frequency of between about 120 and 140 KHz.

Methods of treating chronic inflammation are also described herein, using any (including subsets of) the devices and systems described. For example, described herein are methods of treating chronic inflammation in a patient, including the steps of: implanting a microstimulator in the patient's neck in electrical communication with a cervical region of the subject's vagus nerve; and charging and programming the implanted microstimulator from a charger worn around the subject's neck. The method may also include applying electrical energy to the vagus nerve to modulate inflammation. The method may also include programming the microstimulator using an external controller and transmitting control information from the charger.

The step of inserting the microstimulator may include inserting the microstimulator into a Protection and Orientation device (POD) that at least partially surrounds the vagus nerve, wherein the POD is configured to secure the microstimulator in communication with the vagus nerve.

In some variations, the step of inserting the microstimulator comprises implanting a microstimulator having a hermetically sealed capsule body with at least two electrically conductive capsule regions separated by a non-conductive region and a resonator, battery and electronic assembly within the sealed capsule body, and a suspension connecting the electronic assembly to the capsule body to absorb mechanical shock.

In any of these methods for treatment, the method may include the step of securing a charging device around the patient's neck. For example, the method may include securing a charging device around the patient's neck by latching the charging device around the patient's neck to form a complete solenoid loop.

The step of charging and programming the implanted microstimulator may include emitting a magnetic field of between about 40 and 100 A/m at a frequency of between about 120 and 140 KHz from the charger.

Also described herein are methods of treating chronic inflammation in a patient, the method comprising: implanting a microstimulator in the patient's neck in electrical communication with a cervical region of the subject's vagus nerve; stimulating the subject's vagus nerve to modulate inflammation; securing a charging device around the patient's neck; and charging the implanted microstimulator from a charger worn around the subject's neck for less than 20 minutes per week by emitting a magnetic field of between about 40 and 100 A/m at a frequency of between about 120 and 140 KHz from the charger.

The above summary of the invention is not intended to describe each illustrated embodiment or every implementation of the present invention, but to highlight certain key features. The figures and the detailed description that follow more particularly exemplify these embodiments and features.

BRIEF DESCRIPTION OF THE DRAWINGS

FIG. 1B shows another variation of a system for modulating chronic inflammation, including a microstimulator, charger ("energizer"), and system programmer/controller ("prescription pad").

FIG. 1D is a block diagram schematically illustrating the microstimulator and the charger.

FIGS. 5A-5D show end, side perspective, top and side views, respectively, of one variation of a sleeve ("POD") for securing the microstimulator around a nerve such as the vagus nerve.

FIGS. 6A-6D show end, side perspective, top and side views, respectively, of one variation of a microstimulator with integral electrode contacts.

DETAILED DESCRIPTION

Systems for electrically stimulating one or more nerves to treat chronic inflammation may include an implantable, wireless microstimulator such as those described herein and an external charging device (which may be referred to as a charging wand, charger, or energizer). In some variations the system also includes a controller such as a "prescription pad" that helps control and regulate the dose delivered by the system. The microstimulator may be secured in position using a securing device (which may be referred to as a "POD") to hold the microstimulator in position around or adjacent to a nerve. These micro stimulators are designed and adapted for treatment of chronic inflammation, and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the antiinflammatory pathway without significantly depressing heart rate or triggering any number of unwanted effects from the vagus nerve or other neural connections. Any of the nerves of the inflammatory reflex, including the vagus nerve, may be treated as described herein using the systems described.

Figure 1A:
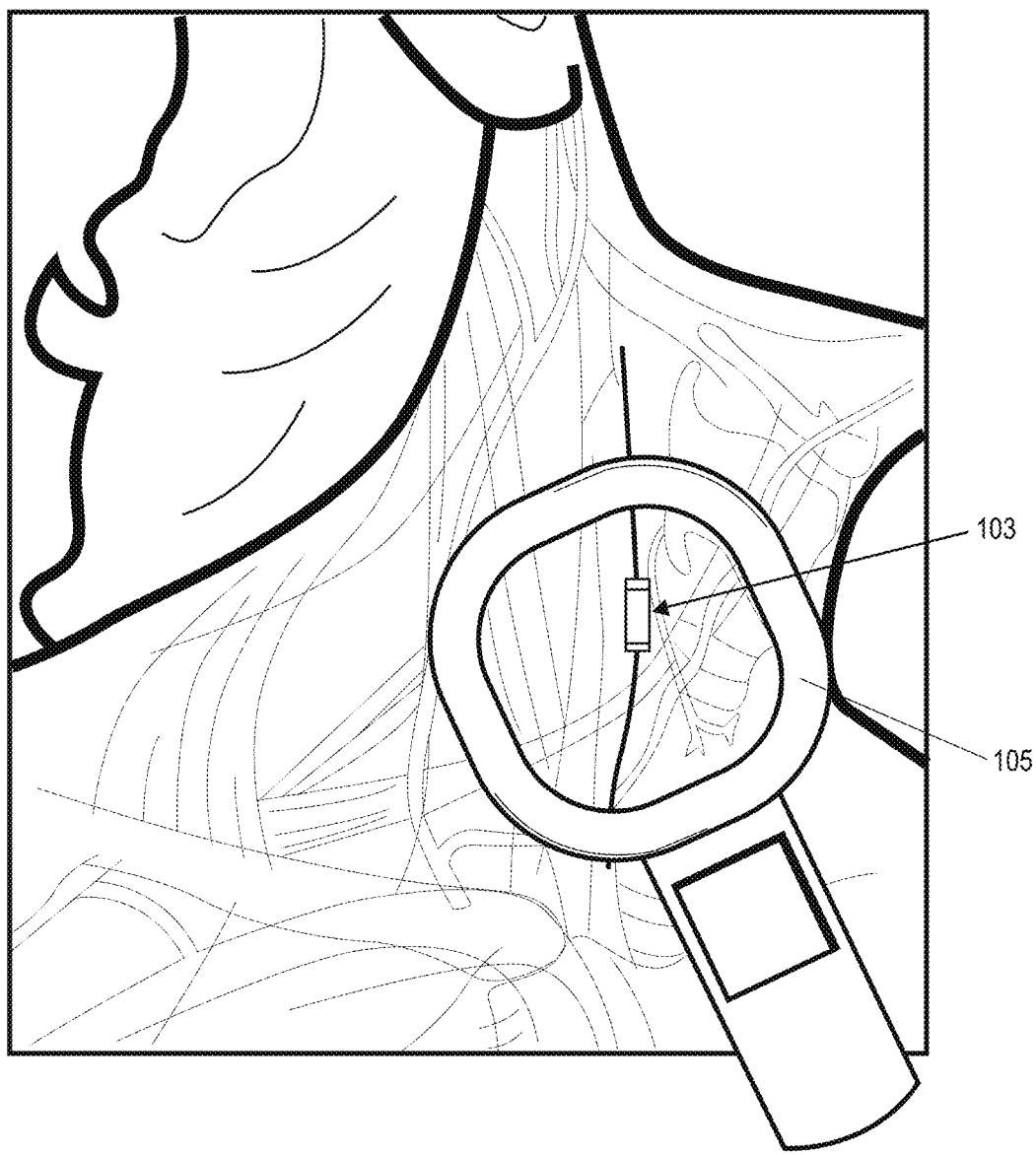
FIG. 1A shows one variation of a system for modulating chronic inflammation including a leadless microstimulator (shown connected to the vagus nerve) and an external charger/controller.

For example, FIG. 1 illustrates one variation of a system for treating chronic inflammation that includes a microstimulator contained in POD that is mounted on cervical vagus nerve and charged a programmed by an external charger/programmer unit. This variation of a system includes a microstimulator 103 that has been implanted to contact the vagus nerve as shown. The implant may be programmed, controlled and/or charged by a charger/controller 105 device. In this variation the charger/controller is a loop with a wand region.

FIG. 1B shows another variation of a system for treating chronic inflammation that also includes an implantable microstimulator 103 (shown inserted into a POD to hold it in position relative to a nerve) and a charging device ("energizer" 105) configured as a collar to be worn around the subject's neck and charge the implant. Optionally, the system may include a prescription pad 107 which may be a separate dedicated device or part of a mobile or other handheld device (e.g., an application to run on a handheld device).

Figure 1C:
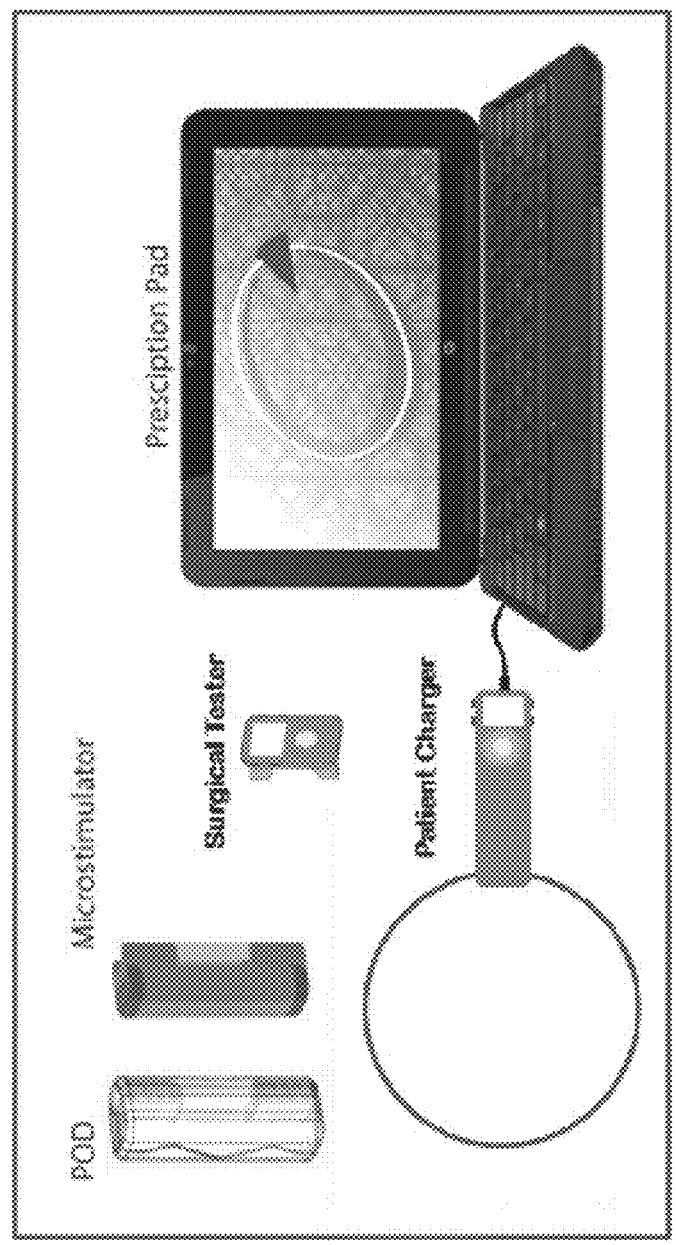
FIG. 1C shows another variations of a system for modulating chronic inflammation, including a microstimulator, a securing device (POD) for securing the leadless stimulator to the nerve, an external charger, a system programmer/controller ("prescription pad") and an optional surgical tester.

FIG. 1C shows another variation of a system for treating chronic inflammation. The systems described herein may also be referred to as systems for the neural stimulation of the cholinergic anti-inflammatory pathway (NCAP). These systems may be configured as chronic implantable systems. In some variations, the systems are configured to treat acutely (e.g., acute may 8 hours or less), sub-acutely (expected to occur for fewer than 30 days), or chronically (expected to occur for more than 30 days).

In general, the systems described herein may be configured to apply electrical stimulation at a minimum level necessary to modulate the inflammatory reflex (e.g., modulating cytokine release) characterized by the Chronaxie and rheobase. Chronaxie typically refers to the minimum time over which an electric current double the strength of the rheobase needs to be applied in order to stimulate the neuron. Rheobase is the minimal electrical current of infinite duration that results in an action potential. As used herein, cytokines refer to a category of signaling proteins and glycoproteins that, like hormones and neurotransmitters, are used extensively in cellular communication.

The NCAP Systems described herein are typically intended for the treatment of chronic inflammation through the use of implanted neural stimulation devices (micro stimulators) to affect the Neural Stimulation of the Cholinergic Anti-inflammatory Pathway (NCAP) as a potential therapeutic intervention for rheumatologic and other inflammation-mediated diseases and disorders. Neurostimulation of the Cholinergic Anti-inflammatory Pathway (NCAP) has been shown to modulate inflammation. Thus, the treatment and management of symptoms manifested from the onset of disease (e.g., inflammatory disease) is based upon the concept of modulating the Cholinergic Anti-inflammatory Pathway. The NCAP pathway normally maintains precise restraint of the circulating immune cells. As used herein, the CAP is a reflex that utilizes cholinergic nerve signals traveling via the Vagus nerve between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent vagus nerve signals. NCAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Under this model, remote inflammation is then dampened by down-regulated cytokine levels. Stimulation of the vagus nerve with a specific regiment of electrical pulses regulates production of pro-inflammatory cytokines. In-turn, the down regulation of these cytokines may reduce localized inflammation in joints and other organs of patients with autoimmune and inflammatory disorders.

The NCAP System includes a neurostimulator that may trigger the CAP by stimulating the cervical vagus nerve. The NCAP System issues a timed burst of current controlled pulses with sufficient amplitude to trigger the CAP at a particular interval. These two parameters, Dose Amplitude and Dose Interval, may be used by a clinician to adjust the device. For example, the clinician may set the Dose Amplitude by modifying the current level. The Dose Interval may be set by changing the duration between Doses (e.g. 12, 24, 48 hours).

In some variations, dose amplitude may be set to within the Therapy Window. The Therapy window is defined as the lower limit of current necessary to trigger the CAP, and the upper limit is the level at which the Patient feels uncomfortable. The lower limit is called the Threshold (T), and the uncomfortable level is called Upper Comfort Level (UCL).

Dose Amplitude thresholds are nonlinearly dependent upon Current (I), Pulse width (PW), Pulse Frequency (PF), and Burst Duration (BD). Amplitude is primarily set by charge (Q), that is Current (I)×Pulse width (PW). In neurostimulation applications current has the most linear relationship when determining thresholds and working within the therapy window. Therefore, the clinician may modify Dose Amplitude by modifying current. The other parameters are held to experimentally determined defaults. Pulse width is selected to be narrow enough to minimize muscle recruitment and wide enough to be well above the chronaxie of the targeted neurons. Stimulus duration and pulse frequency was determined experimentally in Preclinical work.

Dose Interval may be specific for particular diseases and the intensity of diseases experienced by a patient. Our initial research has indicated that the cervical portion of the vagus nerve may be an ideal anatomic location for delivery of stimulation. The nerve runs through the carotid sheath parallel to the internal jugular vein and carotid artery. At this location, excitation thresholds for the vagus are low, and the nerve is surgically accessible. We have not found any significant difference in biomarker modulation (e.g., modulation of cytokines) between right and left. Even though the right vagus is thought to have lower thresholds than the left in triggering cardiac dysrythmias, the thresholds necessary for NCAP are much lower than those expected to cause such dysrythmias. Therefore a device delivering NCAP can safely be applied to either the right or left vagus.

We have also found, surprisingly, that the Therapy Window is maximized on the cervical vagus through the use of a bipolar cuff electrode design. Key parameters of the cuff may be: spacing and shielding of the contacts. For example, the contact points or bands may be spaced 1-2 diameters of the vagus nerve apart, and it may be helpful to shield current from these contacts from other nearby structures susceptible to inadvertent triggering. The cuff may be further optimized by using bands which are as long and wide as possible to reduce neurostimulator power requirements.

Figure 3A:
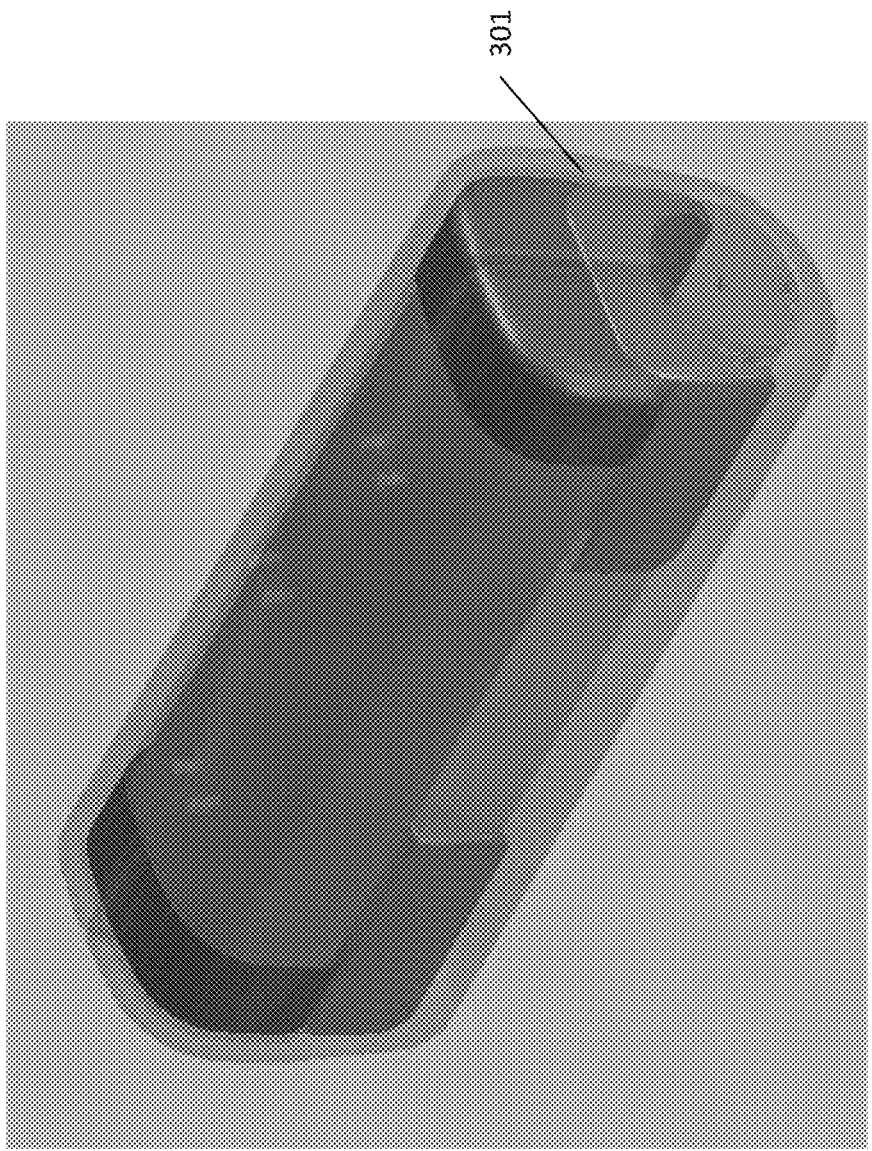
FIG. 3A shows one variation of a microstimulator in a POD configured to surround a nerve of the inflammatory reflex.
Figure 3B:
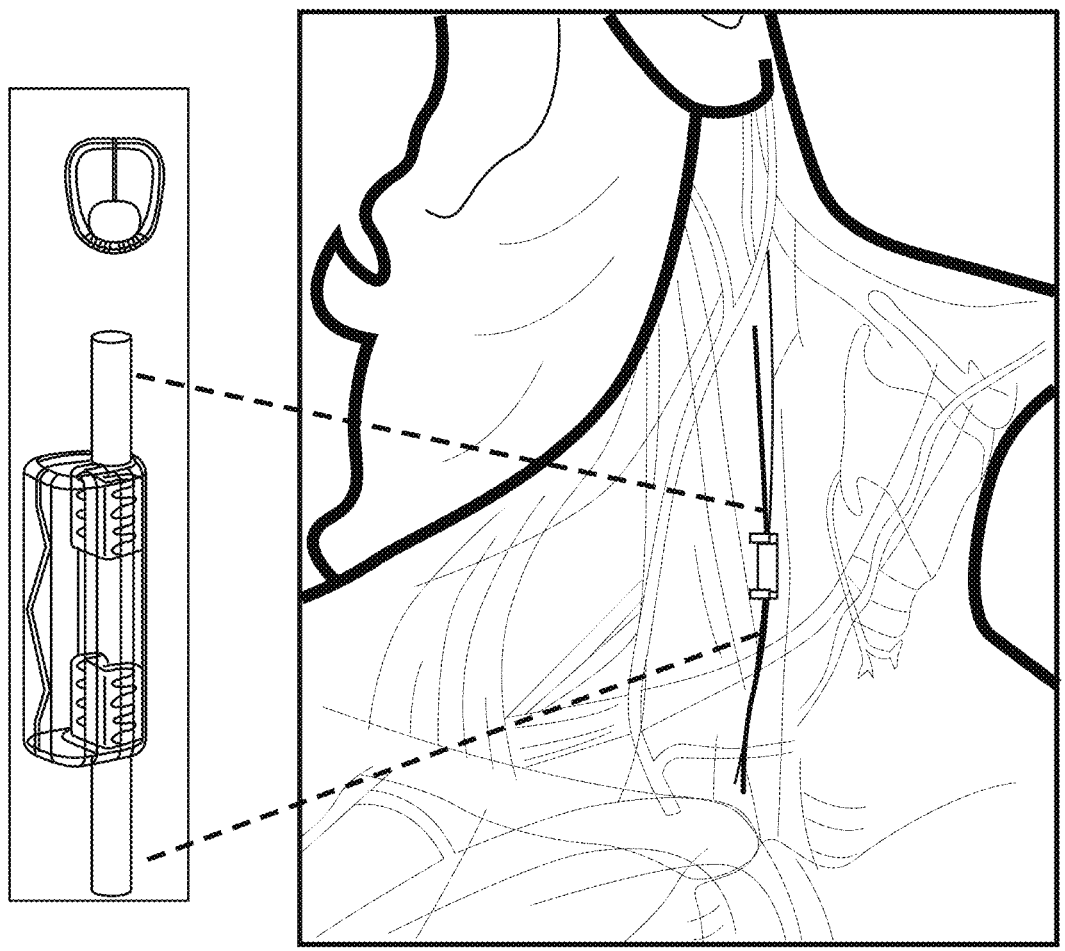
FIG. 3B shows an enlarged view of the microstimulator and POD.

Thus, any variations of the systems described herein (e.g., the NCAP system) may be implemented with a Cuff, Lead and Implantable Pulse Generation (IPG), or a Leadless Cuff. The preferred implementation is a leadless cuff implemented by a microstimulator with integral electrode contacts in intimate contact with the nerve and contained within a Protection and Orientation Device (POD). This is illustrated in FIGS. 3A and 3B. The POD 301 may form a current shield, hold the microstimulator into place against the vagus nerve, and extend the microstimulator integral contacts with integral contacts in the POD itself. The POD is typically a polymer shell that encapsulates a microstimulator implant and that allows a nerve to run through the interior against the shell wall parallel to the length of the microstimulator implant. Within the shell of the POD, the microstimulator implant remains fixed against the Vagus nerve so the electrodes remain in contact with the nerve. The POD anchors the implant in place and prevents the implant from rotating or separating from the nerve, as well as maintaining contact between the electrodes and the nerve and preserving the orientation as necessary for efficient external charging of the microstimulator battery.

Referring back to FIG. 1C, the system may include an implantable microstimulator contained in a POD, a Patient Charger, and a prescription pad that may be used by the clinician to set dosage parameters for the patient. This system may evaluate the efficacy, safety, and usability of an NCAP technology for chronic treatment of clinical patients. The system can employ a Prescription Pad (external controller) that may include the range of treatment options.

As described in more detail in U.S. patent application Ser. No. 12/874,171, titled "PRESCRIPTION PAD FOR TREATMENT OF INFLAMMATORY DISORDERS," U.S. Patent Application Publication No. 2011-0054569-A1 (now abandoned), previously incorporated by reference in its entirety, the Prescription Pad may incorporate workflows in a simplified interface and provide data collection facilities that can be transferred to an external database utilizing commercially robust and compliant methods and procedures. In use, the system may be recommended for use by a clinician after assessing a patient; the clinician may determine that treatment of chronic inflammation is warranted. The clinician may then refer the patient to an interventional doctor to implant the microstimulator. Thereafter then clinician (or another clinician) may monitor the patient and adjust the device via a wireless programmer (e.g. prescription pad). The clinician may be trained in the diagnosis and treatment procedures for autoimmune and inflammatory disorders; the interventional placement of the system may be performed by a surgeon trained in the implantation of active neurostimulation devices, with a sufficient depth of knowledge and experience regarding cervical and vagal anatomy, experienced in performing surgical dissections in and around the carotid sheath.

The system may output signals, including diagnostics, historical treatment schedules, or the like. The clinician may adjust the device during flares and/or during routine visits. Examples of implantation of the microstimulator were provided in U.S. Ser. No. 12/874,171. For example, the implant may be inserted by making an incision in the skin (e.g., ≈3 cm) along Lange's crease between the Facial Vein and the Omohyoid muscle, reflecting the Sternocleidomastoid and gaining access to the carotid sheath. The IJV may be displaced, and the vagus may be dissected from the carotid wall (≤2 cm). A sizing tool may be used to measure the vagus, and an appropriate Microstimulator and POD Kit (small, medium, large) may be selected. The POD may then be inserted under nerve with the POD opening facing the surgeon, so that the microstimulator can be inserted inside POD so that the microstimulator contacts capture the vagus. The POD may then be sutured shut. In some variations a Surgical Tester may be used to activate the microstimulator and perform system integrity and impedance checks, and shut the microstimulator off, during or after the implantation. In other variations the surgical tester may be unnecessary, as described in greater detail below.

A physician may use the Patient Charger to activate the microstimulator, perform integrity checks, and assure sufficient battery reserve exists. Electrodes may be conditioned with sub-threshold current and impedances may be measured. A Physician may charge the microstimulator. In some variations a separate charger (e.g., an "energizer") may be used by the patient directly, separate from the controller the physician may use. Alternatively, the patient controller may include controls for operation by a physician; the system may lock out non-physicians (e.g., those not having a key, code, or other security pass) from operating or modifying the controls.

In general, a physician may establish safe dosage levels. The physician may slowly increment current level to establish a maximum limit (Upper Comfort Limit). This current level may be used to set the Dosage Level. The exact procedure may be determined during this clinical phase.

The Physician may also specify dosing parameters that specify dosage levels and dosage intervals. The device may contain several concurrent dosing programs which may be used to acclimate the patient to stimulus, gradually increase dosage until efficacy is achieved, reset tachyphylaxis, or deal with unique patient situations.

As mentioned, a patient may use the Patient Charger to replenish the microstimulator battery at necessary times (e.g., every day, every week, etc.). A clinician may also work with the patient to setup a schedule based upon the patient's stimulation needs and lifestyle. In some variations, the microstimulator battery charging is achieved by expanding the Patient Charger loop, putting the loop over the head, and closing the handle to close the loop, which may position the charger sufficiently near the implanted device. Charging may start automatically or the user (patient or physician) can push a charge button. The patient may watch the progress on the Patient Charger and may be signaled when charging is complete. The length of the charge may depend primarily upon dosage level. The more often a patient charges, the shorter the charge time may be.

The charger and/or implant may include a clock, and in some variations the patient may set the time zone on the Patient Charger to reflect his/her location. The Patient Charger may update the microstimulator time parameters while charging. This may enable the patient to adjust for travel related time zone changes or daylight savings time adjustments. Because stimulation may be perceptible (felt by the patient), it may be important that the patient receive the stimulation at the same time(s) every day.

If the patient does not charge frequently enough, the system may automatically cease treatment when about 3 months of standby battery remains. Once treatment stops the patient must visit their physician to restart treatment, to avoid damage to the implant requiring re-implantation.

In general, the microstimulator and POD can be suitable for chronic treatment with a design life of 10 years or more. The battery may support a 20 year life. Microstimulator battery charging intervals may be dependent on patient dose settings, however, as described in greater detail below, the system may be configured to conserve power and therefore minimize charging intervals and/or times, greatly enhancing patient comfort and compliance.

The microstimulator and POD may be packaged into kits. Any of the systems described herein may also include a surgical kit with the items necessary for the implantation of Microstimulator and POD. This does not prevent the surgeon, during a revision, from using the existing POD and only replacing the microstimulator. System kits may be available for small, medium, and large vagus nerves. A vagus nerve sizing kit may be available to determine which kit to use. In some variations the microstimulator and POD have a loose fit such the lumen of the device and the widest part of the nerve has a loose fit without constraining blood flow, and allowing axial flexibility and both compressive and tensile forces on the device without damaging the nerve. For example, the POD may encapsulate the microstimulator so current leakage may occur through vagus nerve access ports. All other sources of current leakage may be <25 uA when POD is sutured shut. The microstimulator may have a slot for the vagus nerve. This slot may have three sizes (approximately small, medium, large) for vagus nerves of approximately (e.g., +/−5%, 10%, 20%, 30%, 40%, 50%): 2 w×1.5 h; 3 w×2 h; 4 w×3 h (mm).

Implantable components of the microstimulator and POD and components are typically applied within the sterile barrier during the interventional procedure and may be supplied sterile. Sterilization method may be Ethylene Oxide (EO).

In some variations, the POD may be secured by 1-3 sutures and may include a marker to easily allow surgeon to match suture holes minimizing failure. The POD may be configured so that over-tightening the sutures does not cause vagal devascularization. The microstimulator and POD cross sectional area may not exceed 60 mm2 including the largest nerve model. The volume including the largest nerve model may be less than 1.5 cc.

Because rotation around the axis and movement up and down on the vagus nerve may occur during the healing period. The Patient Charger may allow accommodation of this movement.

In some variations, the microstimulator may have a bipolar stimulation current source that produce as stimulation dose with the characteristics shown in table 1, below. In some variation, the system may be configured to allow adjustment of the "Advanced Parameters" listed below; in some variations the parameters may be configured so that they are predetermined or pre-set. In some variations, the Advanced Parameters are not adjustable (or shown) to the clinician. All parameters listed in Table 1 are ±5% unless specified otherwise.

TABLE 1

Microstimulator parameters

| Property | Value | Default |
| --- | --- | --- |
| Dosage Amplitude (DA) | 0-5,000 µA in 25 µA steps | 0 |
| Intervals | Minute, Hour, Day, Week, Month | Day |
| Number of Doses per Interval | N = 60 Maximum | 1 |
| Advanced Parameters | | |
| Pulse width Range (PW) | 100-1,000 µS in 50 µS increments | 200 |
| Stimulus Duration (SD) | 1-1000 seconds per dose | 60 |
| Pulse Frequency (PF) | 1-50 Hz | 10 |
| Stimulus Voltage (SV) | ±3.3 or ±5.5 ± 1 Volts | Automatically set by software |
| Constant Current Output | ±15% over supported range of load impedances (200-2000Ω) | |
| Specific Dose Time | Set a specific time between 12:00 am-12:00 am in one minute increments for each Dose Issue | Driven by default table (TBD) |
| Number of Sequential Dosing Programs | 4 maximum | 1 |

The Dosage Interval is defined as the time between Stimulation Doses. In some variations, to support more advanced dosing scenarios, up to four 'programs' can run sequentially. Each program has a start date and time and will run until the next program starts. Dosing may be suspended while the Prescription Pad is in Programming Mode. Dosing may typically continue as normal while charging. Programs may be loaded into one of four available slots and can be tested before they start running Low, Typical, and High Dose schedules may be provided. A continuous application schedule may be available by charging every day, or at some other predetermined charging interval. For example, Table 2 illustrates exemplary properties for low, typical and high dose charging intervals:

TABLE 2 low typical and high dose charging intervals

| Property | Value |
| --- | --- |
| Low Dose Days Charge Interval | 30 days max: 250 µA, 200 µS, 60 s, 24 hr, 10 Hz, ±3.3 V |
| Typical Dose Charge Interval | 30 days max: 1,000 µA, 200 µS, 120 s, 24 hr, 10 Hz, ±3.3 V |
| High Dose Charge Interval | 3.5 days max: 5,000 µA, 500 µS, 240 s, 24 hr, 20 Hz, ±5.5 V, |

The system may also be configured to limit the leakage and maximum and minimum charge densities, to protect the patient, as shown in Table 3:

TABLE 3 safety parameters

| Property | Value |
| --- | --- |
| Hardware DC Leakage Protection | <50 nA |
| Maximum Charge Density | 30 µC/cm$^2$/phase |
| Maximum Current Density | 30 mA/cm$^2$ |

In some variations, the system may also be configured to allow the following functions (listed in Table 4, below):

TABLE 4

Additional functions of the microstimulator and/or controller(s)

| Function | Details |
| --- | --- |
| Charging | Replenish Battery |
| Battery Check | Determine charge level |
| System Check | Self Diagnostics |
| Relative Temperature | Temperature difference from baseline |
| Program Management | Read/Write/Modify a dosage parameter programs |
| Program Up/Download | Transfer entire dosage parameter programs |
| Electrode Impedances | Bipolar Impedance (Complex) |
| Signal Strength | Strength of the charging signal to assist the patient in aligning the external Charge to the implanted Microstimulator. |
| Patient Parameters | Patient Information |
| Patient History | Limited programming and exception data |
| Implant Time/Zone | GMT + Time zone, 1 minute resolution, updated by Charger each charge session |
| Firmware Reload | Boot loader allows complete firmware reload |
| Emergency Stop | Disable dosing programs and complete power down system until Prescription Pad connected |

As mentioned above, in some variations, the system may record function of the microstimulator (e.g., a limited patient history). For example, the system may record: date and time that each program that is started and the associated program parameters; power down events due undercharging; hardware or software exceptions; emergency power down events; compliance events with associated impedance measurement; etc. In some variations, at least the last 50 events may be preserved in a circular buffer. Any of the systems describe herein may be approved for MRI usage at 3 Tesla (e.g., the torque will be less than a maximum threshold, the temperature rise may be less than 4° C., and the blackout area may be less than a maximum threshold volume. In some variations, the microstimulator and POD may be configured to withstand monopolar electrocautery.

The Patient Charger (including the energizer variations) typically fits over a patient's head to charge the implants in the patient's neck. As described in greater detail below, the Patient Charger may support neck circumferences ranging between 28-48 cm and head circumferences of up to 72 cm. The implant and the charger may further be configured so that they orientation of the charger and implant may allow sufficient tolerance to permit charging when worn by the user in a number of positions, without requiring substantial repositioning. The Patient Charger may provide functionality that can be accessed though a connected Prescription Pad or other external controller. For example, Table 5 below lists some function elements that may be accessed by a prescription pad in conjunction with a charger:

TABLE 5 functions that may be performed by prescription pad and charger

| Function | Prescription Pad connected to Charger | Charger Alone |
|---|---|---|
| Charging | Y | Y |
| Battery Check | Y | Y |
| System Check | Y | Y |
| Absolute device Temperature | Y | Used for thermal safety purposes only |
| Program Management | Y | N |
| Program Up/Download | Y | N |
| Electrode Impedances | Y | OK Check Only |
| Signal Strength | Y | Y |
| Patient Parameters | Y | N |
| Patient History | Y | N |
| Implant Time/Zone/Date | Y (time zone not changed) | Y (synced to Charger and changed by patient) |
| Firmware Reload | Y | N |
| Emergency Stop | Y | Y (special sequence) |

In general, a charger (which may be used by a patient directly) may include a recharge reminder alarm (audio and/or visual) that will remind the patient to charger on a daily, weekly, or monthly frequency. The Patient Charger may be charged through a Wall Adapter plug alone or in conjunction with a Charging Dock. The Patient Charger may clearly indicate that it is charging.

In some variations, the Patient Charger firmware will be version controlled and may be updated with Prescription Pad software in the field, or can be updated in the factory. For example, the Prescription Pad software may be controlled and may be updated in the field by the one or more web applications, a USB Dongle, a CD, etc. In some variations, the Prescription Pad may identify the microstimulator through a unique electronic ID electronically available in the microstimulator. The ID may be linked to a serial number that is embossed in the case. However, the Patient Charger may not require knowledge of this ID to charge the device.

In determining a maximum neck diameter for use with the chargers described herein a study measuring Neck Circumference for men (N=460) (above) and women (N=519) (below) against BMI was used. See, e.g., Liubov Ben-Noun, et. al. Neck Circumference as a Simple Screening Measure for Identifying Overweight and Obese Patients, Obesity Research (2001) 9, 470-477. Further, maximum head diameter was determined from an analysis of other studies (such as K M D Bushby, et. Al, Centiles for adult head circumference, Archives of Disease in Childhood 1992; 67: 1286-1287).

Figure 20:
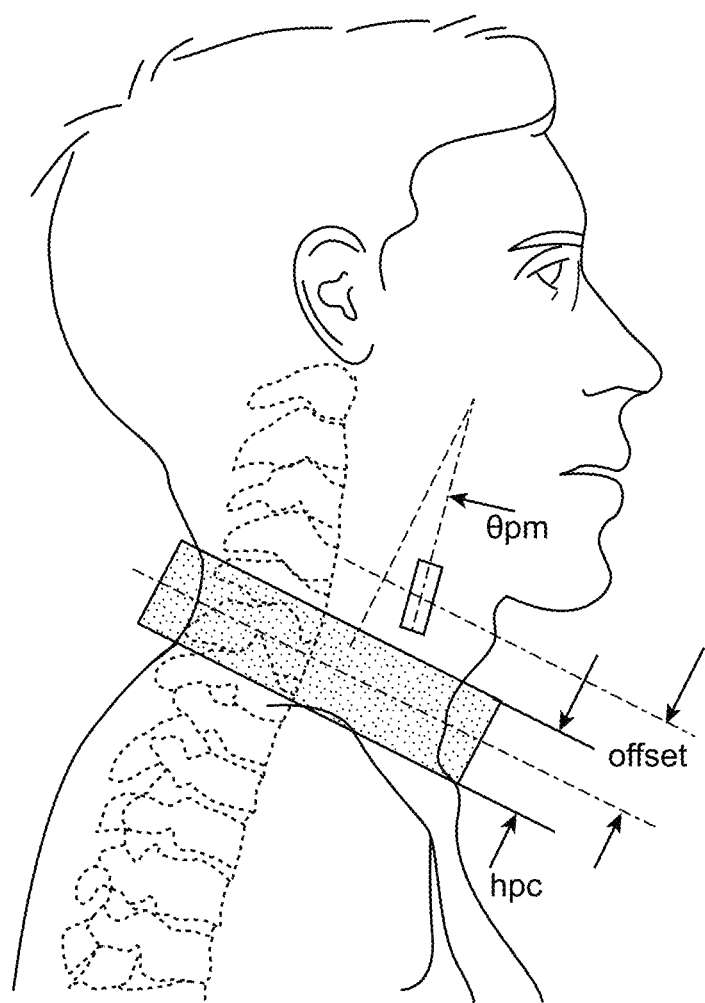
FIG. 20 shows a side view of a patient having an implanted microstimulator.

Based on this analysis, the sizing and placement of the charger around the patient's neck was estimated. For example, see FIG. 20. In this figure, a side view of a patient with an implanted microstimulator is shown in relation to the subject's neck and shoulders. The "offset" is illustrated as the maximum allowable offset between center of Patient Charging Loop and center of implant, θ pm is the maximum angular deviation from the Patient Charging Loops normal vector, and H=Patient Charging Loop Height. These variables were used to determine the necessary properties for the functionality of the charger relative to a typical implanted insert.

Figure 2:
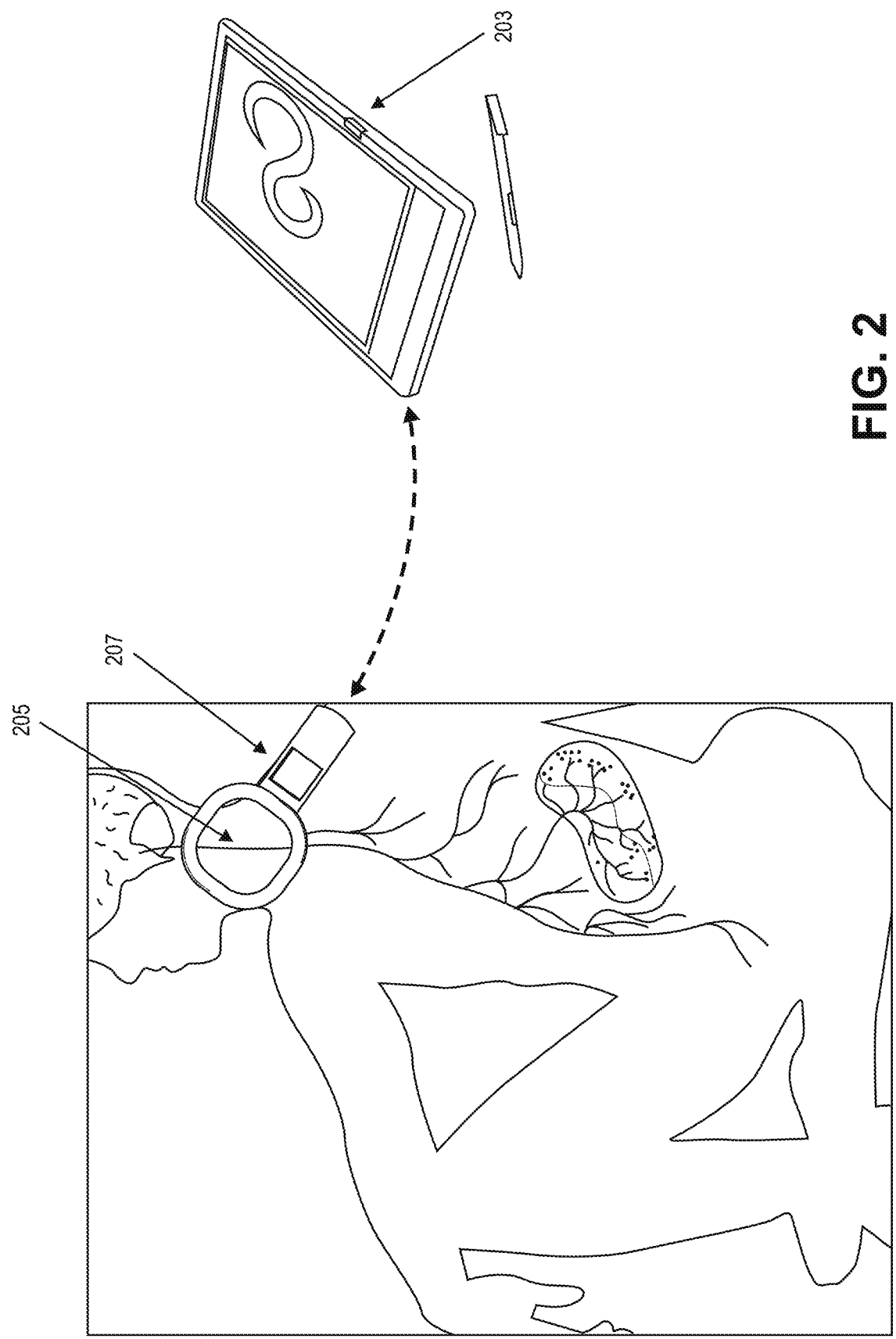
FIG. 2 illustrates one variation of an external system programmer/controller wirelessly connected to a microstimulator.

In some variations, the Prescription Pad may be configured to handle multiple patients and may index their data by the microstimulator Serial Number. For example, a Prescription Pad may handle up to 100,000 patients and 10,000 records per patient, and may store the data in its local memory and may be backed up on an external database. In some variations, during each charging session, accumulated even log contents will be uploaded to the Patient Charger for later transfer to Prescription Pad. The data may or may not be cleared from the microstimulator. For example, FIG. 2 shows the addition of a prescription pad wirelessly connected to the charger/programmer.

Microstimulator

The microstimulators described herein are configured for implantation and stimulation of the cholinergic anti-inflammatory pathway, and especially the vagus nerve. In particular the microstimulators described herein are configured for implantation in the cervical region of the vagus nerve to provide extremely low duty-cycle stimulation sufficient to modulate inflammation. These microstimulators may be adapted for this purpose by including one or more of the following characteristics, which are described in greater detail herein: the conductive capsule ends of the microstimulator may be routed to separate electrodes; the conductive capsule ends may be made from resistive titanium alloy to reduce magnetic field absorption; the electrodes may be positioned in a polymer saddle; the device includes a suspension (e.g., components may be suspended by metal clips) to safeguard the electronics from mechanical forces and shock; the device may include an H-bridge current source with capacitor isolation on both leads; the device may include a built in temperature sensor that stops energy absorption from any RF source by detuning the resonator; the device may include a built-in overvoltage sensor to stop energy absorption from any RF source by detuning resonator; the system may include DACs that are used to calibrate silicon for battery charging and protection; the system may include DACs that are used to calibrate silicon for precision timing rather than relying on crystal oscillator; the system may include a load stabilizer that maintains constant load so that inductive system can communicate efficiently; the system may include current limiters to prevent a current rush so that the microstimulator will power up smoothly from resonator power source; the system may extract a clock from carrier OR from internal clock; the device may use an ultra low power accurate RC oscillator that uses stable temperature in body, DAC calibration, and clock adjustment during charging process; the device may use a solid state LIPON battery that allows fast recharge, supports many cycles, cannot explode, and is easy to charge with constant voltage; and the device may include a resonator that uses low frequency material designed not to absorb energy by high frequency sources such as MRI and Diathermy devices.

Many of these improvements permit the device to have an extremely small footprint and power consumption, while still effectively modulating the vagus nerve.

Figure 4:
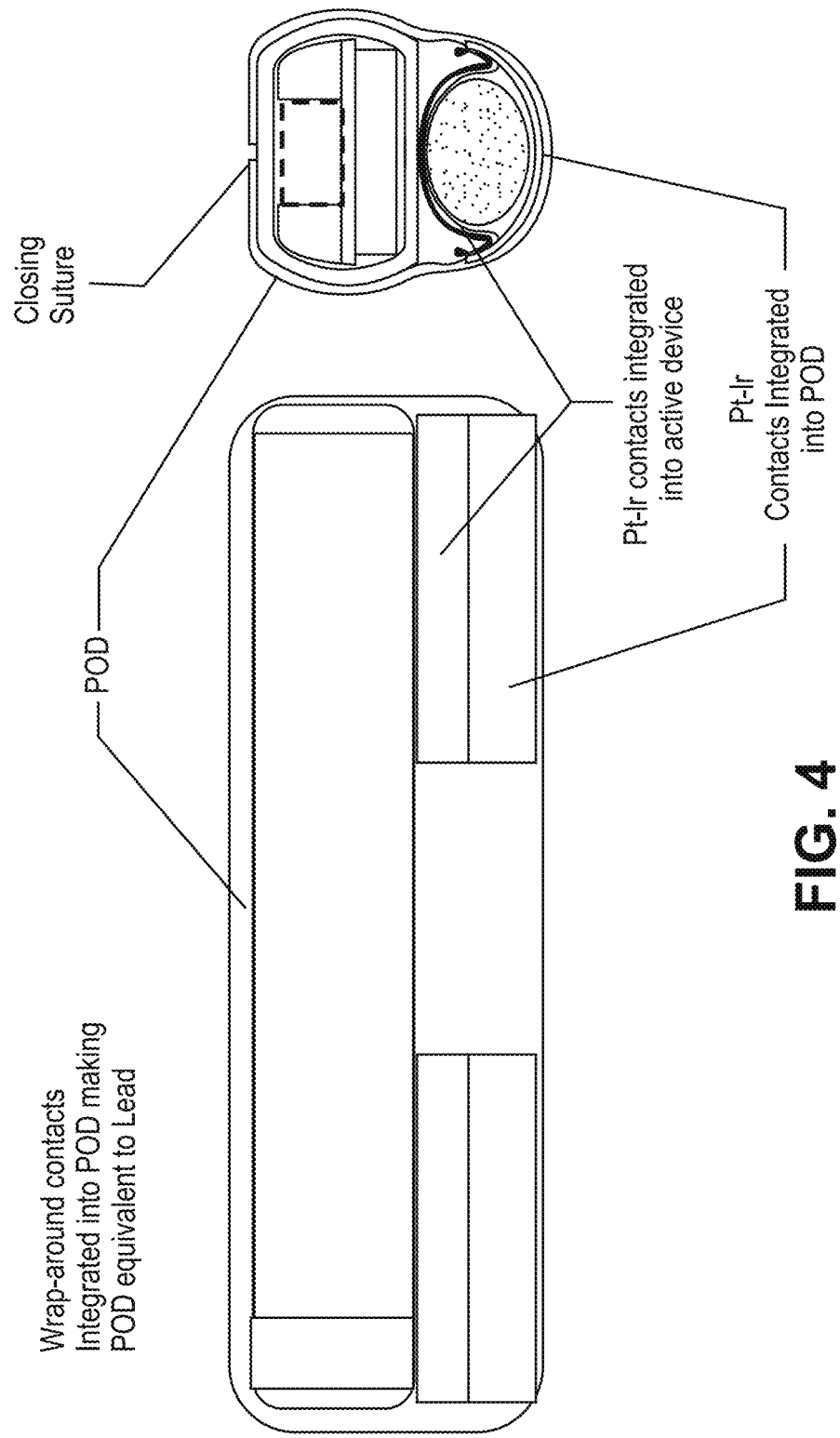
FIG. 4 shows a schematic diagram of a microstimulator and POD around vagus nerve.

As mentioned above, some of the device variations described herein may be used with a POD to secure the implant (e.g., the leadless/wireless microstimulator implant) in position within the cervical region of the vagus nerve so that the device may be programmed and recharged by the charger/programmer (e.g., "energizer"). For example, FIG. 4 shows a schematic diagram of a POD containing a microstimulator. The cross section in FIG. 4 shows the ceramic tube containing electronic assembly that includes the hybrid, battery and coil. The rigid or semi-rigid contacts are mounted on the tube and surround the oval vagus nerve. The POD surrounds the entire device and includes a metal conductor that makes electrical contact with the microstimulator contacts and electrically surrounds the nerve.

FIG. 3A is a perspective drawing of the Pod containing the microstimulator. Sutures (not shown) are intended to be bridged across one to three sets of holes. Electrodes integrated into the pod are not shown but would extend as bands originating and ending on the two outer pairs of suture holes.

Figure 8:
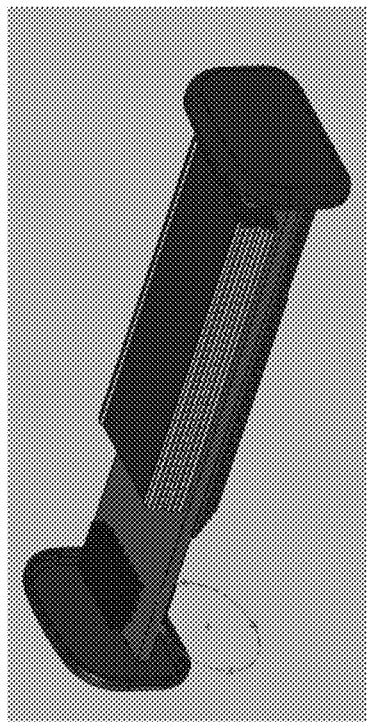
FIG. 8 shows one variation of an electronic assembly and end caps without spring loaded contacts.
Figure 7:
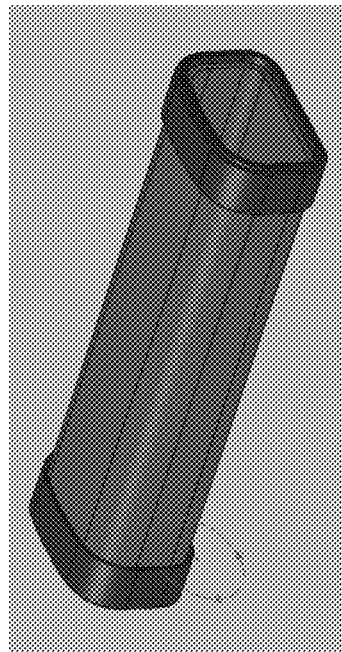
FIG. 7 shows one variations of a ceramic case for a microstimulator with brazed-on receptacles.

FIGS. 5A-D show views of one variation of a POD without an inserted microstimulator. The keying can be seen in the saw tooth pattern so that the surgeon will assure that the device does not twist the suture holes are reinforced with Dacron material embedded in the polymer. The tunnel that the nerve takes is as conformal as possible. Several sizes may be required in order to minimize current leakage and limit fibrous tissue in-growth. FIGS. 6A-D show another variation of a microstimulator from several angles. FIGS. 7-11C illustrate different variations of components of microstimulators as described herein. For example, FIG. 7 shows a ceramic tube forming the outer region of the microstimulator housing with end fixtures allowing the titanium caps to be welded sealing the unit. FIG. 8 shows the electronic assembly with the end caps. The antenna is on top of the hybrid and the battery is below the hybrid. Spring loaded contacts are on the edge of the board (not shown) will press against and make electrical contact with the end caps.

Figure 9A:
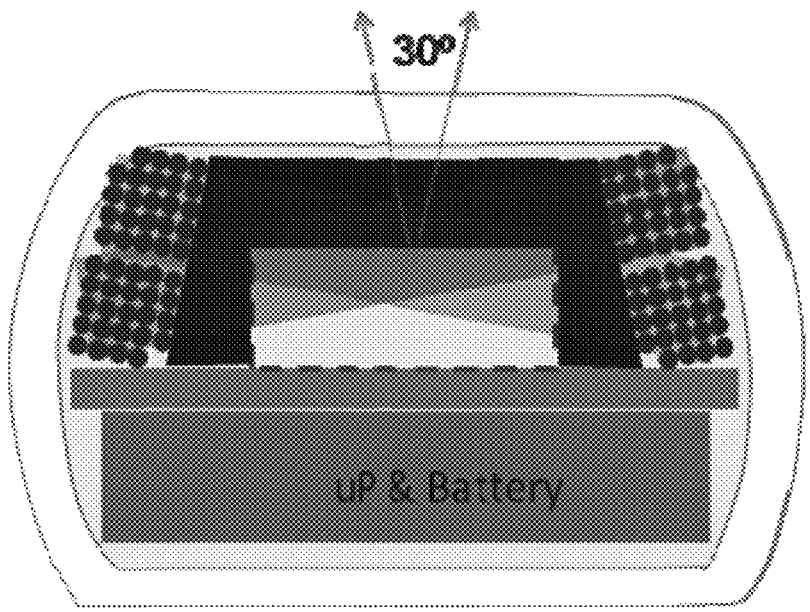
FIG. 9A shows a section though one variation of a microstimulator having non-coplanar antennae.
Figure 9B:
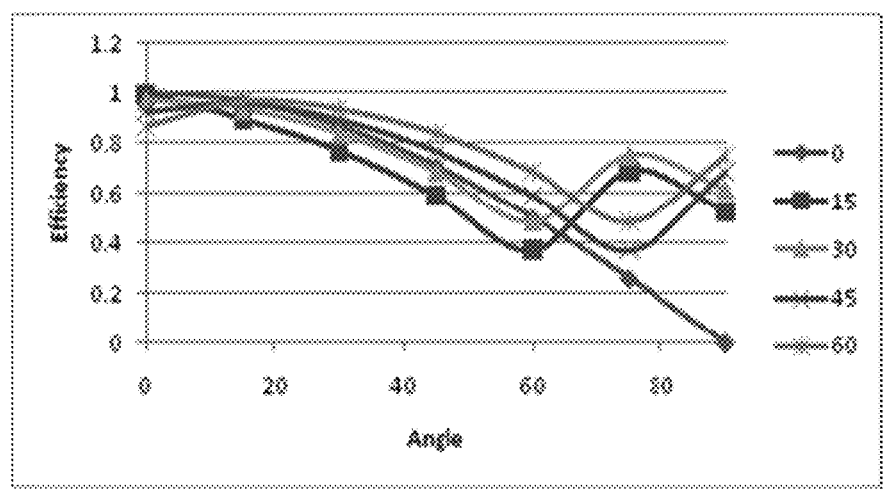
FIG. 9B is a graph illustrating the rotational tolerance (efficiency) of the antennae as the angle is changed.

As described above, the microstimulators described herein are configured to be used with a charger to be worn on a subject's neck. Thus, the microstimulator must be configured to allow charging when wearing the device. FIG. 9A shows a cross section of one variation of a microstimulator showing detail of an inductive antenna wound in two planes to increase the rotational tolerance of the device. The graph in FIG. 9B below shows the relative efficiency when the angle between the two planes is changed.

Figure 10A:
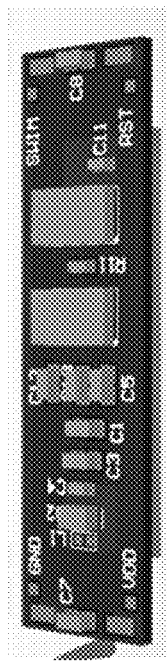
FIGS. 10A-10C show perspective, top and side views, respectively, of an electronic assembly of a microstimulator having a solid-state battery and antenna.
Figure 10B:
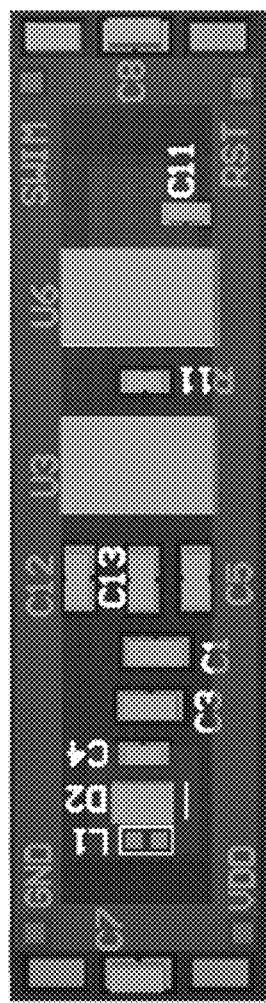
Figure 10C:
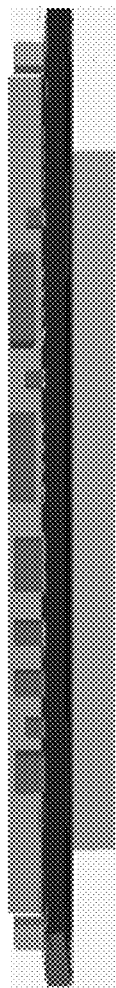
Figure 11A:
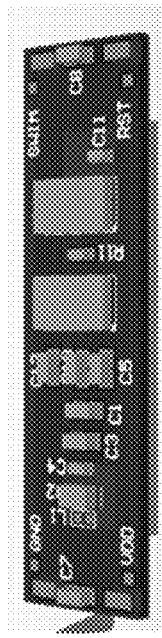
FIGS. 11A-11C show perspective, top and side views, respectively, of an electronic assembly of a microstimulator having a coin cell battery.
Figure 11B:
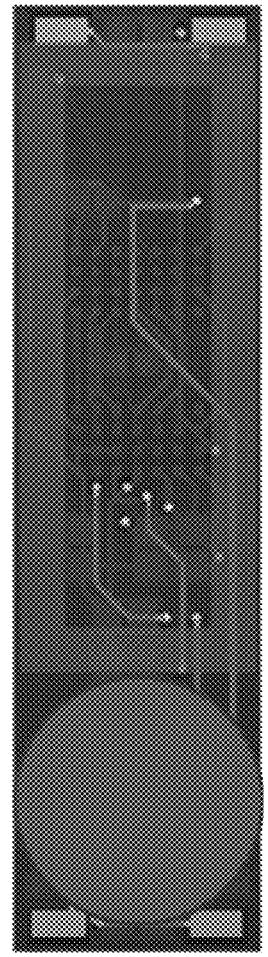
Figure 11C:
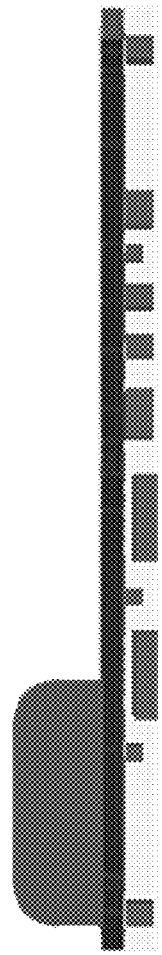

FIGS. 10A-10C show detail of the hybrid microstimulator, in particular showing the integrated circuit and MCU, in addition to the discrete components. The ends of the board have contacts for the spring loaded contacts described above. As shown, the DC protection capacitors are mounted as close as possible to the contacts to avoid other possible DC leakage paths that could develop on the board. FIGS. 11A-C are similar to FIGS. 10A-C except they shows a coin cell rather than a then a thin solid state battery shown in FIGS. 10A-C.

FIGS. 12-19 are circuit diagrams illustrating one variations of a microstimulator system having many of the properties described above, and in particular limits protecting operation and powering of the microstimulator. For example, FIG. 12A is a block diagram of the circuit showing overall function of a microstimulator. Electromagnetic energy is picked up by the resonant circuit formed by the inductor and capacitor. A diode rectifies the energy and another capacitor filters the power supply. A limiter provides the function of limiting the voltage and current to the battery cell that is being charged. J1 is removed for a primary cell system that does not require recharging, for a rechargeable system J1 is always present. S1 is normally connected, and is only disconnected when the battery runs below a level where it is in danger of being damaged. If S1 gets disconnected it is reconnected after the battery is under charge. The real-time-clock (RTC) is normally connected and tracking time. Once charging is complete and the MCU has completed work, it sets up the RTC for a wakeup call. A wakeup call consists of the RTC closing S2 powers up the MCU. The MCU keeps S2 closed until its business is complete. The MCU gets data from the demodulator using the UART to convert the serial asynchronous data to parallel bytes. The UART is also used to modulate the load on the resonant circuit and the data is picked up by the programmer and charger. The MCU stimulates the patient by using current sources. The battery voltage may not be high enough to overcome the electrode impedances, in this case the Voltage multiplier is enabled to increase the stimulation voltage. The bipolar current sources are connected in an H-bridge formation (see FIG. 19) and the output capacitors allow a positive voltage to be swung negatively yielding peak to peak voltage swings double the stimulation voltage.

Figure 14:
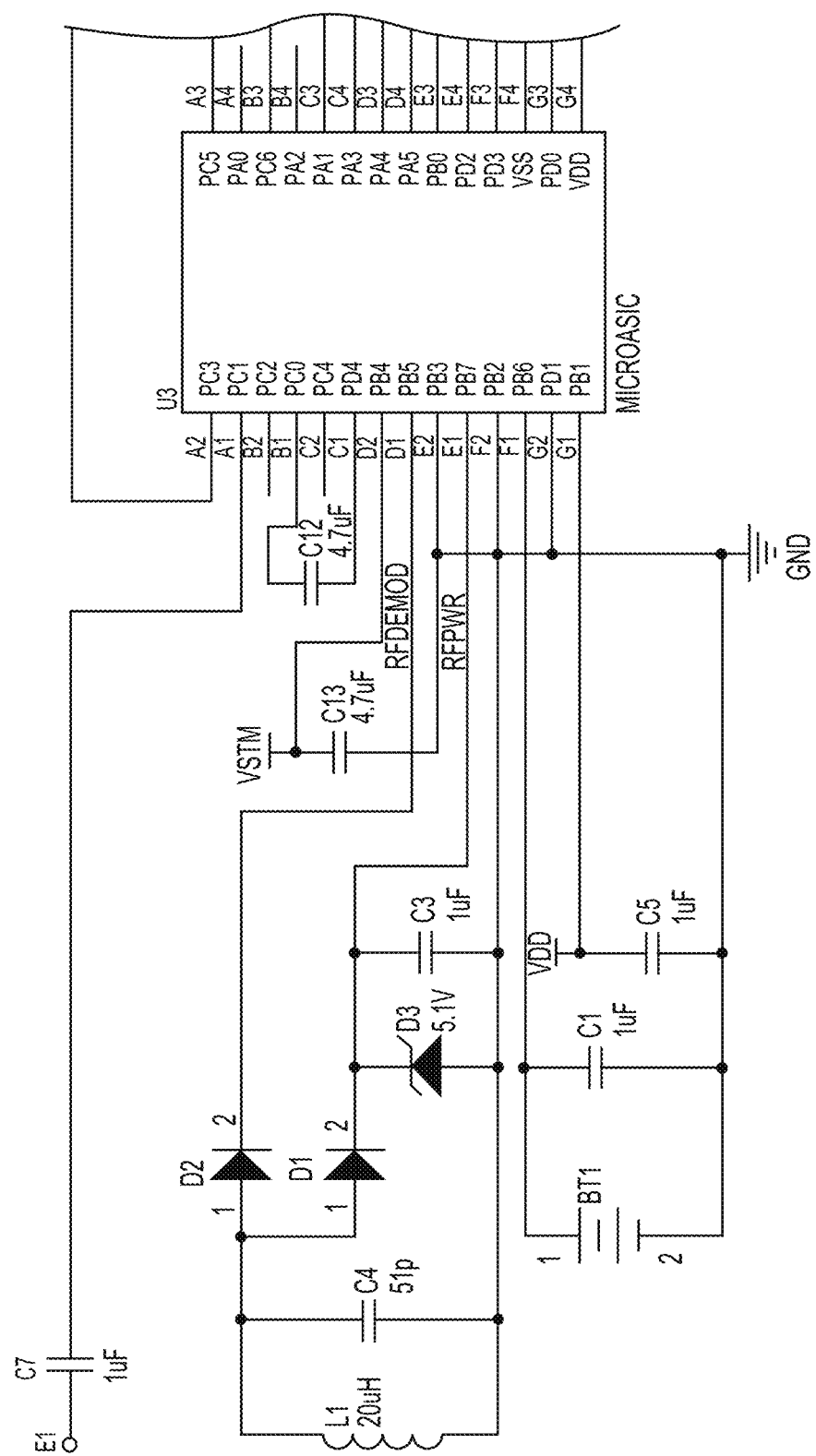
FIG. 14 is a block schematic circuit diagram of one variation of an implant hybrid schematic, as described herein.
Figure 14:
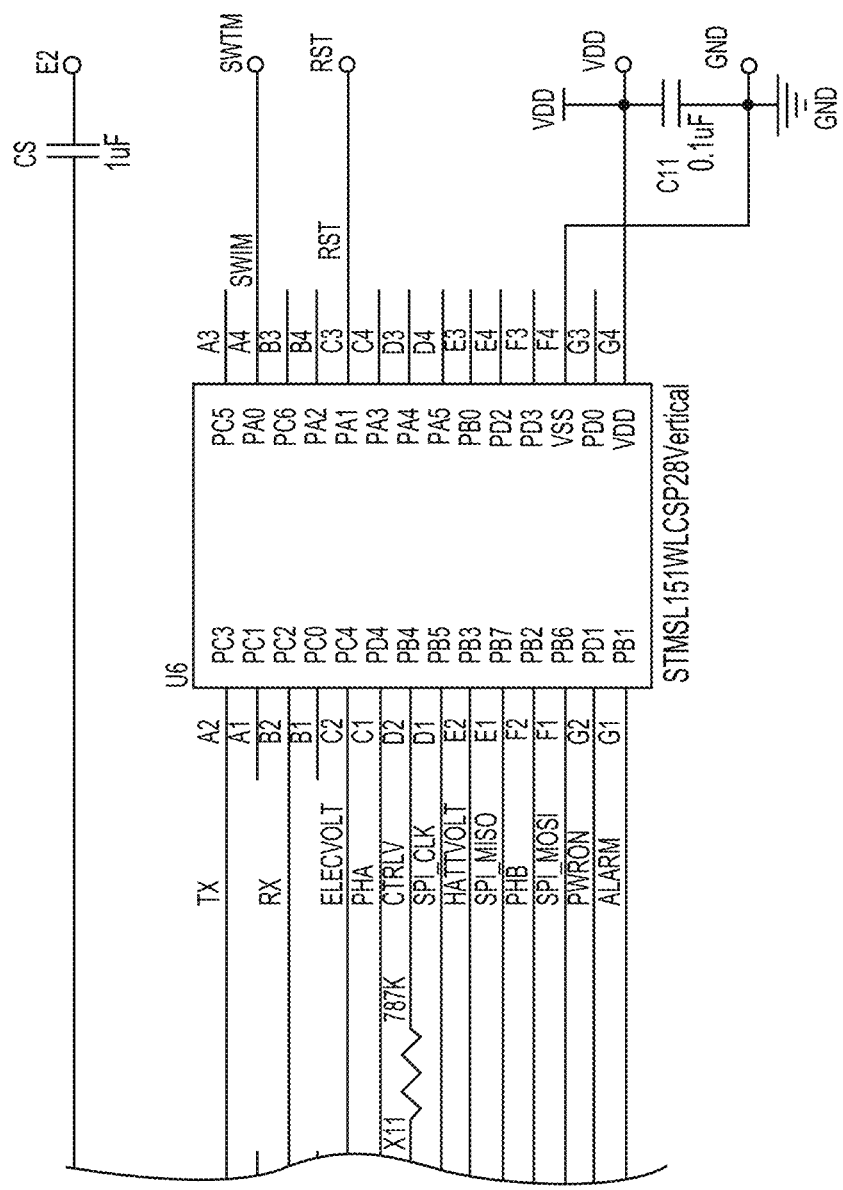

FIG. 14 shows the implant hybrid schematic. The Micro custom integrated circuit along with the MCU performs the functions described in FIG. 12A. D1 and C3 rectify power; D3 is a zener diode that prevents over voltage conditions. D2 demodulates data. R11 sets the scaling from the voltage DAC to the current sinks. C7 and C8 form the H-bridge swing capacitors and provide DC protection. BT1 is the power source and the remaining capacitors are used to stabilize power supply voltages and multiple the voltages.

Figure 17:
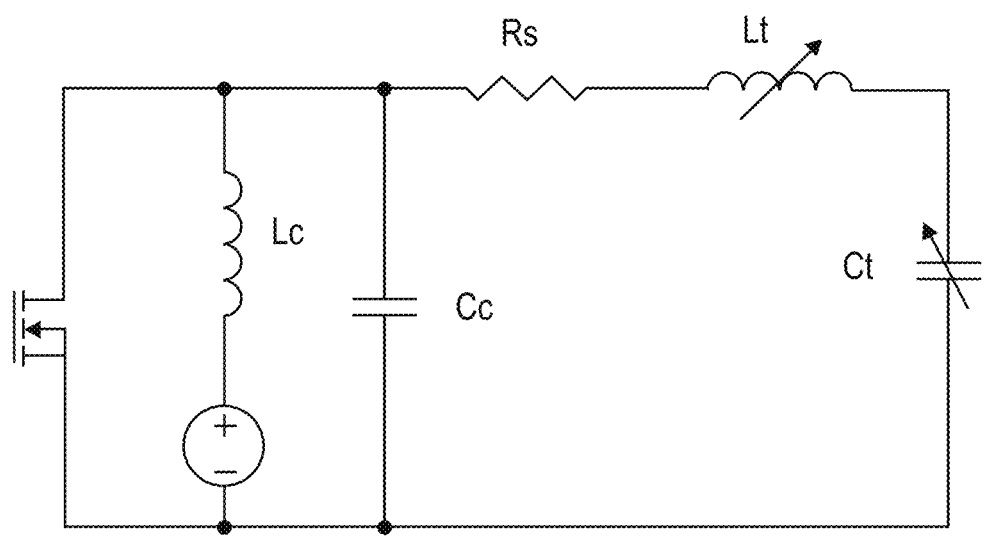
FIG. 17 is one variation of a Class-E amplifier.

FIG. 17 is a Class-E amplifier as used in the Charging circuit. Lt is the transmitting antennae, Lt and Ct form the resonant circuit and Rs is used to reduce Q to the desired value. Ct is adjusted to obtain the proper frequency. Cc compensates for the MOSFET capacitance; Lc forms a constant current source.

Figure 18:
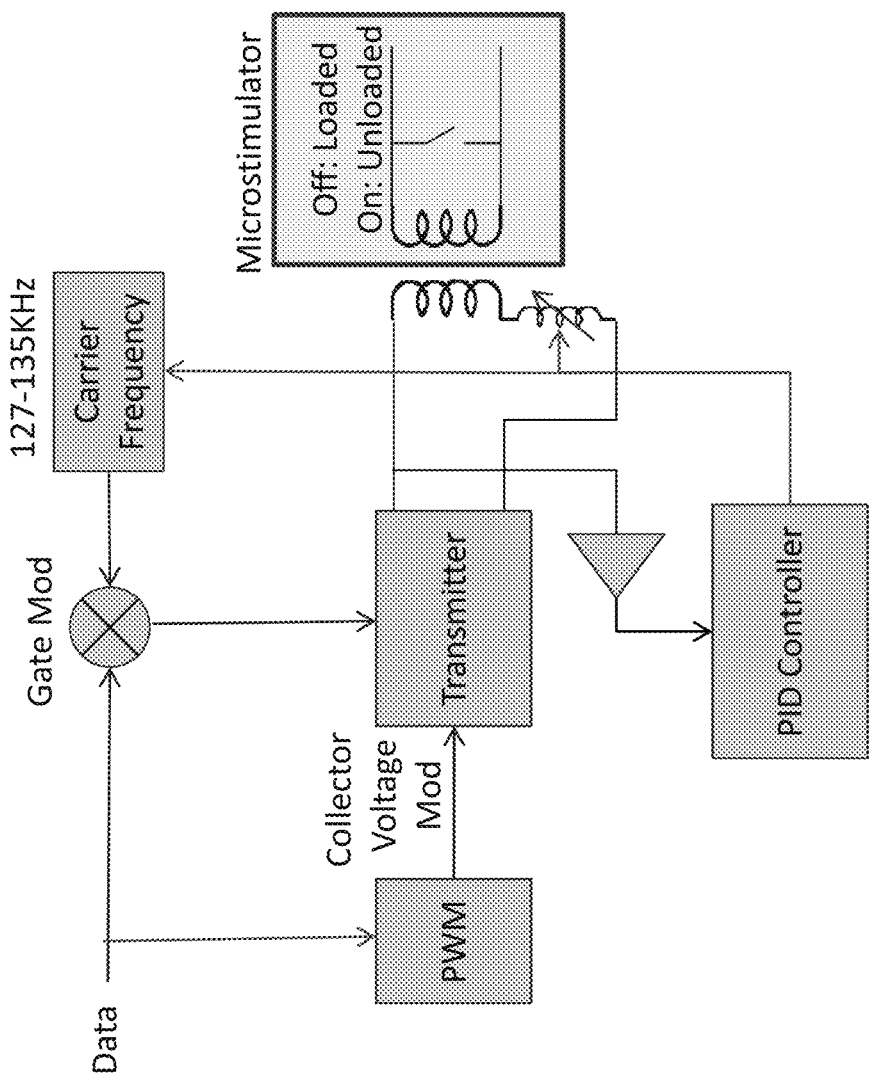
FIG. 18 illustrates one variation of a class E Charger circuit with tuning circuit.

FIG. 18 utilizes a class-D or class-E amplifier in a charging circuit with a second series variable inductor. A PID controller uses the voltage across the two series inductors to control the carrier frequency and the inductance through a DC voltage that in turn varies the static flux in the variable inductor.

Figure 19:
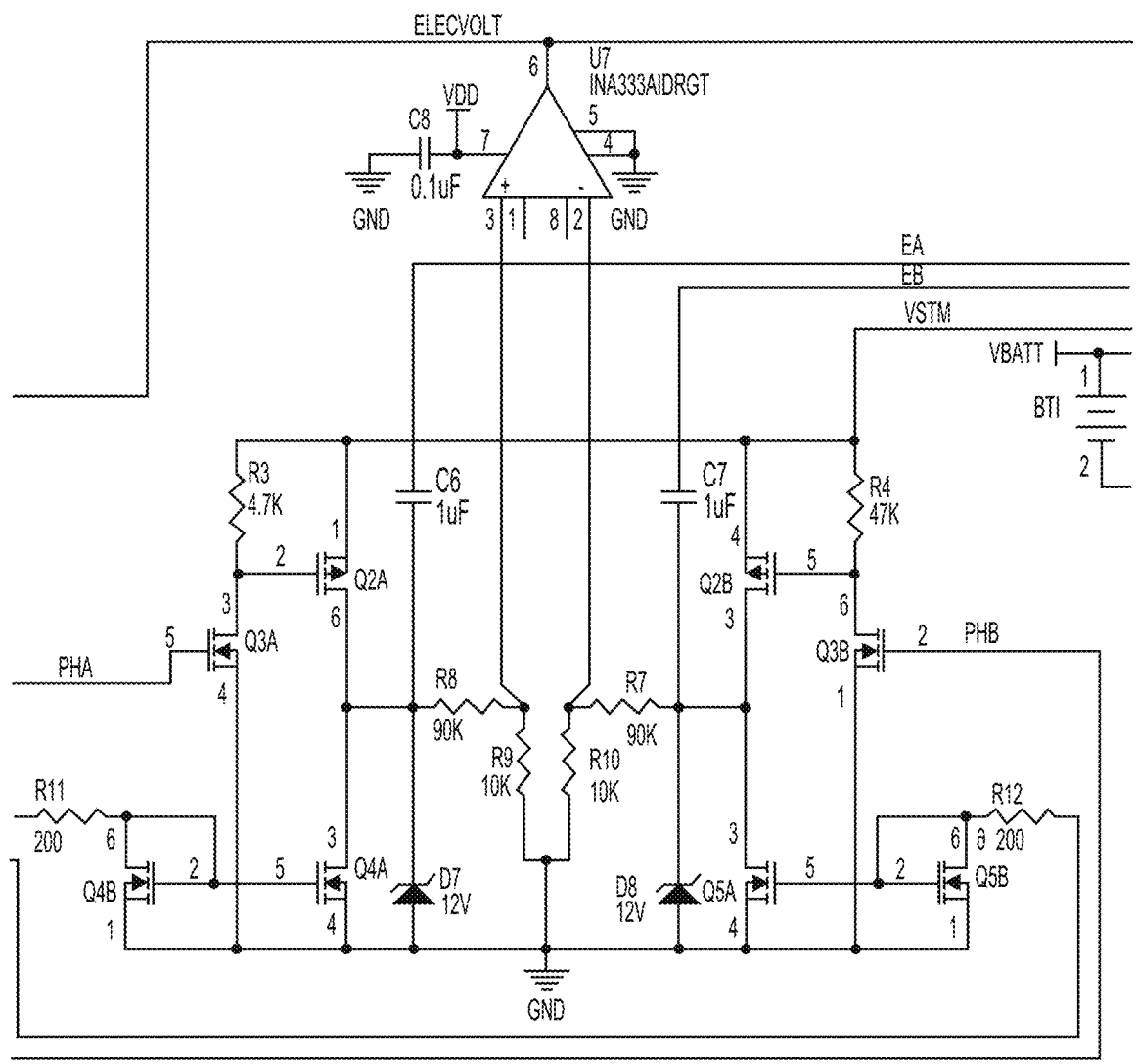
FIG. 19 illustrates one variation of a H-bridge stimulation and measurement circuit.

FIG. 19 is an example of two current sinks implementing an H-bridge bipolar current source. Q4 A&B implements a current mirror that is controlled by a DAC fed through R11. A voltage induced on R11 is converted to a current and is pulled through C6 while simultaneously Q2A is opened allowing current to flow through C7 across an external physiologic load not shown. Q4 and Q2B are shut off. Then the Q5 A&B current mirror is turned on through R12 while Q2A is turned on and the current is reversed through C6 and C7 across the physiological load completing the bipolar pulse. The R8∥R9 and R7∥R10 form voltage dividers that are measured by the differential amplifier (U7). Thus when a specified current is commanded the voltage produced on the differential amplifier indicates the electrode impedance. Also when the voltage gets close to the capability of the supply the system is said to be 'out of the compliance' and the current is not guaranteed. At this point the system can increase the charge by increasing the pulse width or increasing the voltage through the voltage multiplier. R8∥R9 and R7∥R10 also keep C6 and C7 discharged since a charge imbalance will develop due to the mismatch between the Q4 and Q5 current sources.

In many variations, the microstimulators described herein are tunable electrical nerve stimulators configured to deliver modulated electrical stimulus to the vagus nerve of the patient for treatment of inflammatory and autoimmune disorders. The microstimulator, in conjunction with the POD, is intended to perform as a chronic stimulating unit that generates output pulses with defined electrical characteristics to the vagus nerve of a patient. The stimulator is intended for chronic use and may be capable of executing patient specific programs with varying parameters in order to treat a wide array of diseases with differing severity levels.

Figure 3D:
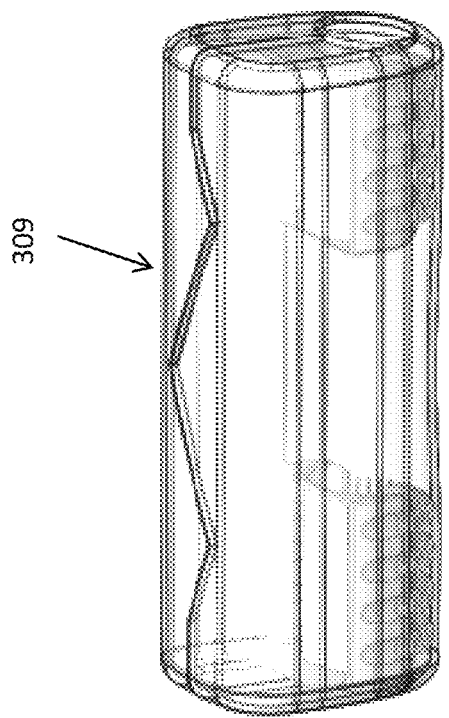
FIG. 3D shows the microstimulator of FIG. 3C within a POD.
Figure 3C:
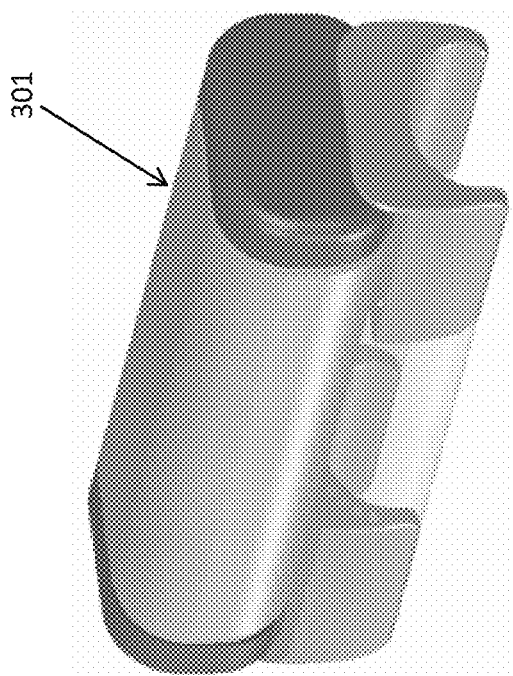
FIG. 3C shows another variation of a microstimulator.
Figure 3E:
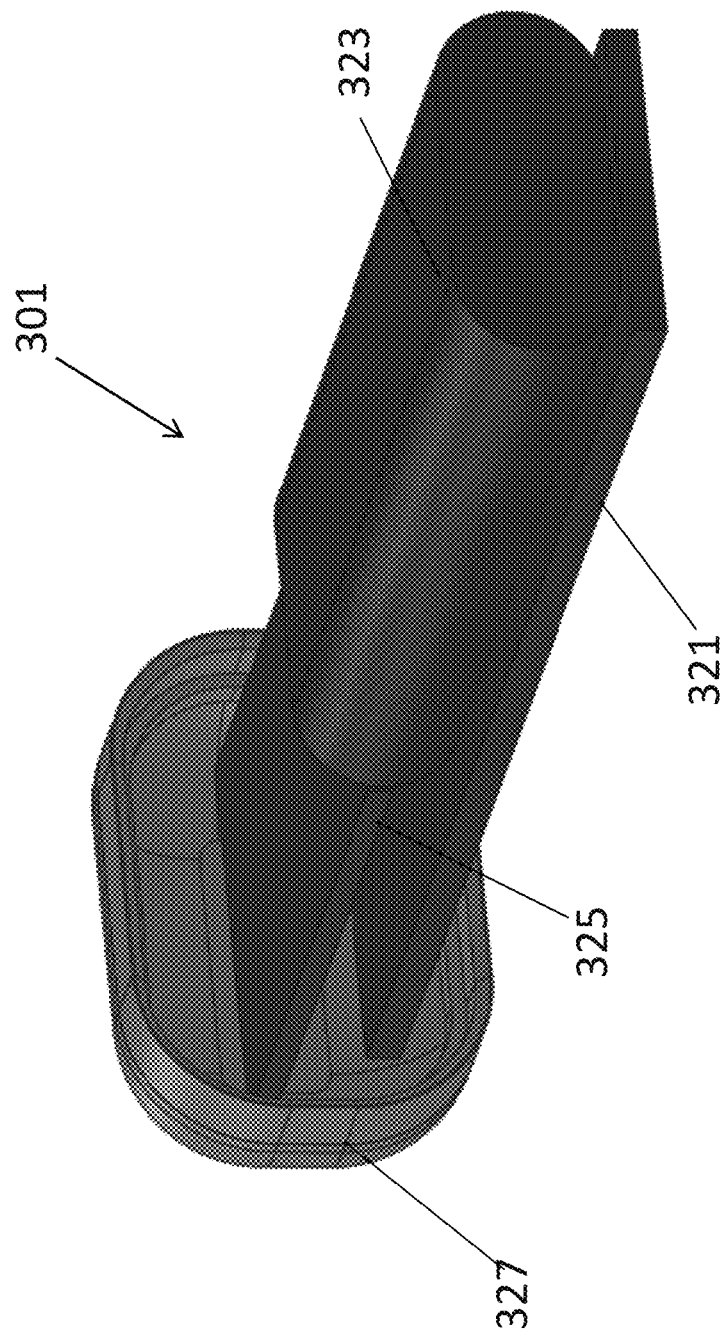
FIG. 3E shows another variation of the microstimulator.

In some variations, including those described above, the microstimulator consists of a ceramic body with hermetically sealed titanium-niobium ends and integral platinum-iridium electrodes attached. The microstimulator may be designed to fit within a POD 309, as shown in FIGS. 3A and 3D. As described above, the POD is a biocompatible polymer with integrated electrodes that may help the microstimulator to function as a leadless cuff electrode. In some variations, such as the variation shown in FIG. 3E, contained within the hermetic space of the microstimulator 301 is an electronic assembly that contains a rechargeable battery 321, solenoid antenna 323, hybrid circuit 325 and electrode contacts (Ti Alloy braze ring and end cap) 327 at each end to make contact with the titanium/platinum case ends.

In general, the microstimulator is designed to be implanted within deep tissue, so that it can be recharged and controlled using an external (e.g., transcutaneous) inductive link through a charger encircling the implant outside the body. One advantage to the microstimulators configured as described herein (including the extremely low duty-cycle of the device) is the low energy requirements of these devices, particularly as compared to prior art devices. For example, Table 6, below illustrates exemplary charging and use profiles for low, typical and maximally used implants. In general, the daily charging duration for low and average patients may be less than 2 minutes/day, and for Maximum patients less than 10 minutes per day.

TABLE 6

Use and charge profiles

| Patient | Full Discharge | Charge Frequency | | |
|---|---|---|---|---|
| | | Daily | Weekly | Monthly |
| Low | 53 days | 0.4 min | 2.6 min | 11.3 min |
| Typical | 50 days | 0.4 min | 2.8 min | 12.0 min |
| Maximum | 5 days | 3.7 min | NA | NA |

Figure 12A:
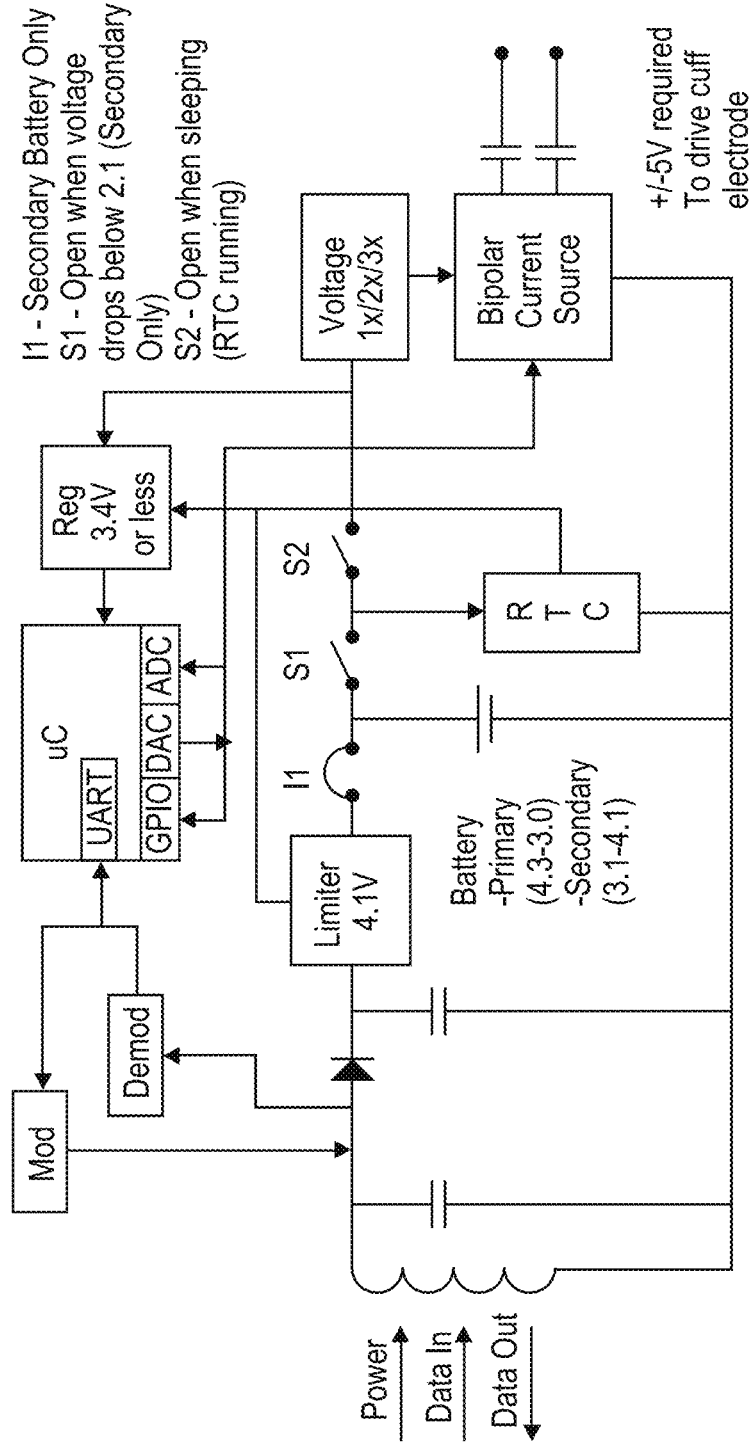
FIGS. 12A and 12B are block schematic circuit diagrams of variations of microstimulators as described herein.
Figure 12B:
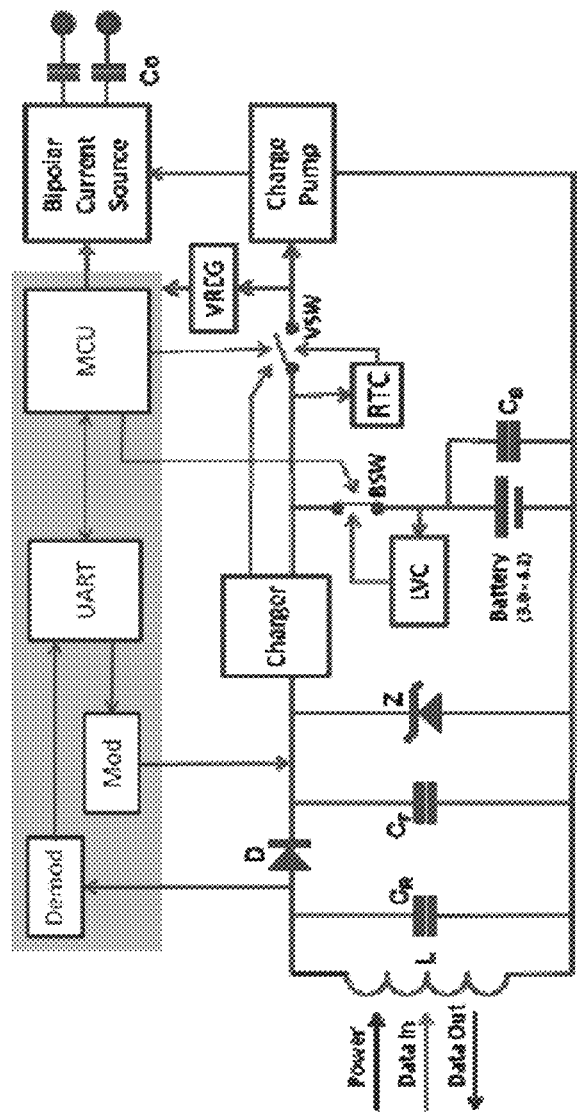
Figure 12C:
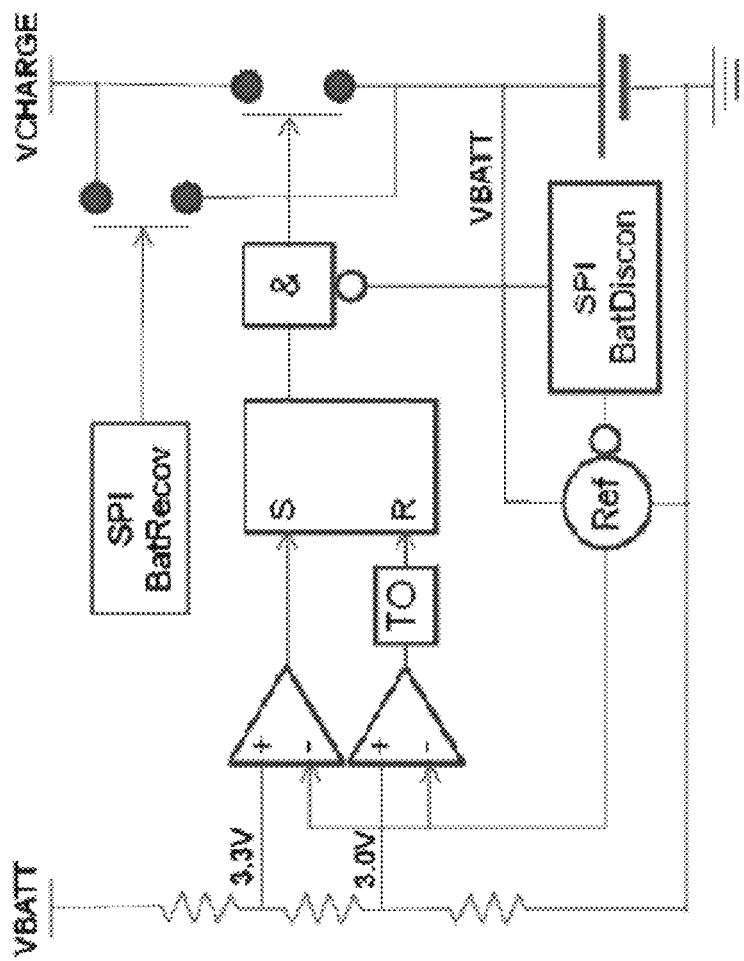
FIGS. 12C and 12D illustrate schematic (circuit) diagrams of a battery switch and a voltage supply switch (VSW), respectively.

FIG. 12B shows another example of one variation of an implant including the following features: resonant antenna circuit (L/Cr) to receive electromagnetic energy from the external Patient Charger; rectifier and filter (D/Cf) to convert energy from AC to DC.; voltage limiter (Z) to protect the circuitry; a secondary battery and brown-out capacitor (B/Cb) to store energy and filter power-on demand current spikes created by high impedance of battery; charger circuit to regulate charging voltage and limit current if the battery fails; real-time-clock (RTC) tracks time and provides wake-up alarms to MCU is always powered if the battery is connected; a communications system to receive amplitude modulated data between the patient charger and microstimulator (Mod/Demod/UART); a charge pump to boost the voltage when required to drive electrodes; a Bipolar current source to drive the electrodes with a constant current biphasic waveform; microcontroller (MCU) coordinates activities both autonomously and while under control of the patient charger and prescription pad; and a battery switch. The Battery Switch typically protects the battery from overdischarge, and may limit the battery usage, as illustrated in FIG. 12C.

For example, when the battery voltage goes below 3.2V for ≥100 mS the battery may be disconnected by the battery switch unless the MCU has overridden the disconnection. Similarly, when the battery voltage wonders above 3.4V the battery may be connected and stays connected until the battery drops below 3.2V. During initial power up the BatDiscon(nect) SPI register may keep the battery and reference voltage disconnected until the MCU enables the battery, which may permit a shelf life in excess of one year. The MCU can at anytime override all of this logic with the SPI register BatRecov(er) that may charge the battery as long as VCHARGE is present. Once the battery has recovered the MCU can release BatDiscon and the system may return to normal operation.

Figure 12D:
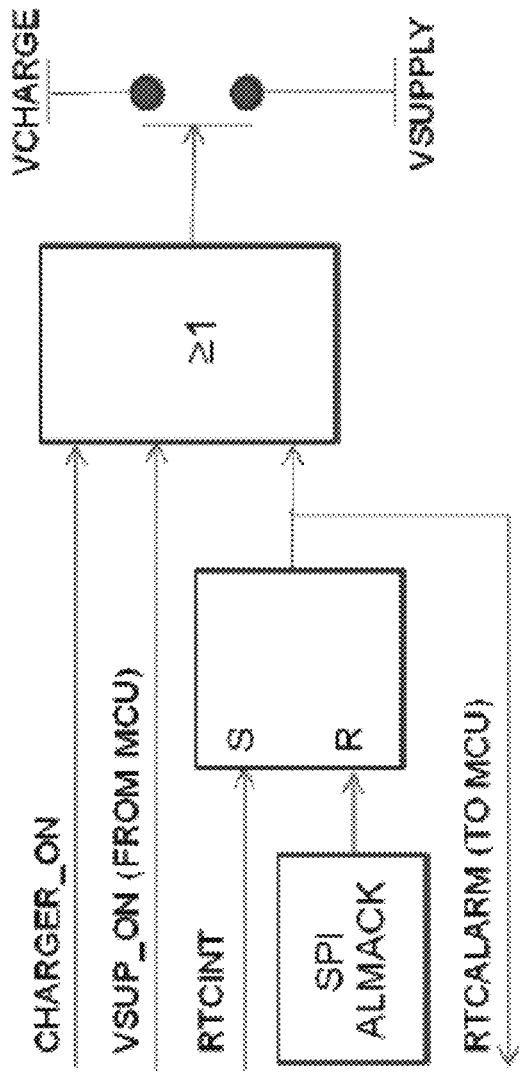

In some variations, the Voltage Supply Switch (VSW) typically turns on the main supply powering up the MCU and peripherals, as illustrated in FIG. 12D. For example, when the patient charger is connected and providing a sufficient electromagnetic force to power up the charger the CHARGER_ON signal is asserted, VCHARGE is energized. Even if the battery is disconnected, and the VSUP (ply) switch is closed; as long as the MCU is powered and holds the VSUP_ON signal the VSW switch is closed. A RTC INT(terupt) pulse is latched enabling the VSUP. The MCU typically receives the latched version of the RTCALARM since: (1) the RTCINT pulse may have turned off by the time the MCU is powered, and (2) an alarm could be missed if the RTC Alarm bit comes in just before the SPI ALMACK(nowlege) bit is reset locking up the system until the next charging session, and (3) the patient charger is removed and the MCU is being shutdown and the RTCALARM occurs such that the interrupt is missed.

Figure 13:
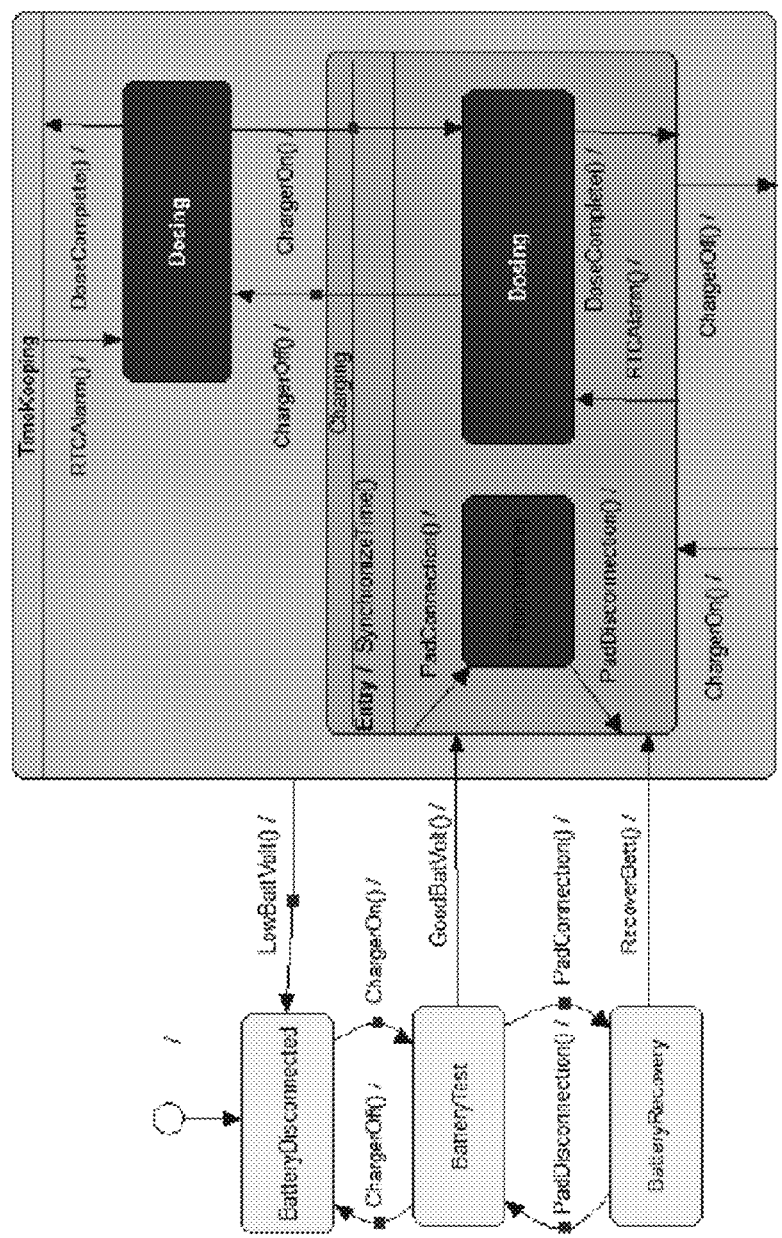
FIG. 13 is a state diagram showing various operational modes possible with a microstimulator as described herein.

Any of the microstimulators described herein may transition through several operating modes as shown in the state diagram in FIG. 13. Modes discussed here are primarily controlled by software, hardware or firmware. Based on this exemplary state diagram, the following states may be enabled: StartState, BatteryDisconnected, BatteryTest, BatteryRecovery, Timekeeping, Charging, Programming and Dosing. In the StartState, the battery may be inserted (e.g., in manufacturing) at 50-75% percent charged. On insertion and power up the system should automatically disable the battery. The BatteryDisconnected state applies when the battery is disconnected whenever the voltage drops below 3.2V. Once the battery is disconnected it may be tested, the BatteryTest state can be entered when the Patient Charger placed within range of the microstimulator. The BatteryTest state may apply once the Patient Charger is powering the microstimulator the battery can be tested. However, to enter the BatteryRecovery state, the Prescription Pad may be connected to the patient charger. In the BatteryRecovery state, the MCU may be commanded by a clinician to recover the battery. Once the recovery process is started the microstimulator enters the Charging state. If the Patient Programmer is removed before the battery charges to 3.4V the hardware may disconnect the battery.

The TimeKeeping state applies while the battery is connected. The system is therefore always tracking time. After the battery is installed the time tracking may start counting at zero. By convention, this start date/time may be based on Jan. 1, 2000, 12:00 Midnight (though any appropriate date/time may be used). The correct time may not be available until the Charging state is entered. The Charging state applies when the Patient Charger is sufficiently close to the microstimulator, the charging circuit is energized and the Charging state is entered. Upon entry to this state the real-time-clock in the microstimulator is synchronized to the crystal controlled time base in the patient charger. Two sub-states are possible while in the Charging state: Programming and Dosing states. The Programming state occurs when the external controller (e.g., a prescription pad) is connected the Patient Charger the Clinician can program, maintain, and diagnose the microstimulator. In the Programming state Dosing may be disabled, however the patient can be stimulated with Test Stimulus through the Prescription Pad. Once the Prescription Pad is disconnected Dosing may resume.

The Dosing state is typically entered through an RTC Alarm. RTC Alarms can occur while in the Charging state or while the microstimulator is in the TimeKeeping state. The Dosing state may start stimulating the patient for the allocated time and then exit back into Timekeeping mode if the Patient Charger is not present or fall back into the Charging state. Note that the Charging state can be entered while in the Dosing state, there are no differences between the two Dosing states.

Figure 21A:
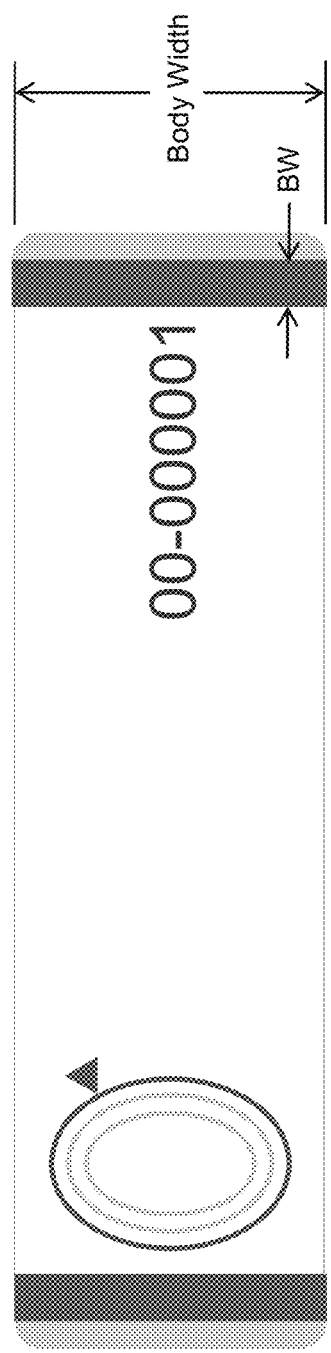
FIGS. 21A-C illustrate one variation of a microstimulator, including exemplary dimensions.
Figure 21B:
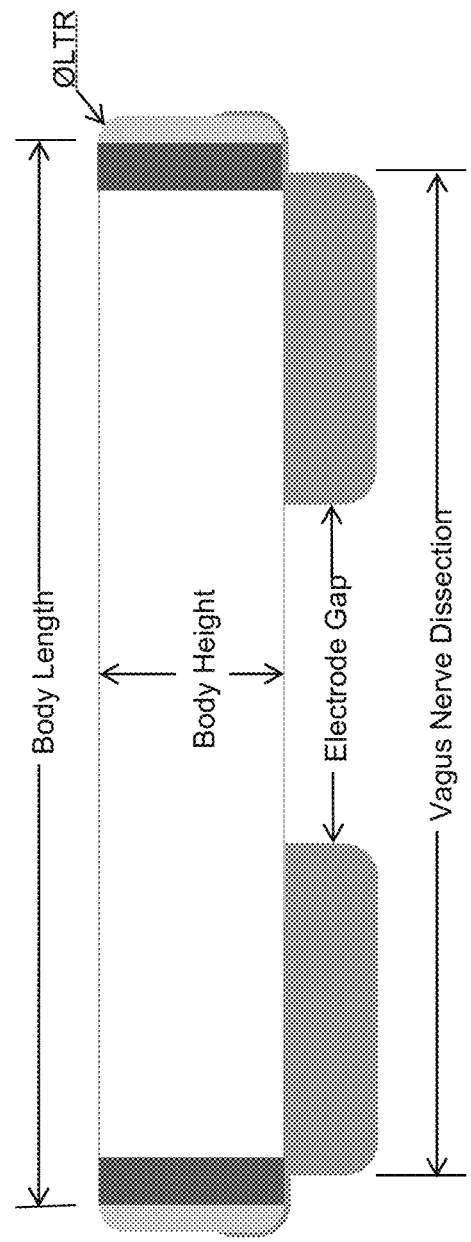
Figure 21C:
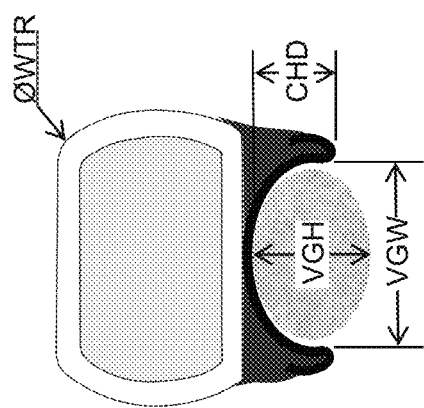

The microstimulator may be hermetically sealed by laser welding in a dry helium argon environment with an integrated bake-out laser welding system. As mentioned above, different sizes of microstimulators may be provided to accommodate different size patient nerves. For example, three versions of the microstimulator may be made available to accommodate the different vagus nerve sizes. Overall, the weight of the device is set to have a similar density to water. In some variations the microstimulator may be coated with a non-stick coating such as Teflon to avoid long term adhesion to the POD. Specific mechanical dimensions of the microstimulator are illustrated in the diagram of FIGS. 21A-C. With reference to FIGS. 21A-C, Table 7 (below) illustrates exemplary size variations of the one embodiment of a microstimulator as described. The dimensions and ranges for each dimension are exemplary only.

TABLE 7

| Designator | Explanation | Minimum | Maximum |
|---|---|---|---|
| Body Length | Minimize Incision | | 20 mm |
| Body Width | Minimize Displacement | 6.05 mm | 6.15 mm |
| Body Height | Minimize Displacement | | |
| BW | Bandwidth to reduce conductive shadow seen by the charging field may be minimized to reduce energy loss and heating. The surface of the device in contact with any tissue cannot exceed a temperature of 2° C. higher than the surrounding tissue. Heating of conductive metal in the shadow can be reduced by increasing resistance (e.g. Ti 6-4) and thinning material. | | |
| LTR | Length Transition Radius - maximized to smooth transition against vasculature and muscles | | |
| Vagus Nerve Dissection | Minimized to reduce the length of required dissection | | 18 mm |
| Electrode Gap | Gap required to stimulate the nerve efficiently across mylenated fibers | 7.5 mm | 8 mm |
| WTR | Width transition radius should be maximized to smooth transition against vasculature and muscles | | |
| VGW | Vagus Nerve Width should accommodate three sizes | 2,3,4 mm | |
| VGH | Assumed to be about 75% of VGW | | |

TABLE 7-continued

| Designator | Explanation | Minimum | Maximum |
|---|---|---|---|
| CHD | Channel depth should be maximized to contact as much of the nerve as possible and assure that it does not slip off nerve. | | |

In the exemplary embodiment shown in FIG. 21A, for example, the concentric circles on the left, highlighting the outer circle, indicate that this variation corresponds to the largest size of implant, and the numerical/alphanumerical marking on the far right may provide a unique identifier for the implant.

In some variations, a large silicon die may be moved to the ends of the microstimulator as far away from the center of the coil as possible. The electronic Assembly may use a hybrid that may support approximately 4 signal layers. The ASIC may be wire bonded bare die.

The power source may be a battery or other power storage device, typically having a capacity of 200 μA, and an average drain of 100 μA or less when the circuit is active. Standby drain may be less than 50 nA. The charge time at 37° C. may be less than 20 minutes to achieve 75% of capacity at a 1 mA (5 C) charge current. The maximum current into battery during short circuit failure is typically <5 mA. In some variations, the size of the battery is ≤0.65 mm thick×≤7.5 mm long×≤4.8 mm wide. In another variation, the battery is <0.4 mm×18 mm×4 mm; in a third embodiment, the battery is <0.4 mm×25.4 mm×4 mm. In general, the battery may have two silver palladium terminals or equivalent that may allow soldering, resistance welding, or silver epoxy to ceramic substrate and be <1.5 mm wide by >2 mm long. Furthermore, the battery may be capable of >1 mA peak discharge current, and may be sealed with an aluminum foil 16 microns thick that may allow storage in air for up to 1 year. In some variations the preferred chemistry of the battery is Lithium Phosphorus Oxynitride (LiPON) with a LiCoO2 cathode and Lithium anode. For example, the battery may have an internal resistance that may be <300Ω (Normal Minimum Operating Voltage (3.6−1 mA*300Ω=3.3 V minimum operating voltage). The Low voltage cutoff may be ≤3.0V, the self discharge <20% per year; capacity Loss may be <20% over 300 cycles.

As described above, any of the microstimulators may typically include one or more antenna for communicating with a controller and/or charger. The dimensions of the antenna may be, in various examples, approximately: <1.5 mm thick×<12 mm long×<4.8 mm wide; <2 mm×<10 mm×<4.5 mm; <2 mm dia×18 mm long; and <2 mm dia×25 mm long. The construction may be ferrite with a design to minimize the MRI imaging artifact. The antenna may be able to produce 5 mW at a voltage of at least 2 volts.

The electrode of the microstimulator may provide a nerve contact area equal to approximately ½ the surface area of the nerve for at least a length of 5 mm. Minimum electrode area=2 mm (min vagus diameter)×π×5 mm (min length)×½ circumference=15 mm2. For example, a vagus nerve diameter of 2-4 mm may be supported. In combination with the POD, less than 1 mm of total gap may be allowed around the vagus, indicating three sizes or adjustable electrodes. The bipolar Impedances of the electrodes may be less than 1000 ohms (real component).

Figure 22:
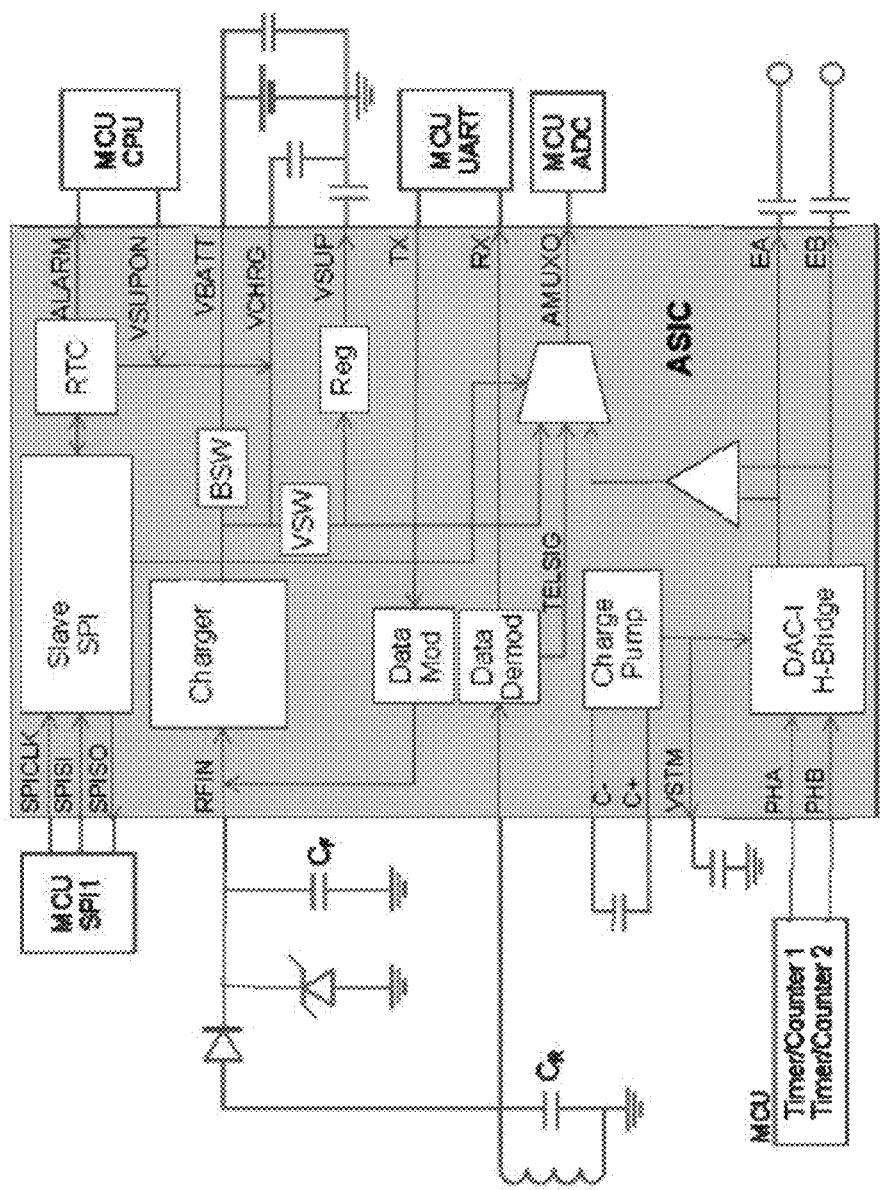
FIG. 22 shows a schematic of one variation of an ASIC for use in the microstimulator.

In some variations (such as the variation illustrated above in FIG. 3E), the microstimulator may be implemented on a multi-chip hybrid substrate and consist of the following components: Microcontroller, Application Specific Integrated Circuit (ASIC), LiPON Rechargeable Battery, and various discrete components. The functional partitioning and specifications is shown in FIG. 22. In this example, the MCU (e.g., a STM8L151 Micro Controller Unit or MCU) in a chip scale package may be used. The CPU may clock at least as fast as 1 MHz during required CPU intensive operations and during Patient Charger operations. The clock may be calibrated to with ±1% over life. The MCU may have a low power low frequency clock to drive timer/counters of at least 10 KHz to time periods between biphasic stimulation pulses. Non volatile memory may contain at least 16 KB program and data may withstand 10,000 write cycles with a retention time of 20 years. At least 1 KB of very high usage EEPROM may be available for writing parameters such as exception logs. A UART Asynchronous Receiver/Transmitter is set to receive and transmit a maximum of 4800 baud and the frame may be configured as follows: 1 start bit, 8 data bits, and one stop bit. The UART may have the ability to detect overruns, noise, frame, and parity errors. The 8 data bits may be encoded using 6b/8b encoding to maintain ASIC approximate DC balance. The Analog Digital Converter (ADC) may have the ability to detect a 0.5% change in field strength (0-50V), Battery Voltage (0-4.5V), Voltage across Electrode contacts 0-20 V and a 0.1% change in temperature from the interface MCU sensor. In this example, two timer/counters may be used to generate timing pulses for bipolar current source with an accuracy of (±5%) and 25 uS increments between 0-1000 uS.

The ASIC may include an RTC that is implemented with an ultralow power oscillator, counter, and comparator. A semiconductor junction may provide a voltage reference to drive a low frequency oscillator stabilized by body temperature. This oscillator may clock a 40 bit register that may track absolute time for a period of at least 200 years. A comparator may generate an RTC Alarm pulse when a match occurs. The counter is intended to be corrected with a read and write each time the system is charged. The RTC and the BSW together may operate with <50 nA. The clock frequency may be 128±64 Hz with a drift less than ±0.25% over an entire day in a 37° C. controlled environment. The frequency may be able to be calibrated to ±0.1% within 30 seconds (100/(64 Hz*30 seconds) 0.05%. The oscillator may run at a higher rate than once per minute and be divided down. The MCU may have the calibration constant programmed in at manufacturing time and may write the adjusted number of 'ticks' to the ASIC RTC. The 48 bit counter may be read/write through the SPI port and double buffered to reduce software complexity. A 48 bit comparator register may generate a RTC-Alarm pulse that is routed to the Voltage Supply Switch. The comparator may be double buffered and be read/write through the SPI port.

The Charger shown in FIG. 22 includes a charger circuit that may consist of a voltage booster followed by a linear regulator that may accept a range of 2-7 volts and convert it to 4.05-4.18 volts with a maximum current limit of 5 mA. In addition, the device may include a BSW. The Battery switch functionality was described above (in reference to FIG. 12C). The battery switch may include a power of the BSW and RTC that is <50 nA. When the battery is disconnected the power may be <15 nA. The battery may be disconnected from the VCHARGE line when the battery voltage drops below 3.3V±10% for some time value (e.g., on the mS scale). The battery may be reconnected when the battery voltage rises above 3.4V±10% for some time (on the mS scale). Demod/Mod Communications are enabled through a combination of a RS-232 port on the MCU and a modulator and demodulator pair in the ASIC. In order for proper Demod/Mod operation the following rules may be applied: bits may be alternated so that no more than two bits of the same polarity may be in sequence. This maintains the required balance for slicing the data; data may be grouped in packets and a two word preamble may be required; packets may be checked with a CRC code before the data is utilized (also alternating bit violations would required packet rejection); a data stream may be recovered by an amplitude shift keying demodulator may have a rectifier followed by a single pole low pass filter at 2× the 4800 bps baud rate and limit the voltage to Vsupply; the data slicer may compare the data stream to a long term envelope of the data (the envelope may consist of a low pass filter with a cut-off at about symbol length (10 bits) or 480 Hz); the data modulator may load the resonant coil with a predetermined resistance; and the data modulator may utilize a snubber to minimize the resulting spectral splatter.

As illustrated in FIG. 22, the Vsupply Regulator may help keep the MCU voltage regulated and >2.0V and <3.3V and can be turned on by RTC, and held on by RTC and/or MCU. The Charge Pump provides a 2× voltage multiplier that doubles battery voltage that supports an equivalent load of 100KΩ and a peak load of 5 mA and a peak average load of 0.5 mA using 10,000 pF capacitors. The DAC is an 8 bit current mode DAC that drives one of two current mirrors (sink configuration) to produces a 0-5,100 uA±5% in 20 uA steps. The DAC may have a full scale settling time of <1 uS to a resolution of 6 bits. Calibration may be supported in manufacturing at the system level using data that is either store in MCU or ASIC. The Bipolar Current Source in the variation is an H-bridge push pull configuration that may be used to drive bipolar electrode. Two anodic switches and two cathodic current sources are a possible configuration. Capacitive coupling using high quality discrete ceramic capacitors is required to double voltage swing and prevent DC flow out hermetic capsule. Discharge resistors of 100 KΩ±30% are required to drain resulting voltage offset that builds up between output capacitors and H-bridge. In this example, an analog multiplexer having voltage measurement facility measures: battery voltage (1 s sample rate); Demod signal strength (1 mS sample rate), and a differential amplifier for measuring voltage across electrode (25 uS sample rate). Factory calibration of each of the three values may be supported with both slope and offset and stored in the MCU EEPROM. The implant may also include a version number, such that the silicon version number is accessible through SPI port. The format may be one byte sequential indicating design mask submission. The example in FIG. 22 also shows a Zener that provides overvoltage protection from electromagnetic fields using a Zener voltage clamp <6 V (a higher level may result in less power dissipation in Microstimulator) with a minimum power dissipation capacity of ½ watt (which may set upper limit based upon semiconductor process and Charger circuit optimization). DC Protection may be provided by output capacitors to prevent DC leakage in excess of 50 nA independent of any software or circuit failures. Capacitors may be at least 47 nF. The MCU—Watchdog timer runs when MCU runs to restart processor in case of software hang-ups.

Example 1: Microstimulator

Figure 23A:
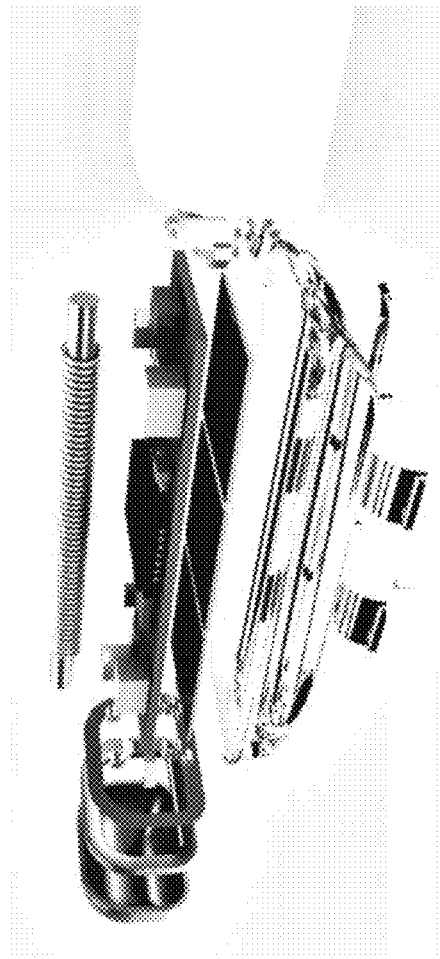
FIGS. 23A and 23B illustrate another variation of a microstimulator as described herein.
Figure 23B:
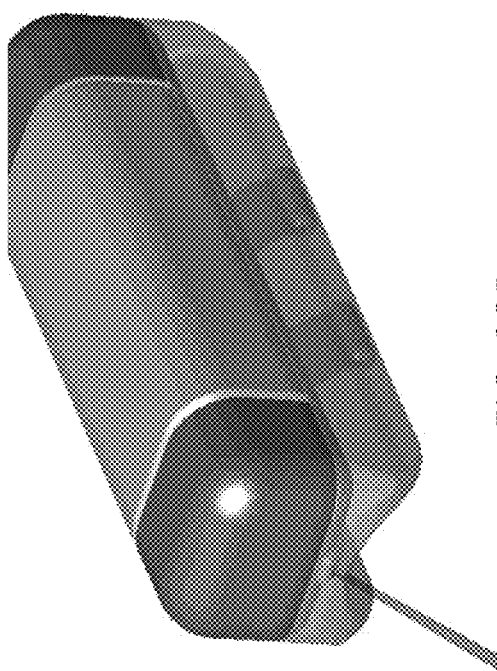

In this example, the microstimulator is a rechargeable neural stimulator that attaches to the vagus nerve and delivers current through bipolar platinum contacts against the nerve, as illustrated in FIG. 1B (103). The microstimulator battery may be charged by an external charger ("energizer") and the energizer also functions as the communication gateway for the external controller ("prescription pad"). The Microstimulator in this example is physically housed in a rigid hermetic capsule with an attached electrode saddle. The hermetic capsule in this example is composed of an Alumina toughened Zirconia tube with metal ends brazed onto the ceramic tube. Brazing joints may use a nickel diffusion process or gold braze. The metal ends are an alloy of Titanium to reduce electrical conductivity and increase braze-ability. As shown in FIG. 23A, within the hermetic capsule is a resonator, hybrid with attached electronic parts, and batteries. The hybrid assembly is suspended by metal clips that also make contact to the metal ends. The electrodes are molded into a polymer saddle and electrical contact is made to the metal ends with a laser weld.

Figure 24A:
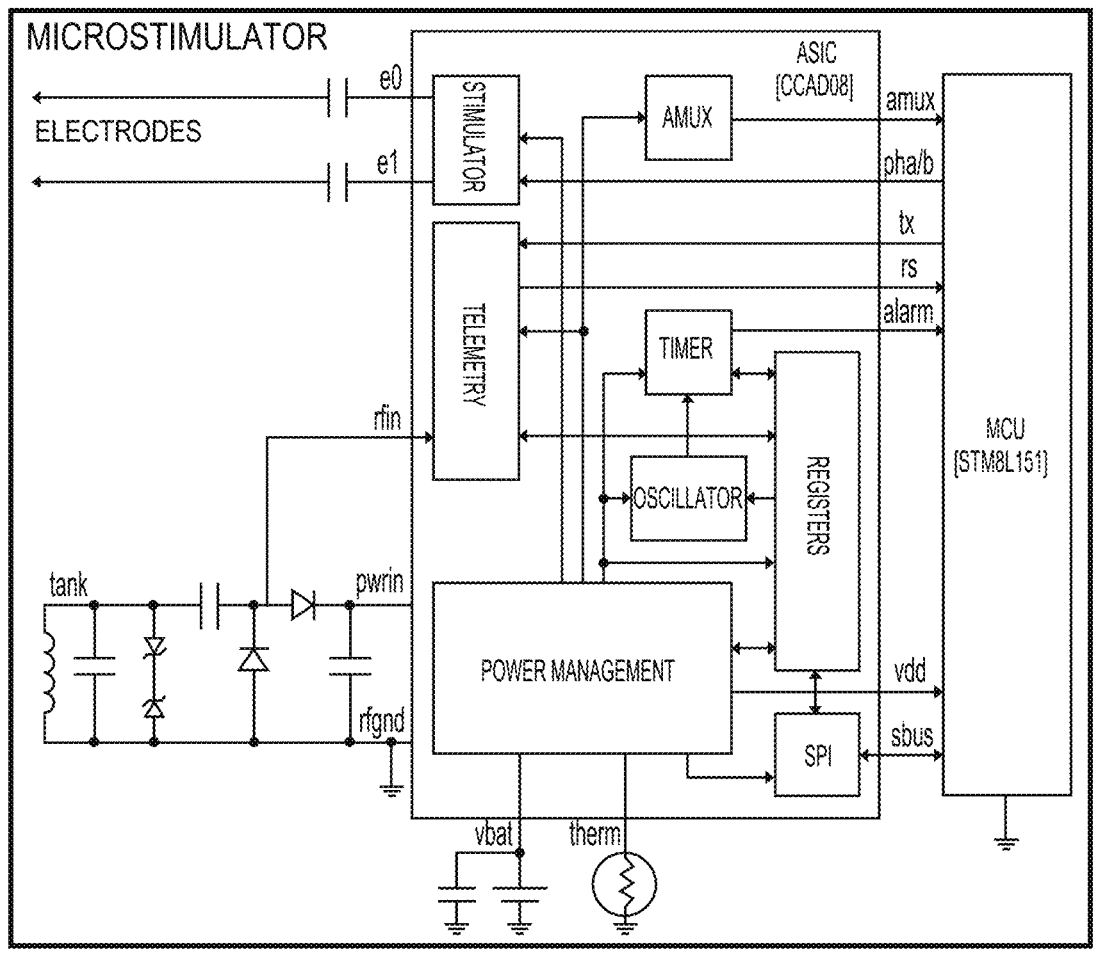
FIG. 24A shows a schematic block diagram of the microstimulator of FIG. 23A.
Figure 24B:
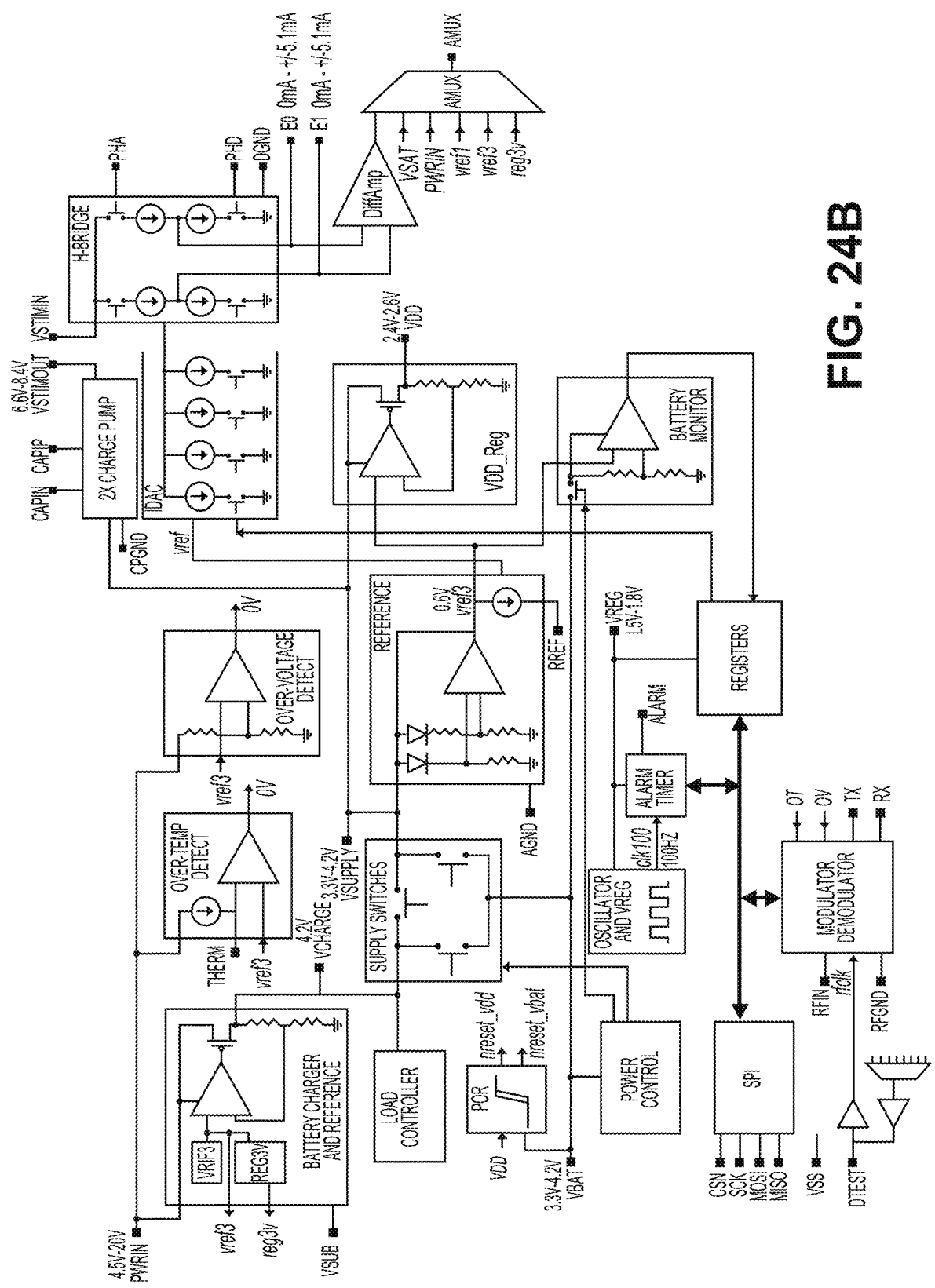
FIG. 24B shows a block diagram of the ASIC of FIG. 24A.

The active electronics in this variation of a microcontroller consist of a custom ASIC (CCAD08) along with a MCU (STM8L152) show in the block diagram in FIG. 24A. FIG. 24B shows a block diagram of the ASIC. The passive electronics of the microcontroller consist of a resonator, zener over voltage protection diodes, voltage doubling diodes, and filtering capacitors. The electrodes have in-line blocking capacitors to prevent DC flow. A thermistor shuts the device down in over temperature conditions. And finally a battery provides power to the system. Referring to the block diagram in FIG. 24A, the system operates as follows. Power is received by the resonator. A rectified AC coupled version of the TANK voltage (RFIN) is sent to the telemetry circuit where telemetry data amplitude modulated on the carrier is detected and demodulated. RFIN also feeds through another rectifier that doubles the voltage at PWRIN.

The Power Management circuitry has many functions. The first function is to regulate the voltage to charge the battery as this voltage needs to be controlled within a few tens of millivolts to maximize the capacity of the battery without damage. Supply switches supply the ASIC and MCU external power even if the battery is damaged or not present allowing functions such as battery recovery, initial battery charging and diagnostics. A VDD regulator reduces the battery voltage to 2.5V so that MCU will not be damaged and provides a reference for the MCU analog to digital convertor so that impedances can be measured accurately. Supply switches also route battery power to the MCU when the Microstimulator is running autonomously (no Energizer Present) which is the normal mode of operation. Voltage comparators that are calibrated in manufacturing protect the battery from over discharge by first shutting off all functions other than time keeping and finally putting the device in shelf mode until the battery is charged. Voltage comparators short the tank out when either an over-temperature or over-voltage condition is present protecting the device. A load stabilization circuit produces a constant load of 0, 1, 2, or 3 mA stabilizing the load to improve the robustness of communication. Turing on the ADC in the MCU can for instance increase the load from 200 uA to 1 mA. Two voltage references are generated, one that operates when charging, the other that operates when the battery levels are periodically checked. A power on reset assures that when the system is powered during manufacturing or when the MCU is powered after an Alarm event that the logic operates without errors.

The Telemetry sub-system extracts a clock from the carrier for Manchester decoding, extracts the envelope or the carrier for data detection. Then it slices the analog signal to derive binary data. This binary data with the extracted carrier clock is used to convert the Manchester encoded data to NRZ format that can be interpreted by the UART in the MCU. The UART set to the same baud rate is able to translate the asynchronous stream to 8 bit systems. The Manchester encoder must be programmed for either a 1200 or 4800 baud rate by the MCU.

Back Telemetry data, that is data from the Microstimulator to the Energizer, is kept in NRZ format. This data is always sent as a response to an Energizer packet. The UART data causes a load shift keying (LSK) modulator to short RFIN to ground effectively unloading the Microstimulator from the Energizer coil. In order for the Energizer to receive this data is must continue to send an unmodulated carrier to the Microstimulator.

The Oscillator block in the ASIC is an extremely low power RC circuit (<50 nA). It is body temperature stabilized and driven by a regulated voltage supply. The clock is further calibrated during the manufacturing process. The oscillator drives a 40 bit counter at 100 Hz configured as a timer. The Timer has a programmable ALARM that powers-up the MCU with the wakeup time configured by the MCU. Power is preserved by only running this timer and then powering up the system/MCU for scheduled activities. A typical activity is dosing the patient with stimulation using the Stimulator block, usually about once per day. This oscillator is only accurate to about +/-3 minutes a day so it when the Energizer is attached the Timer time is adjusted to the very accurate Energizer time.

Another function the timer has is to command the circuitry to check the battery level about once per hour as continuous checking would require too much power.

The Stimulator block has contains an 8 bit current DAC configured as an H-bridge enabling generation of balanced biphasic pulses and the stimulation voltage and inverted stimulation voltage. The stimulation voltage is generated from a 2x voltage multiplier defining the stimulation compliance rail. Also included in this block is a differential amplifier that measures the voltage across the complex physiological load. And at a constant current the voltage waveform measures is proportional to the complex impedance. If the voltage hits the compliance rail the stimulation is no longer delivering a constant current, a condition to be avoided.

The MCU controls the ASIC through the SPI accessible Registers. Through these registers the MCU drives the stimulator digital-to-analog convert to stimulate the patient for a particular duration. The MCU also has access to many voltages on the ASIC through the Analog Multiplexer (AMUX).

Very accurate settings are required to not only mark time but also manage the battery. The strategy for managing the significant variations in silicon is to utilize numerous calibration Digital-to-Analog convertors implemented in the ASIC to adjust all the voltage and frequency references. This process is done using calibrated test equipment in manufacturing and then stores these values ors in MCU EEPROM. These values are stored in the SPI registers in the ASIC, typically power is never removed, but it is these values can be refreshed by the MCU.

Figure 15:
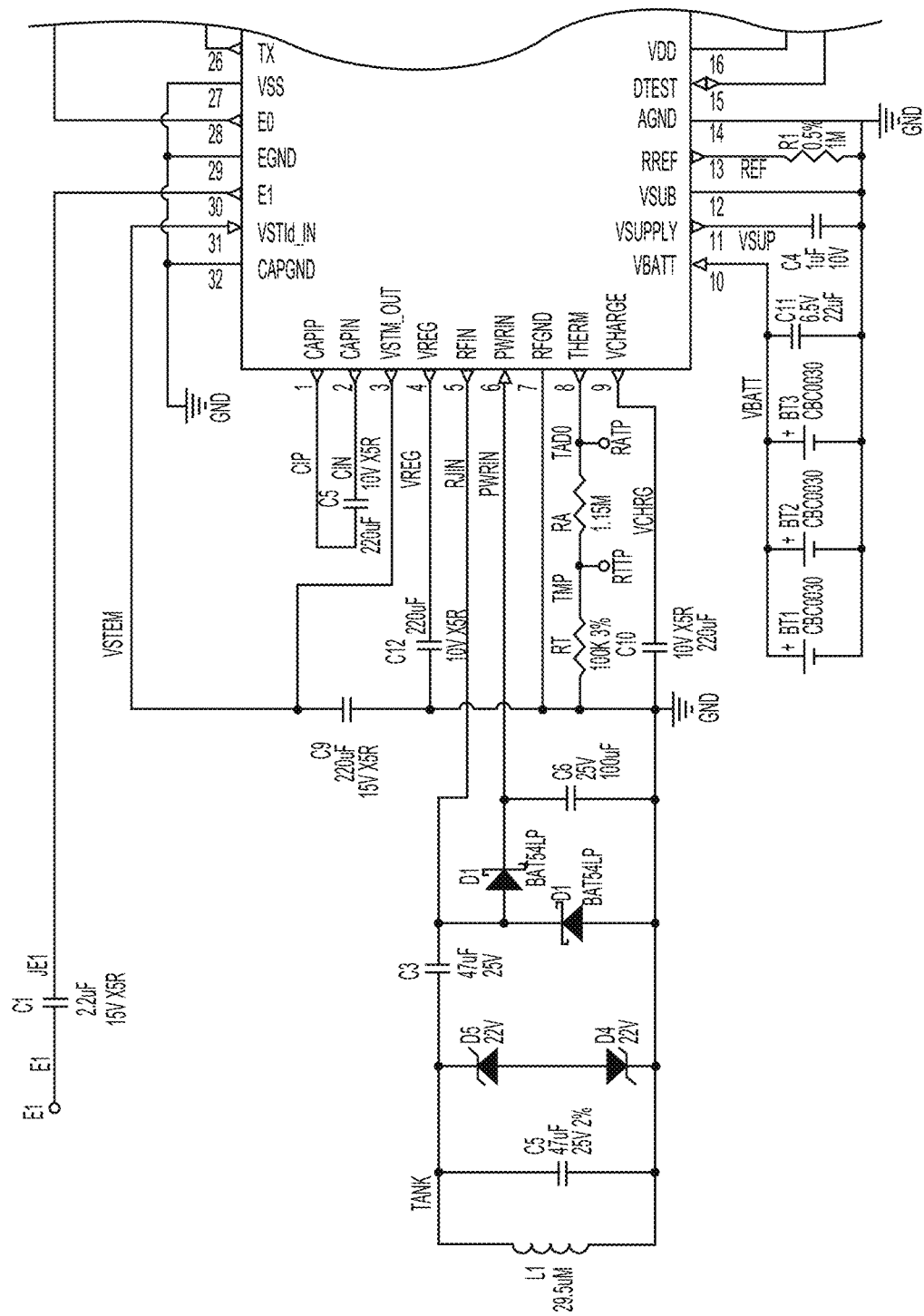
FIG. 15 is a system schematic for a microstimulator as described in one example herein.
Figure 15:
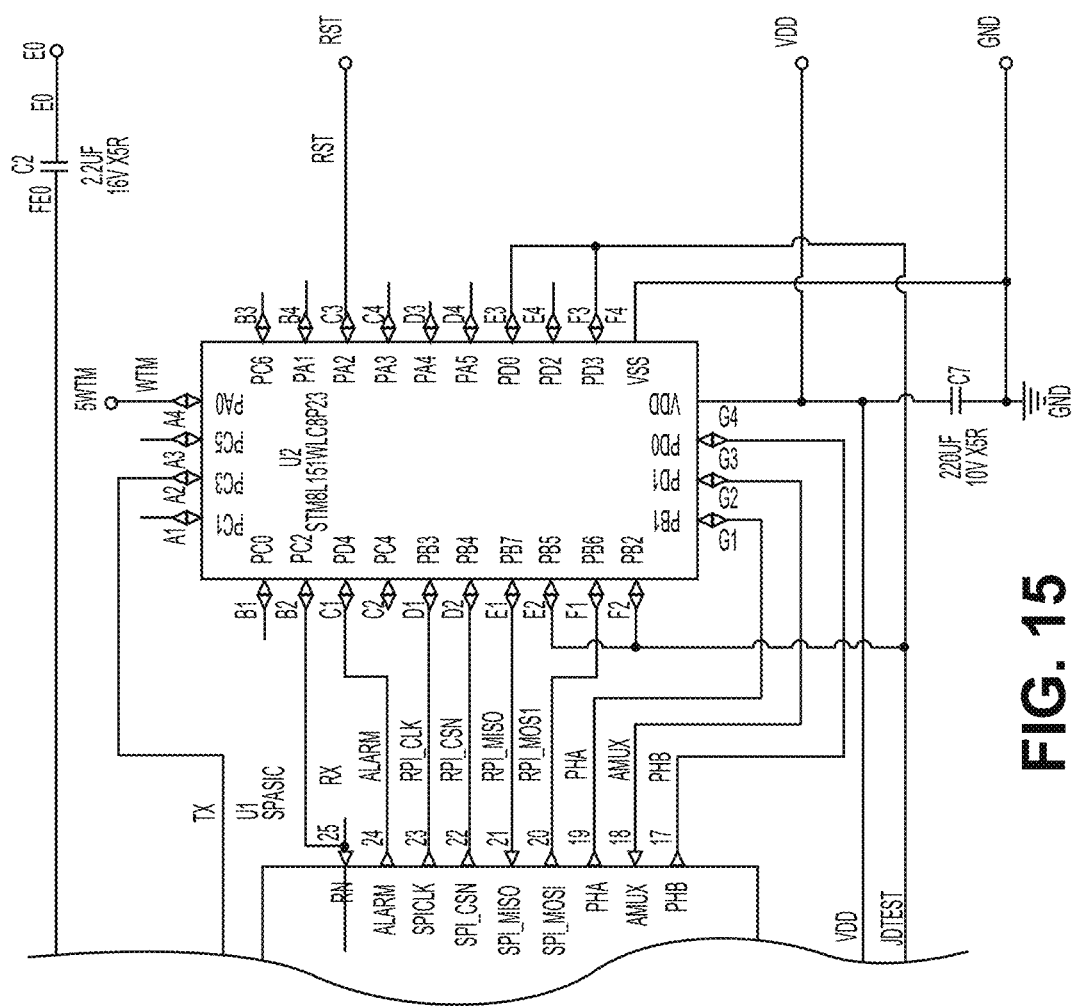
Figure 16:
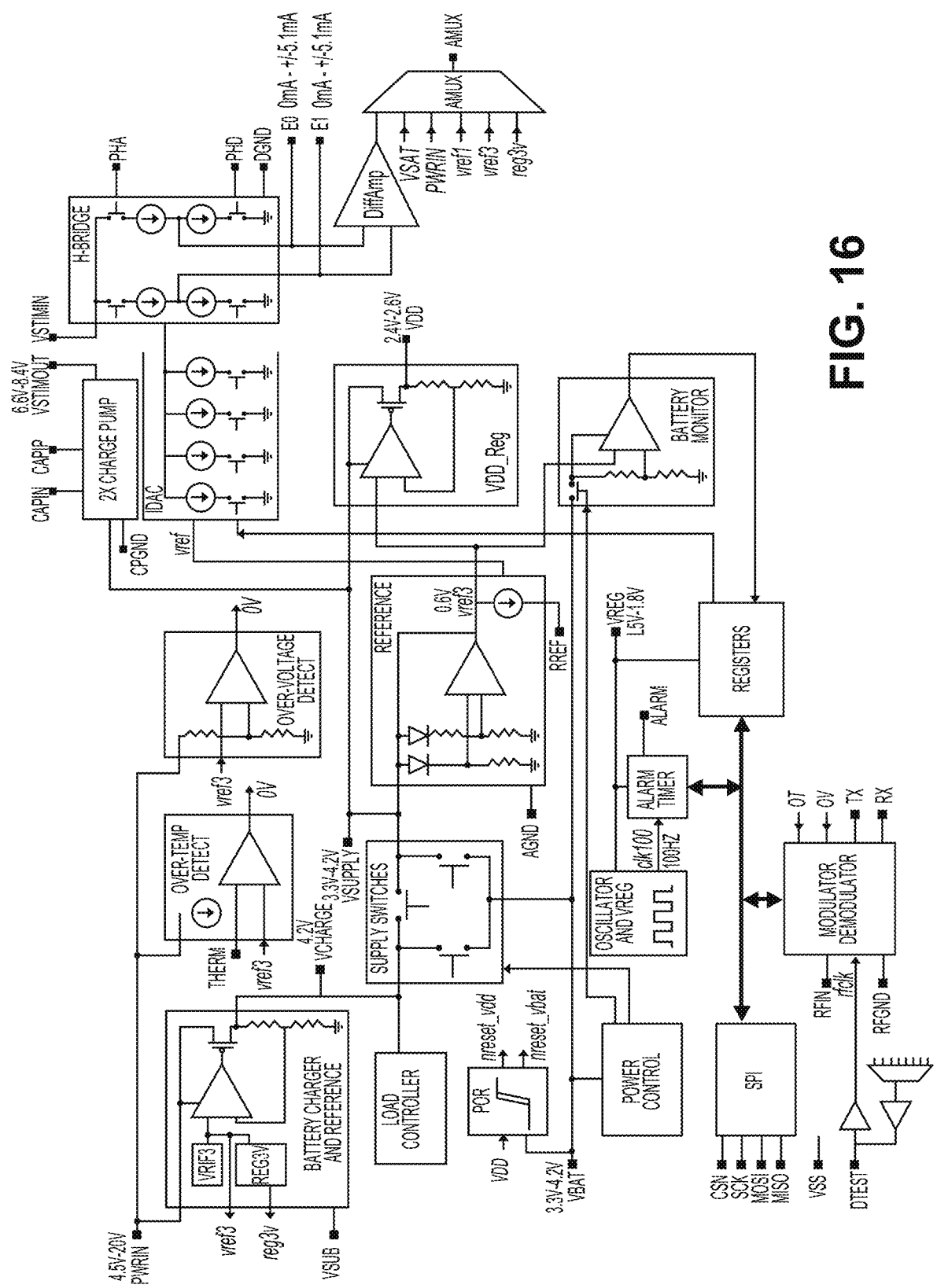
FIG. 16 is a high level ASIC schematic of the microstimulator of FIG. 15.

The operation of the ASIC in this example may be understood through an understanding of each functional block, explaining the system-level implications. The system schematic is shown in FIG. 15, and a high level ASIC schematic is shown in FIG. 16.

Figure 25A:
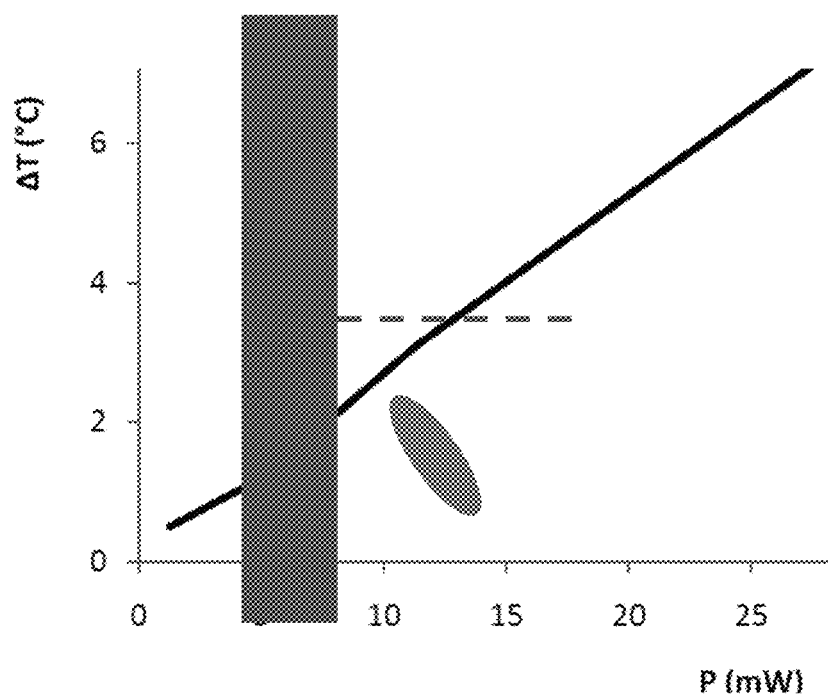
FIG. 25A is a graph showing the thermal operation range of a microstimulator per charging power.
Figure 25B:
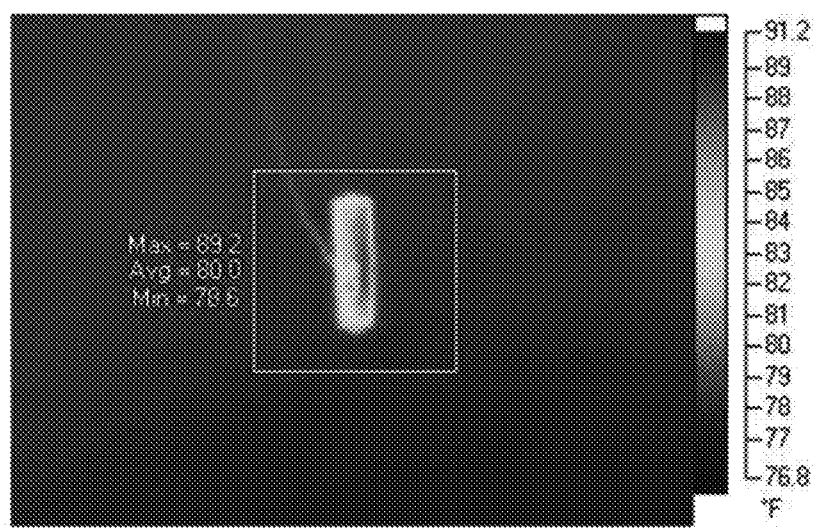
FIG. 25B shows a thermal image of a mock implant with H=64 A/m.

Any of the microstimulators described herein, including this exemplary microstimulator, may include thermal protection. Although the Energizer throttles the magnetic field so that the Microstimulator does not overheat or saturate the telemetry communications, it is possible that if these controls fail, the Microstimulator temperature could climb over 41° C. potentially causing damage to tissues. The primary source of heat will be the coil. Normal body temperature itself can reach 38° C. leaving a narrow range of thermal operation as shown in the diagram in FIG. 25A. The black diagonal line is temperature rise of the coil with power absorbed in air and may have a lower slope in the body. The maximum level of energy transfer is about 13 mW, when the battery is fully discharged it requires about 3 mW of power to charge, this chart indicates that the system can operate safely while absorbing between 5-10 mW of power.

As a second line of defense to prevent overheating, a thermistor is mounted at the base of the coil so that when the temperature reaches a point so that the temperature on the electrode contacts could reach 41° C., the coil will be shorted, dramatically reducing energy absorption. Given that thermistors are only accurate to about 2° C. and the thermal shutoff circuit in the ASIC has even a wider variation, an external thermal threshold resistor is selected during the manufacturing test so that the shutoff can be controlled to within half of a degree C.

Figure 26:
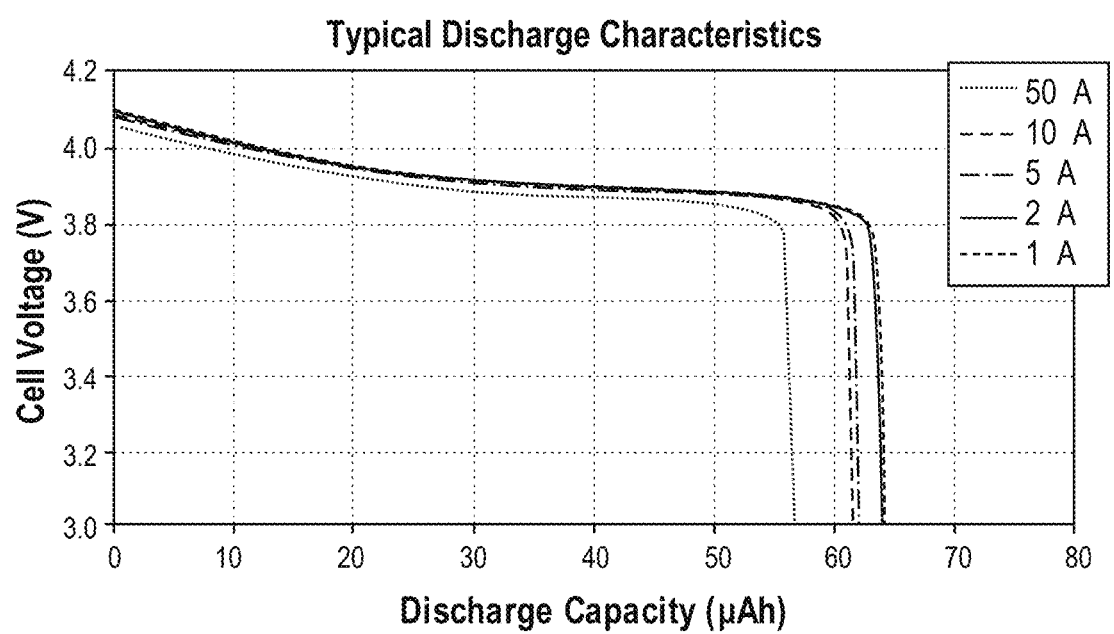
FIG. 26 shows a discharge curve for one variation of a battery that may be used with a microstimulator.
Figure 27:
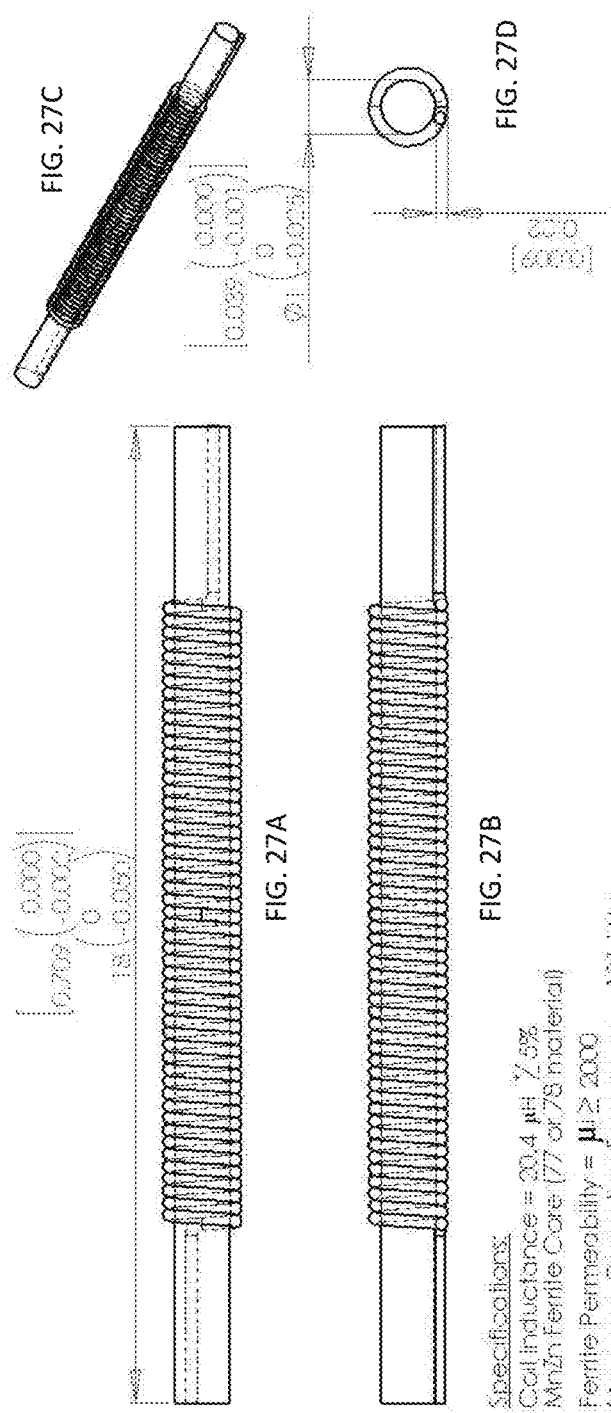
FIGS. 27A-D show top, side, side perspective and end views, respectively, of a ferrite resonator that may be used as part of the microstimulators described herein.

The battery being utilized in this example is a solid-state LiPON with a nominal voltage. The Recharge time is 20 minutes to a capacity of 80%. The charging voltage range is 4.00-4.15V where the optimum value is estimated to be 4.08V. The battery supports more than 5000 cycles with a 10% depth of discharge. The discharge curve for the battery is shown in FIG. 26.

The input impedance of this battery is fairly high and must be managed, since the system may require 8 mA current spikes for a duration of 1 mS at a rate up to 20 times per second. These high current pulses are enabled with a large 22 uF capacitor paralleled with 3 50 uAhr cells.

This variation of a microstimulator also includes a resonator that is typically a coil and capacitor designed to resonate at 131 KHz±2%. The coil is constructed with many turns of magnet wire with a target inductance of about 20 uH. An external high quality NPO capacitor is used to set the tank frequency. NPO is chosen due to a low dielectric loses (ESR) and high accuracy. It is possible that a second smaller trimming capacitor may be required. This capacitor must be able to tolerate the high voltages that can be induced on the coil. As a safety precaution zener diodes limit the voltage across the capacitor providing a second level of protection to the Energizer limiting the generated magnetic field.

Figure 28:
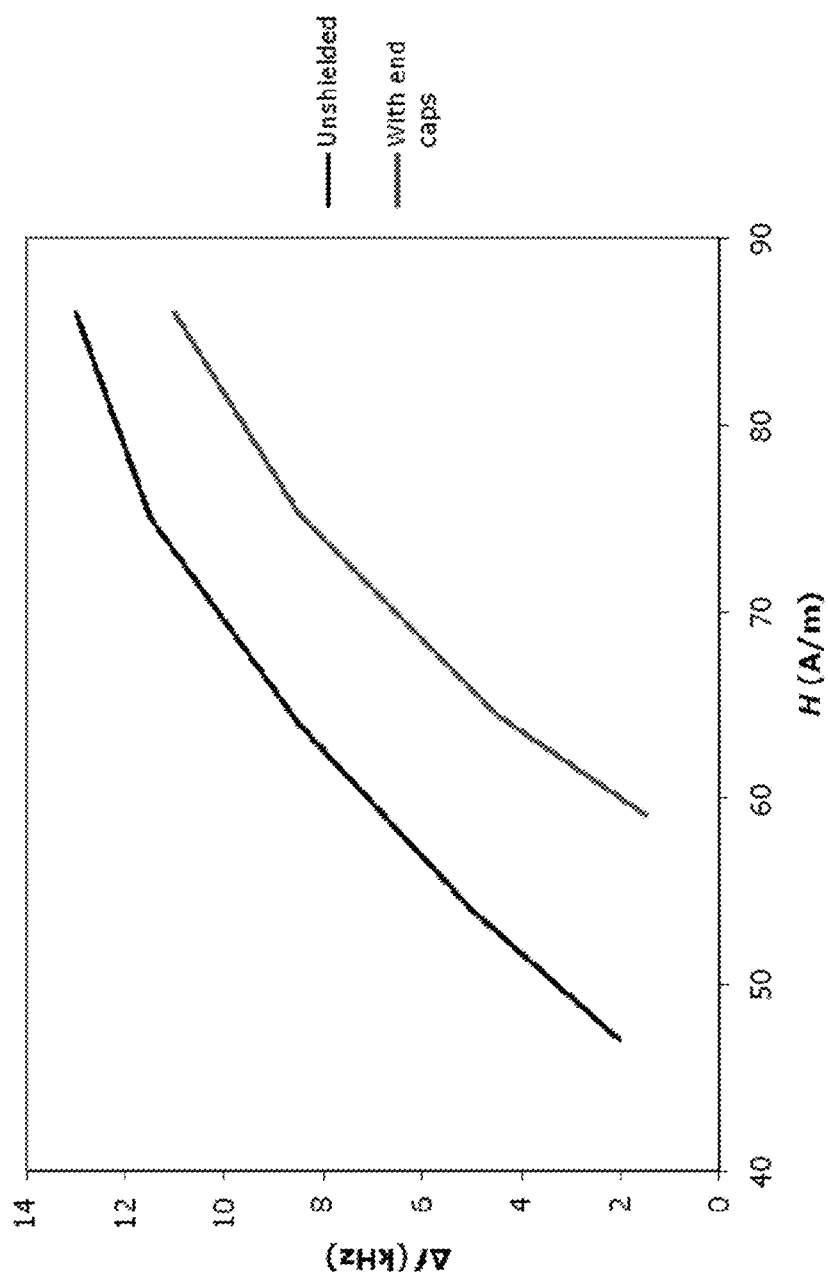
FIG. 28 is a graph of frequency range vs. field strength with and without end caps on the microstimulator.

The coil uses a ferrite coil to concentrate the flux. A long thin design was selected to improve the efficiency and limit the amount of required ferrite for increased MRI compatibility. The long ferrite increases the effective permeability P α (uA)2. The design of the ferrite is shown in FIGS. 27A-D. Care must be taken to minimize the amount of RF absorbing/conductive material shielding the resonator. FIG. 28 is a graph of the Resonator in free air vs. a coil with the hybrid and hermetic end caps sealing the hermetic capsule. In this graph, a stronger magnetic field is required to overcome the shielding. The use of ceramic and highly resistive alloys such as Grade #36 Titanium is used to reduce shielding.

Figure 29:
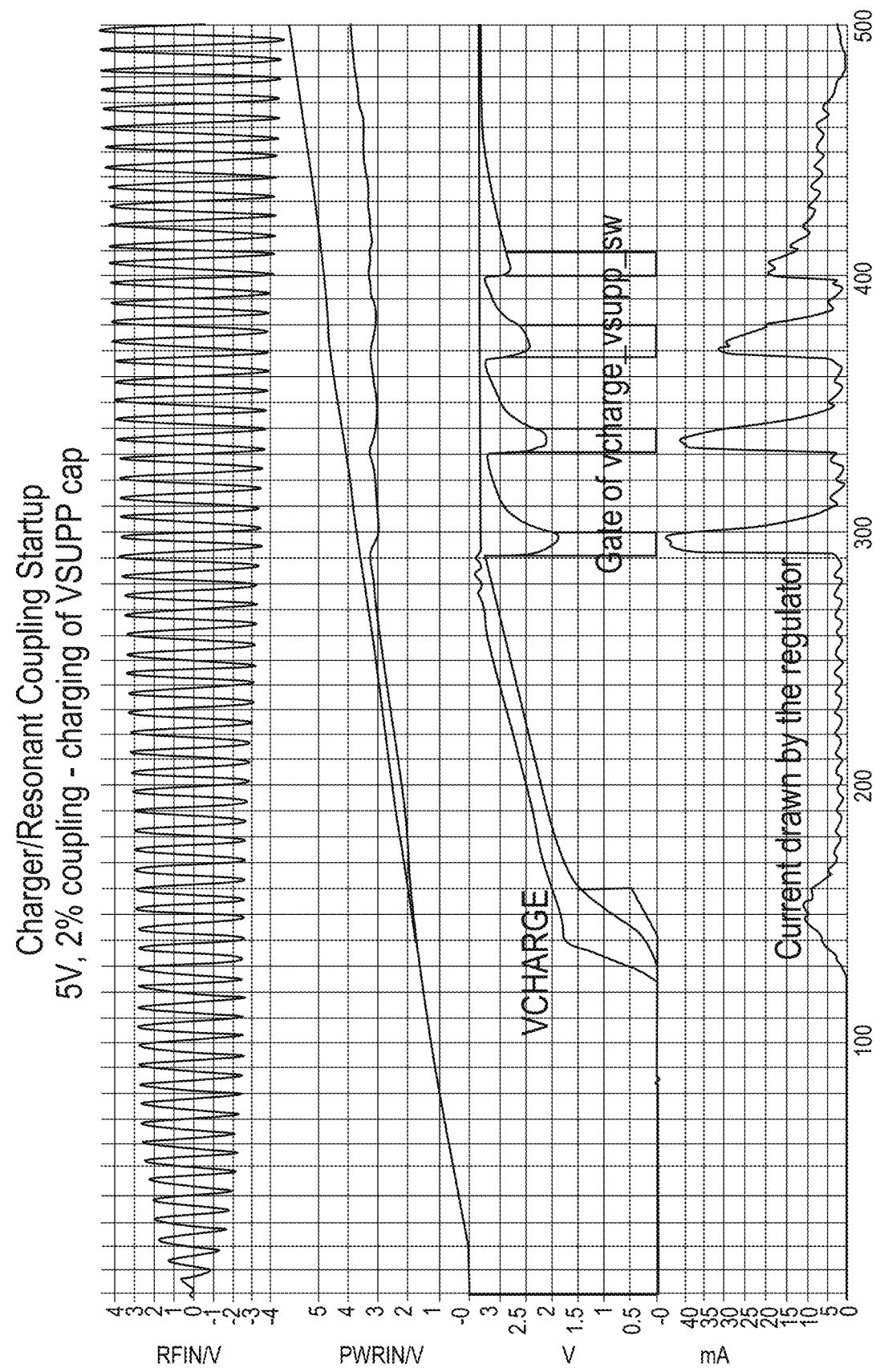
FIG. 29 shows a composite graph of a microstimulator beginning to charge.

During system startup the resonator typically cannot start the system without resulting in chatter and unpredictable states. This problem is solved by limiting the amount of power that can charge the battery and capacitors with current limiters. The operation is shown the composite graph of FIG. 29 with limiters in place.

Returning now to FIG. 24B, The CCAD08 ASIC works with a Micro Controller Unit (MCU) to perform all of the required functions for the Microstimulator product defined in herein. The functions of the ASIC include electrode stimulation, wireless communication interface, wireless supply recharge, interval timing, and power supply management. Further detail of the ASIC properties is provided below for this exemplary embodiment.

In this example (shown in FIGS. 24A and 24B), the Battery Charger is connected to the PWRIN signal. It produces a regulated output voltage [VCHARGE] of ~4.2V from an input voltage at PWRIN ranging from ~4.3V to ~20V. The VCHARGE output is regulated by a linear amplifier that compares an internal voltage reference [vref3] to a feedback signal from VCHARGE. The VCHARGE output is connected through the Supply Switches to a rechargeable battery. The Battery Charger must operate independently of other ASIC functions, so it includes its own voltage reference [vref3] and regulated supply [reg3v] that are supplied by PWRIN. The voltage reference [vref3] and regulated supply [reg3v] are also used by the Over-Voltage and Over-Temp Detectors. The output voltage [VCHARGE] can be calibrated by programming an appropriate calibration code into the VCHARGECAL Register. The Battery Charger also includes logic outputs [in_reg], [ref_good], [chrg_good] that indicate when the circuit is in regulation, when the voltage reference is valid, and when the VCHARGE output voltage is ready for connection to the battery.

The Load Controller is connected to the VCHARGE signal. It controls the load current out of the Battery Charger to produce a constant load on PWRIN, and thus constant equivalent impedance at the antenna. The constant antenna impedance provides better consistency of the wireless communication. The Load Controller compares the actual load current on VCHARGE to a pre-determined target current, and adds extra load current to make up the difference. If the actual load current exceeds the target current, the Load Controller has no function. The target current can be selected to be 3 mA, 2 mA, 1 mA, or 0 mA (disabled) by programming the LOAD_SELECT bits of the DEMODCTRL Register. The Load Controller is enabled by automatically upon the rise of PWRIN.

The Over-Voltage Detect circuit monitors the PWRIN signal and produces a logic output [ov_detect] when the PWRIN voltage exceeds 30V. The output [ov_detect] connects to the Modulator which loads down the RFIN signal to reduce the Q of the antenna network and thus reduces the input power. The circuit includes a comparator that compares a resistor-divided version of PWRIN to a reference voltage. The supply and reference for the Over-Voltage Detect circuit are connected to the reg3v and vref3 outputs of the Battery Charger. The voltage threshold has hysteresis, so after an ov_detect event, the PWRIN voltage must drop below 24V for the ov_detect signal to go low.

The Over-Temp Detect circuit monitors the Microstimulator's temperature by measuring the resistance of an external Thermistor (temperature-controlled resistor). The circuit includes a current source that forces a reference current into the Thermistor through the THERM output, and a comparator that compares the THERM voltage to a reference voltage. The circuit produces a logic output [ot_detect] when the THERM voltage exceeds the vref3 voltage. The circuit is designed to work with a Thermistor that has a resistance of ~62KΩ at 41 C, so in application, a Microstimulator temperature greater than 41 C will cause the over-temperature detection. The output [ot_detect] connects to the Modulator which loads down the RFIN signal to reduce the Q of the antenna network and thus reduces the input power. The supply and reference for the Over-Temp Detect circuit are connected to the reg3v and vref3 outputs of the Battery Charger. The voltage threshold has hysteresis, so after an ot_detect event, the temperature must drop below 39 C for the ot_detect signal to go low. The Over-Temp Detect circuit also includes a calibration mode. The calibration mode can be entered by setting the CAL_MODE bit of the STIMCTRL register. When in calibration mode, the response time of the circuit is slowed-down slightly to guard against tester-noise induced detection.

The Supply Switches are internal MOS switches that direct the flow of current between the Battery Charger output [VCHARGE], the battery terminal [VBAT], and the main supply [VSUPPLY] for the ASIC. The Supply Switches can be configured to allow the VCHARGE voltage to charge up the battery through VBAT, allow the VBAT voltage to supply the system through VSUPPLY, allow VCHARGE to simultaneously charge the battery through VBAT and supply the circuit through VSUPPLY, or disconnect VCHARGE and VSUPPLY such that only the minimal circuitry on the VBAT supply can operate. The configurations of the Supply Switches are controlled by three logic input signals, [charge_sup_on], [charge_bat_on], [vbat_on] that are derived in the Power Control circuit in the Digital block. The Supply Switches block also produces a logic output [vchrg_higher] that indicates when VCHARGE is higher than VBAT, and a supply output [vmax] which always connects to either VCHARGE or VBAT—whichever is the higher voltage. The vchrg_higher signal connects to the Power Control circuit and helps determine the Supply Switch inputs. The vmax supply connects to the supplies of various level shifters that would otherwise malfunction under certain supply conditions.

The Reference circuit is connected to VSUPPLY, and produces an output voltage [vref1] and several output currents [iref_n] for use by the various analog circuits in the ASIC. The reference voltage is created by a typical bandgap reference circuit. The output voltage [vref1] is buffered to provide a low-impedance 0.6V reference. The vref1 output can be calibrated by programming an appropriate calibration code into the VREF1CAL Register. The circuit includes a current reference, which utilizes the reference voltage [vref1], an amplifier, and an external resistor connected to the RREF pin to create a precise reference current [iref]. The circuit also includes current mirrors to produce several independent but matched current outputs [iref_n].

The VDD Regulator is connected to VSUPPLY, and produces a regulated output voltage [VDD] of 2.5V from an input voltage at VSUPPLY ranging from 3.3V to 4.2V. The VDD output is regulated by a linear amplifier that compares the internal voltage reference [vref1] to a resistor-divided feedback signal from VDD. The VDD output serves as the supply for various ASIC circuits. The VDD output is also connected through a MOS switch to the VDD_PAD, which is intended to supply an external MCU, with a 220 nF bypass capacitor. The VDD_PAD switch is controlled by a logic signal [vdd_to_mcu_n], which is derived in the Power Control circuit. In normal operation, the total load current on VDD and VDD_PAD ranges from 100 uA to 2 mA.

The Charge Pump is connected to VSUPPLY, and produces an un-regulated output voltage [VSTIM_OUT] of approximately 2 times VSUPPLY for VSUPPLY ranging from 3.3V to 4.2V. The Circuit uses a combination of internal switches and external capacitors. One capacitor is connected between the CAP1N and CAP1P pins, and another is connected between VSTIM_OUT and CPGND.

The Charge Pump is enabled when the VSTIM_EN bit of the STIMCTRL Register is set. The VSTIM_OUT voltage is produced by first charging the CAP1 capacitor from VSUPPLY to CPGND, and then switching the low side of the capacitor to VSUPPLY and the high side of the capacitor to VSTIM_OUT. The charging and switching phases are alternated at the frequency of an internal charge pump oscillator. Each period of the switching transfers a small packet of charge onto the VSTIM_OUT capacitor until VSTIM_OUT reaches ~2× VSUPPLY. The VSTIM_OUT output is intended to be connected to the VSTIM_IN pin, to provide the supply for the output stage of the H-Bridge. The voltage doubling is required to provide enough supply headroom and low enough output impedance to support up to 5 mA peak and 100 uA average stimulus current output. When VSTIM_EN is not set, VSTIM is connected to VSUPPLY through a relatively high (>100K) resistance.

The Battery Monitor circuit measures the battery voltage [VBAT] and produces two logic outputs [bat_good], [bat_not_dead] according to two programmable voltage thresholds. The thresholds are programmed by the BATMONTRIM Register, with bits 7 through 4 selecting the bat_good threshold and bits 3 though 0 selecting the bat_not_dead threshold. The bat_good threshold can be programmed in the range of 3.5V to 4.0V, with a 33 mV resolution. The bat_not_dead threshold can be programmed in the range of 3.0V to 3.5V, with a 33 mV resolution. The Battery Monitor includes two nearly-identical circuits, each consisting of a comparator that compares a resistor-divided version of VBAT to the internal reference voltage [vref1]. The supply for the Battery Monitor is connected directly to VBAT. To minimize power consumption, the circuit is normally disabled, and only enabled periodically for short durations to make the measurements and latch the results. The circuit also requires the vref3 voltage from the Reference block to make accurate measurements, so the Reference block must also be enabled each time the Battery Monitor is enabled. The measurement sequence is controlled by two logic inputs [bat_mon_en], [bat_mon_latch], which are derived in the Power Control circuit in the Digital block. The bat_not_dead circuit includes an additional feature that creates a single logic pulse [rst_osc_en], which resets the OSC_EN bit in the PWRCNTRL Register any time a battery measurement results in bat_not_dead being false (battery voltage less than threshold). This feature forces the Microstimulator into Storage Mode when the battery gets too low, but allows for recovery through an external charger.

The POR circuit monitors the VBAT and VDD voltages, and provides logic signals [nreset_vbat], [nreset_vdd] that hold logic circuits on their respective supplies in the reset state when the supply voltage is too low for valid logic operation. The nreset_vbat signal is connected to various digital circuits on the VBAT supply, and nreset-_vdd connects to various digital circuits on the VDD supply. The POR block includes two nearly-identical circuits, each consisting of a crude voltage reference, a supply voltage divider, and a comparator. Both circuits must be enabled at all times, so the power consumption in each must be kept to a minimum, and the circuits must work independently of other ASIC circuit blocks. The nreset_vbat signal is set high when VBAT rises to greater than 1.8V, and resets to low when VBAT falls below 1.6V. The nreset_vdd signal is set high when VDD rises to greater than 2.0V, and resets to low when VDD falls below 1.8V. The ASIC also includes a similar function to produce nreset_vreg, but that signal is generated in the Oscillator circuit.

The IDAC converts an 8-bit digital word into an output current [istim] that is linearly proportional to the value of the digital word. The digital word is programmed by writing to the IDAC Register. The output current [idac] sinks into the IDAC from the H-Bridge, and ranges from 0 uA to 127.5 uA, with a 0.5 uA step size. The IDAC is supplied by VDD, and is enabled by the IDAC_EN bit of the STIMCTRL Register. The reference current for the IDAC [iref_dac] comes from the Reference block.

The H-Bridge sources the current [istim] into the IDAC, multiples the current by 40, and mirrors the 40× current to provide sourcing or sinking output currents to the Electrode pins [E0, E1]. The H-Bridge is enabled by setting the HBRIDGE_EN bit of the STIMCTRL Register. The H-bridge also includes switches that are controlled by the MCU's timing signals [PHA, PHB] such that the output current to the Electrodes reverses its polarity at each timing phase change. The output current, which flows through external series (2.2 uF) capacitors to the load, ranges from 0 mA to 5.10 mA as determined by 40× the IDAC setting.

The DiffAmp monitors the voltages at the Electrode pins [E0, E1], and produces an output voltage [vdiff] that is proportional to the voltage difference between E0 and E1. The circuit is supplied by VDD and uses the main internal voltage reference [vref1] as the zero-point of the output range. If the E1 voltage is greater than the E0 voltage, the output [vdiff] ranges between vref1 and VDD. If the E0 voltage is greater than the E1 voltage, the output [vdiff] ranges between vref1 and VSS. If the E1 voltage is equal to the E0 voltage, the output [vdiff] equals vref1. The DiffAmp is enabled by setting the DIFFAMP_EN bit of the STIMCTRL Register. The output voltage [vdiff] is connected to the Analog Multiplexer (AMUX) which connects the vdiff signal to an Analog to Digital Converter (ADC) on the MCU.

In this example, the Demodulator is connected to the RFIN pin which is connected to the antenna network. The antenna receives wireless energy transmitted from the Charger/Programmer at 127-135 KHz. Telemetry data is Manchester Encoded, Amplitude-Shift-Keyed (ASK) at either 1200 or 4800 baud. The Demodulator includes an attenuator and a series of high-pass and low-pass filters and a comparator to extract the Manchester Encoded data from the modulated input signal. It also includes a comparator to extract the clock signal from the carrier frequency. The attenuator reduces the RFIN signal amplitude to VDD level, and sends the attenuated signal to both the clock comparator and the data comparator. The extracted data and the clock are connected to a programmable counter to decode the Manchester Encoded data and produce NRZ data at the RX pin. At power-up, the counter is hardware-preset to a count of 20 to provide a sampling period equal to ¾ of the 4800 baud data period. The counter can be programmed to any value from 0 to 255 to support a wide range of baud rates, including 1200 baud, by writing the DEMODCNT Register. To set the count to the register value instead of the hardware default, the DEMOD_CNT_SEL bit of the DEMODCTRL Register must also be set. When DEMOD_CNT_SEL is not set, the counter uses the hardware preset count of 20. The attenuation of RFIN to the Demodulator input can also be programmed to values of 0.60, 0.50, or 0.33 to accommodate a range of input signal amplitudes by writing the DEMOD_ATT bits of the DEMODCTRL Register. Finally, the carrier-extracted clock can be replaced by an external clock signal driven to the DTEST pin by writing the RFCLK bit of the DEMODCTRL Register. The Demodulator is supplied by VDD and is enabled by the charge_sup_on signal from the Power Control circuit, which indicates when the Battery Charger is supplying power to the rest of the ASIC through the Supply Switches.

The Modulator is connected to the RFIN pin. The circuit consists of a large NMOS switch from RFIN to RFGND that is controlled by a logic signal at its gate. Back-Telemetry data transmission is controlled by the MCU by driving NRZ data into the ASIC's TX pin. Under normal conditions, the TX signal passes directly to the gate of the Modulator switch, such that when TX is low, the RFIN is unaffected, and when TX is high, the Modulator switch turns on and increases the load on RFIN. The load switching produces a Load-Shift-Keyed (LSK) signal at the Telemetry Antenna when the antenna is receiving un-modulated energy at the 127-135 KHz carrier frequency. The Charger/Programmer circuitry detects the resulting voltage and current changes in the carrier driver, and decodes the LSK data to reproduce NRZ data. Under hazard conditions, the Over-Voltage and/or Over-Temp Detect circuits control the gate of the Modulator switch, turning the switch on, regardless of the NRZ data on TX pin.

The Oscillator creates a 100 Hz square wave clock [clk100] for use by the Alarm Timer. The Oscillator must remain powered by VBAT while the remainder of the system is asleep, so the Alarm Timer can trigger a system wakeup. To maximize product-life between charging sessions, the average supply current of the Oscillator must be extremely low (<50 nA). The Oscillator is enabled by the OSC_EN bit of the PWRCTRL2 Register, which activates Timekeeping mode. When OSC_EN=0, the Oscillator is disabled, and the ASIC is in Shelf-Mode, its lowest-current state (<5 nA). Under normal conditions, the Oscillator will be enabled upon the first use of the Microstimulator, and remain on indefinitely. The Oscillator frequency can be calibrated by the lower 6 bits of the OSCCAL Register, with a frequency step-size of 5 Hz. For more precise timing, the MCU can measure the precise Oscillator frequency with a high frequency timer, and then adjust timing parameters according to the measured frequency. The Oscillator is required to maintain timing accuracy of 3 minutes/day between charging sessions, so the Oscillator frequency must be independent of the VBAT voltage, and stable over the expected operating temperature range.

The Voltage Regulator (VREG) creates a pseudo-regulated supply voltage (VREG) for the Oscillator, Alarm Timer, and Control Registers. The primary goal of the VREG circuit is to provide the Oscillator with the means to reject VBAT supply variations in the creation of the 100 Hz clock. To maximize product-life between charging sessions, the average supply current of the VREG must be extremely low (<30 nA). To meet the ultra-low power requirements, the VREG circuit uses a Sum-Of-Thresholds approach to the voltage regulation. The circuit consists of a bias-current generator, a current mirror, and a stack of gate-drain connected NMOS and PMOS devices. The current mirror forces current through the MOS devices to produce a voltage that is proportional to the sum of the NMOS and PMOS thresholds. Since the MOS thresholds have large process variations, the VREG voltage also has high process variation, but the variations over temperature and VBAT conditions are small, so the primary goals are met with a very low overhead power. The VREG also supplies the Alarm Timer and Control Registers. Both of these circuits are enabled for most of the Microstimulator life, so they require a supply with very low overhead power. To minimize switching transients on VREG due to the digital functions, an external 1 nF capacitor should be connected between VREG and VSS. The VREG circuit also includes a POR circuit for the digital blocks on the VREG supply. The output of the circuit (nreset_vreg) is connected to the nreset inputs of the Alarm Timer and Control Registers. The nreset_vreg output is high when VREG exceeds 1.5V. When VREG is less than ~1.5V, nreset_vreg holds the Control Registers in their reset states. In particular, the OSC_EN bit is set to 0, and the ASIC enters Shelf-Mode.

The Analog Multiplexer (AMUX) is supplied by VDD. It selectively connects one of multiple analog signals to the AMUX pin which is connected to the ADC on the MCU. The AMUX is enabled by setting the AMUX_EN bit of the AMUX Register. The input signal selection is controlled by the lower 3 bits of the AMUX Register. The inputs to the AMUX are; the DiffAmp output [vdiff], the wireless power input [PWRIN], and the battery voltage [VBAT]. Each of the signals must be gained or attenuated as appropriate such that the full-scale range of expected inputs matches the full-scale input range of the ADC on the MCU. The AMUX is also used to connect various other analog signals to the AMUX pin to support ASIC test and debug. The details of the AMUX signals, their corresponding selection codes, and their gain/attenuation factors are defined in the Register Definitions section of this document.

The Serial Peripheral Interface (SPI) is an industry-standard SPI Slave modeled after the SPI Slave in the STM M95010 EEPROM. It provides 1 MHz serial communication access to the ASIC from the MCU, which includes an SPI Master. The Interface include 4 wires, including; serial clock [SPI_CLK], chip select [SPI_CSN], Master-Out-Slave-In [SPI_MOSI], and Master-In-Slave-Out [SPI_MISO]. The ASIC's SPI supports burst reads and writes in which the MCU can write a read/write instruction and a starting address, and the read or write multiple successive data words for a range of addresses. The detailed sequences and timing for the SPI read and write procedures are documented in the Timing Specifications section. The SPI is supplied by VDD to produce logic levels that match the MCU's logic levels.

The Control Registers are standard read/write registers that can be accessed by the SPI. The Control Registers are configured as an array of 8-bit registers, each with a unique address. The Control Registers include read/write registers that will store device configurations, mode selections, and calibration data. The registers are supplied by VREG and will therefore retain their contents as long as adequate battery voltage is supplied. The Registers also include two read-only registers; the ASICREV Register, which stores the ASIC revision code, and the SUPPLYMON Register, which includes logic signals representing the status of various power supply monitors. The Control Registers also include read/write registers used to support ASIC test and debug. The specific functions of all the registers and bits are defined in the Register Definitions section of this document.

The Alarm Timer is supplied by VREG. It includes a 40-bit ripple counter register that is clocked by the Oscillator clock [clk100], and is read/write capable via the Serial peripheral Interface (SPI) as five 8-bit registers COUNTER0 through COUNTER4. It also includes a second 40-bit read/write capable register and combinational logic that produces a 1.28 s to 2.56 s digital output pulse [rtc_alarm] when the contents of the two 40-bit registers match. The rtc_alarm signal is sent to the Power Control block, and to the MCU via the ALARM pin. After the alarm event has been recognized by the MCU, the rtc_alarm signal can be cleared by writing to the RST_ALARM bit of the ALMCTRL Register. Typical use of the Alarm Timer will consist of a calibration by the MCU involving reads of the ripple counter before and after a fixed time duration (controlled by the MCU's precise clock, or determined via reference to an external time source accessed via the wireless link). The MCU will calculate a correction factor to translate the ASIC's time base to the MCU's precise time base, and set the 40-bit Alarm Register accordingly. The Alarm time can be set by writing to the ALARM0 through ALARM4 Registers, which are concatenated to form one 40-bit data word. To avoid data integrity problems with the Ripple Counter, the COUNT DIS bit of the ALMCTRL Register should be set prior to writing the Ripple Counter, and cleared after the write is complete. The Ripple Counter must also be written in sequence from COUNTER0 to COUNTER4.

The Power Control block includes control logic for the operation of the Supply Switches and the Battery Monitor. The connections between these sub-blocks and the blocks they interact with are shown in the diagram below. The typical supply sequence will begin with the first application of the battery. The battery will typically be attached with little or no charge. After battery attach, an automated tester will charge the battery directly via the VBAT pin. The Microstimulator will then stay in Storage Mode, with minimal battery leakage until the first application of the external Charger. When the external Charger is applied, PWRIN begins to rise, and the Battery Charger begins to turn on. The Battery Charger monitors the supply conditions, and when PWRIN is sufficiently high, the Power Control circuit turns on Switch1, which connects VCHARGE to VSUPPLY. At this time, the Demodulator and Load Controller also turn on. When VSUPPLY increases, the Reference, VDD Regulator, and VDD Switch (Switch 5) are all enabled, and thus the MCU starts-up. Once enabled, the MCU will set the OSC_EN bit of the PWRCTRL2 register to turn on the Oscillator and VREG, and enter Timekeeping Mode. In Timekeeping mode, the Alarm Timer will initiate periodic (every 90 minutes) battery measurements. To make the measurements, the Reference, VDD Regulator, and Battery Monitor (Switch 4) are enabled, but the VDD Switch (Switch 5), and thus the MCU are off. The Alarm timer will also wake up the whole Microstimulator whenever the pre-programmed alarm duration has expired. When the duration expires, the ALARM pin is set high, and the Reference, VDD Regulator, and VDD Switch (Switch 5) and thus the MCU, are enabled. The MCU must then set the MCU_VDD_ON bit of the PWRCTRL register prior to the Alarm's 1-2 second timeout, to keep itself enabled. After MCU_VDD_ON is set, the MCU can perform any operation, such as enabling ASIC sub-blocks and running Stim patterns. To return to Timekeeping Mode, the MCU must clear the MCU_VDD_ON bit.

Figure 30:
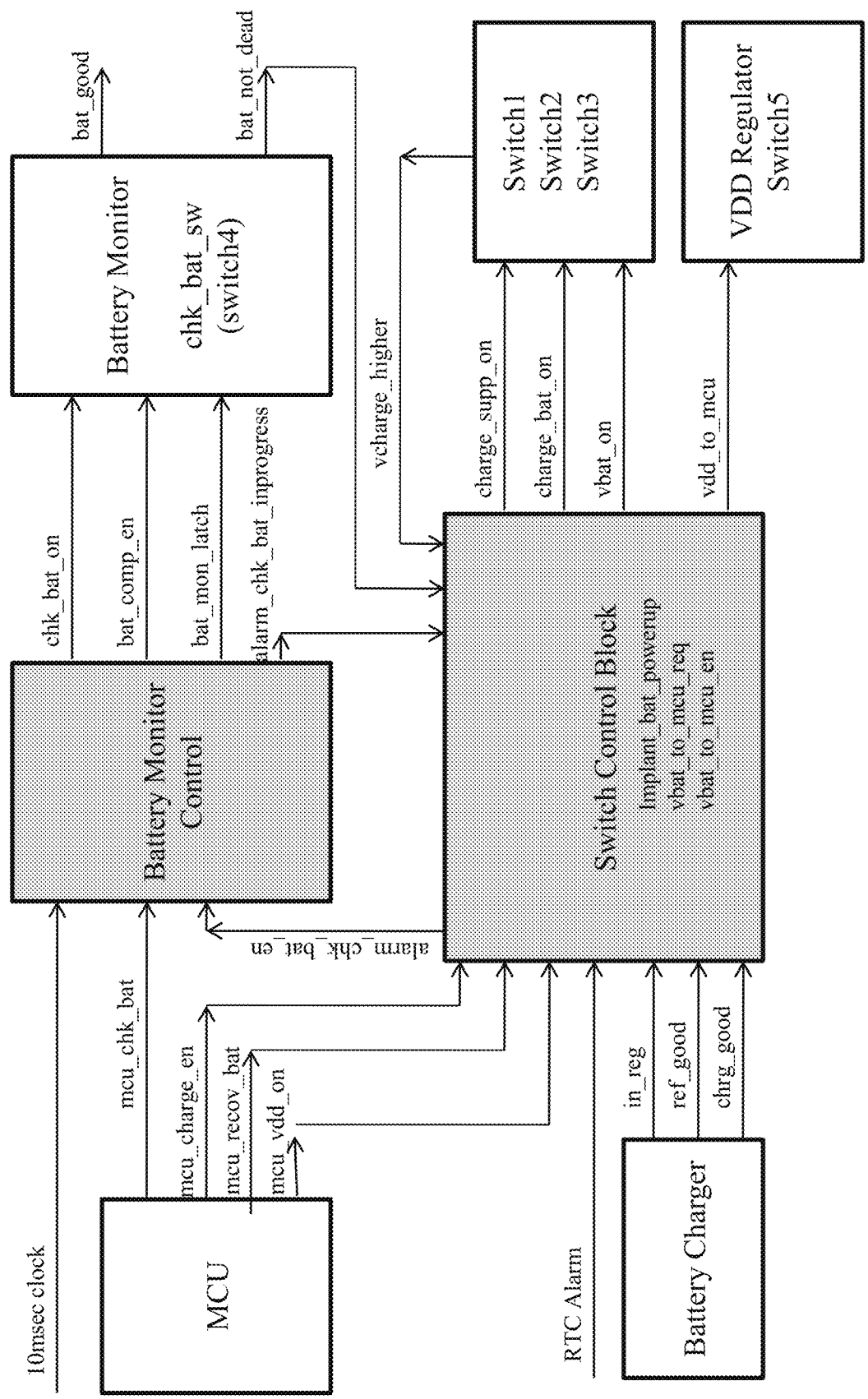
FIG. 30 shows a circuit diagram of a microstimulator including switch control.

FIG. 30 shows a circuit diagram for a microstimulator including some of the elements described above, as well as a switch control block. The switch control circuit includes combinational logic that turns on or off the switches in the Supply Switches block, as well as the VDD_PAD switch and the "check battery" switch within the Battery Monitor. The switch definitions and conditions are defined as follows: Switch1 is the switch between VCHARGE and VSUPPLY. It is turned on when the system is being supplied by the external charger and not by the battery. The gate of Switch1 is controlled by the charge_supp_on signal. The logic for charge_supp_on is as follows: charge_supp_on=charger_on AND NOT [alarm_chk_bat_inprogress]. charger_on indicates a valid output voltage at VCHARGE. charger_on is asserted as VCHARGE rises above the threshold. This threshold must be higher than the point where the internal band-gap reference is valid. The charger_on signal is de-asserted when the internal band-gap reference is not valid.

alarm_chk_bat_inprogress is the signal from battery monitor state machine that indicates an alarm initiated battery check measurement is in progress.

Switch2 is the switch between VCHARGE and VBAT. It is turned on when the battery is being re-charged. The gate of Switch2 is controlled by the charge_bat_on signal. The logic for charge_bat_on is as follows: charge_bat_on=vchrg_higher AND mcu_charge_en AND in_reg AND [mcu_recov_bat OR bat_not_dead] vchrg_higher indicates that VCHARGE is greater than VBAT. mcu_charge_en can be de-asserted by the MCU to interrupt charging in order to perform an MCU initiated battery measurement using mcu_chk_bat. in_reg indicates that the Battery Charger Output (VCHARGE) is in regulation. bat_not_dead indicates that VBAT is above the programmable Dead-Batt threshold. mcu_recover_bat indicates that the MCU wants Switch2 on—even if VBAT is less than the DeadBatt threshold, This allows the MCU to recover a dead battery.

Switch3 is the switch between VBAT and VSUPPLY. It is turned on when the system is being supplied by the battery and not the external charger. The gate of Switch3 is controlled by the vbat_on signal. The logic for vbat_on is as follows: vbat_on=implant_bat_powerup OR alarm_chk_bat_inprogress; alarm_chk_bat_inprogress indicates that an alarm-driven battery check is being performed. implant_bat_powerup indicates that the battery is to power up the MCU, either to perform an Alarm-initiated initial power-up or to extend an Alarm-initiated power-up. implant_bat_powerup is defined as: implant_bat_powerup=vbat_to_mcu_req AND vbat_to_mcu_en. vbat_to_mcu_req is the request to power up the MCU from battery. vbat_to_mcu_req is defined as: vbat_to_mcu_req=[rtc_alarm OR mcu_vdd_on] AND bat_not_dead. vbat_to_mcu_en is the precondition for powering up the MCU from battery. vbat_to_mcu_en is defined as: vbat_to_mcu_en=NOT [charger_on]. alarm_chk_bat_inprogress is generated in the Battery Monitor Control block. alarm_chk_bat_begin is defined as: alarm_chk_bat_begin=alarm_chk_bat_req AND alarm_chk_ bat_en. alarm_chk_bat_req is generated by alarm to request a battery check. alarm_chk_bat_en is used to block alarm generated battery check requests when the MCU is powered up. alarm_chk_bat_en is defined as: alarm_chk_bat_en=NOT [vbat_to_mcu_req OR charger_on].

Switch4 is the switch between VBAT and the sensing circuitry within the Battery Monitor. The gate of Switch4 is controlled by the chk_bat_on signal. chk_bat_on is generated by the Battery Monitor Control block. It is triggered by either mcu_chk_bat or alarm_check_bat_begin, and stays on for the 30 msec battery monitoring cycle.

Switch5 is the VDD_PAD switch, which is between the internal ASIC VDD and the VDD pin, which supplies the MCU. Switch5 is needed because the battery measurement requires a valid VDD for the ASIC, but the load presented by the MCU would corrupt the battery measurement. The gate of Switch5 is controlled by the vdd_to_mcu signal. The logic for vdd_to_mcu is as follows: vdd_to_mcu=NOT [alarm_chk_bat_inprogress]. alarm_chk_bat_inprogress is generated in the Battery Monitor Control block. alarm_chk_bat_begin is defined as: alarm_chk_bat_begin=alarm_chk_bat_req AND alarm_chk_bat_en. alarm_chk_bat_req is generated by the Alarm Timer to request a battery check. alarm_chk_bat_en is used to block alarm generated battery check requests when the MCU is enabled. alarm_chk_bat_en is defined as: alarm_chk_bat_en=NOT [vbat_to_mcu_req OR charger_on].

The Battery Monitor Control circuit includes a state machine that controls the sequence of events required for a battery voltage measurement via the Battery Monitor circuit. By default, the Battery Monitor Control initiates a battery measurement every 90 minutes. An un-scheduled battery measurement can also be initiated by the MCU by setting the MCU_CHK_BAT bit in the PWRCTRL Register. The state machine uses the 100 Hz clock to produce the chk_bat_on and bat_mon_latch signals required to enable Switch4 and the Battery Monitor circuit, and to latch the results of the battery measurements. A third signal, alarm_chk_inprogress is used in the Switch Control block to control Switch5—to keep the MCU load off of VDD when a battery measurement is in progress.

The DFT Block provides digital test access to the Power Control and Alarm Timer blocks via the DTEST pin. The DTEST pin can be programmed to be an input or an output by setting or clearing the DTEST_OEN (Output_Enable_Not) bit in the DTESTCTRL Register. When DTEST is an output, it can be connected to one of eight internal signals as defined by the lower 3 bits of the DTESTCTRL Register. One of the signals [cntr_q7_out] is the bit7 output of one of the 5 Ripple Counter bytes as selected by the lower 3 bits of the TSTCNTR Register, and enabled by the TST_CNTR bit of the TSTCNTR Register. When TST_CNTR is set, the 5 bytes of the Ripple Counter are clocked in parallel instead of in series, and clocked by SPI_CLK instead of clk100. In this mode, the 5 individual byte outputs can be tested with a very short test duration. The other signals that can be routed to DTEST are documented in the Register Definitions section of this document. When DTEST is an input, it can be used as an alternate clock input for the Demodulator. The DFT Block also contains a test register [PWRTESTCTRL] that allows the tester to force the states of various Power Control signals. When bit7 of PWRTESTCTRL is set, the Power Control circuitry is connected to 6 other bits of the PWRTESTCTRL Register—instead of their normal internal ASIC signals. The detailed mapping of signals to register bits is documented in the Register Definitions section of this document.

The Level-Shifters are required to interface digital logic signals that cross boundaries from one supply domain to another. The ASIC includes levels shifters for nearly every combination of supplies (VDD, VREG, VBAT, VSUPPLY, VCHARGE, VSTIM, PWRIN).

The Pad Ring consists of circuits and devices intended to protect the ASIC from ESD events. For analog pins, the Pad Ring cells typically have a negligible effect on the function and performance of the circuit. For digital pins, the Pad Ring cells include the appropriate Input, Output, or Input/Output buffering, as well as the ESD protection. All of the digital Pad Ring circuits include diodes connected between the pin and VDD_PAD and between the pin and VSUB. The analog Pad Ring circuits include diodes and special ESD clamps between the pin and VSUB. The analog pins do not include diodes to VDD_PAD. The Pad Ring is intended to meet the JEDEC standard for 2 KV Human-Body-Model (HBM) ESD protection.

Charger

Figure 31B:
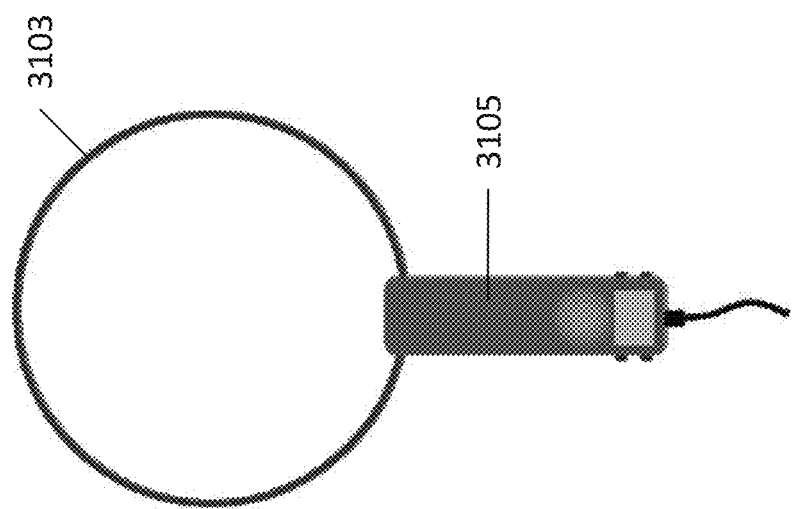
FIGS. 31A and 31B illustrate variations of chargers for externally charging an implanted microstimulator.
Figure 31A:
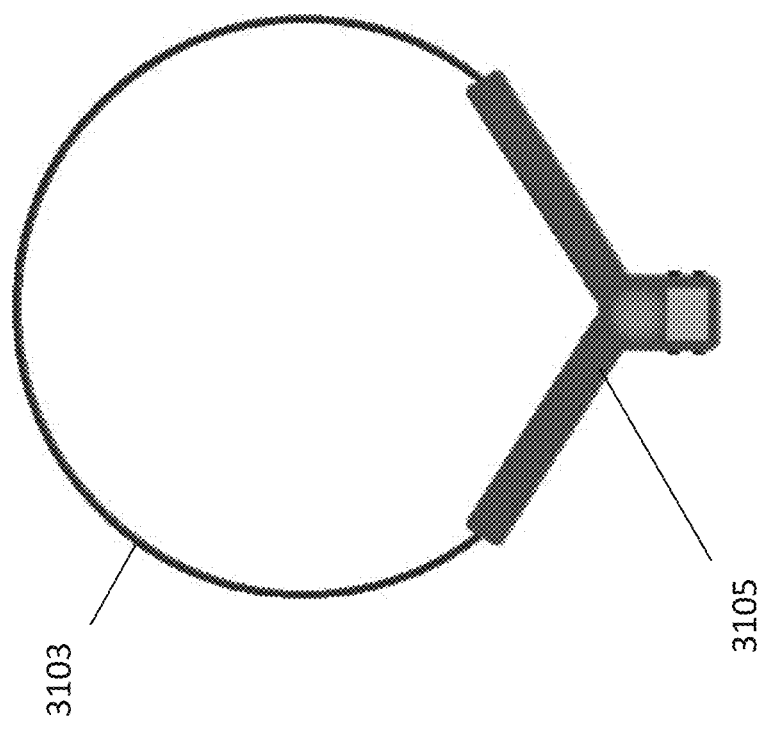

The Patient Charger communicates with and replenishes the Microstimulator deep within the neck utilizing the near field effects of an electromagnetic field. The Patient Charger is designed to be used by both clinicians and patients. It consists of a coil that is run through a handle that separates to expand for placement over then head. Once placed over the head and closed the Patient Charger may attempt to find the Microstimulator and start charging. When charging is complete the patient may be signaled. FIGS. 31A and 31B illustrate one variation of a charger (which may also be referred to as a patient charger or an energizer). In use, a clinician may program the microstimulator by connecting a USB cable between the Prescription Pad and the Patient Charger. The Patient Charger wirelessly connect with the implant and with outer devices (e.g., the controller such as a prescription pad). The Patient Charger may also record all charging sessions and store Microstimulator data.

The chargers described herein are configured and optimized for use with the cervical, low duty-cycle microstimulators described above. Thus, these chargers have many advantages over any prior art systems. In particular, these charges may be worn about a subject's neck and may very quickly charge the implanted microstimulator, and may program and control the microstimulator as well as receive data or information from the microstimulator. The chargers described herein may use a solenoid that connects around the subject's neck with novel connection mechanism. For example, the connection mechanism may be clasp or quick connect connector that connects the loop (coil) of the charger around the subject's neck. The quick connector may be magnetic or friction fit. For example, in some variations the connector closing the loop around the subject's neck includes insertion of pins to connect one side of the loop(s) with the opposite side. For example, in some variations, the charger (e.g., energizer) coil uses a breakable coil with a magnetic latch and pogo spring pins to make contact. The coil resistance may be kept low despite the clasp/connection. For example, a multiplicity of pins may be used to keep coil resistance low and Q high.

In some variations, a high-efficiency class-D amplifier may be used to drive coil reliably. A variable frequency may be used to maximize power transfer and may be tracked with a control loop. In some variations, a variable inductor that uses DC flux to vary coil permittivity may be used to tune the coil to maximize transfer. In some variations, a measure of back telemetry modulation depth allows closed loop control of the magnetic field to optimize power transfer, avoid Microstimulator overheating, and avoid saturation of telemetry communications.

The magnetic field strength of the charger may be modulated via a digitally compensated pwm circuit so that the power is critically tuned rather than using a resistive element. In addition, the carrier frequency may be generated using a phase accumulator to provide highly accurate frequency generation for precise tuning.

The Patient Charger may be stored in a Charging Dock to keep the battery in a charged state. A travel wall socket adapter may also be used. The Charger typically includes a battery, such as a LION rechargeable battery.

Figure 31D:
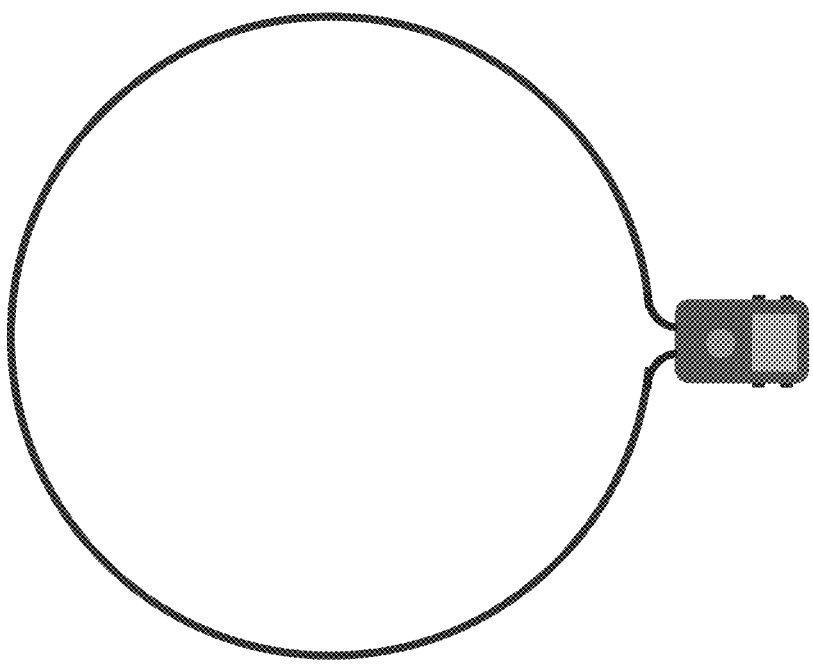
FIGS. 31C and 31D illustrate another variation of a charger.
Figure 31C:
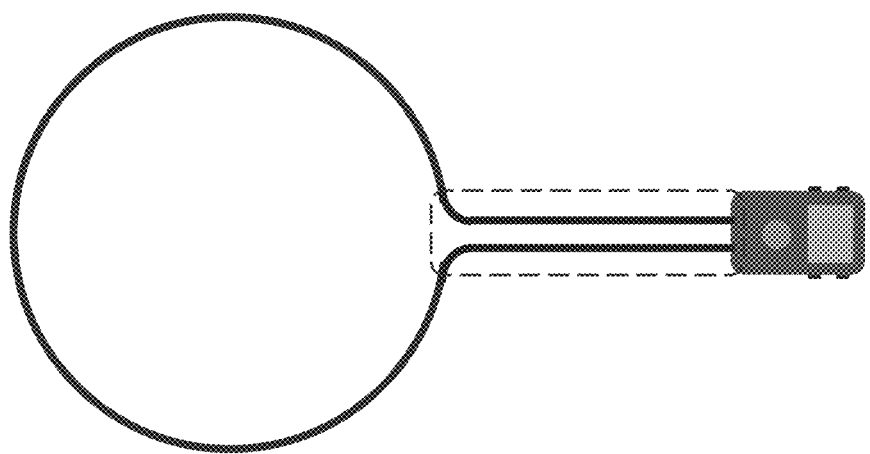

In some variations (such as that shown in FIGS. 31A and B, the charger includes a handle region 3105 and a loop region 3103. The loop region is configured to encircle the patients neck, and may be expanded by opening the handle, as shown in FIG. 31A. Once over the patient's head and around the neck, the handle may be closed, as shown in FIG. 31B, and ready for activation to charge and/or communicate with the implanted microstimulator. The Patient Charger may be configured so that it does not communicate or charge the Microstimulator while the handle is opened. Operation may start once the handle is closed. FIGS. 31C and 31D show one variation of the coil contraction for chargers that include loops that open to fit over the subject's head and close around the neck to charge ("coil contraction and expansion"). In this example, coil contraction is achieved using coil wires and a shroud that can take many cycles of repeated coil opening and closing while maintaining the coil shape. The "arms" shown in FIGS. 31A and 31B are not shown in FIGS. 31C and 31D, but instead the body of the implant may be adjustable (e.g., like a bolo) to shorten the length of the coil. In some variations the body or handle region may slide up the coils after they are positioned around the neck (e.g., FIG. 31C), and slide back down to open the loop up again for removal over the head (FIG. 31D). In other variations described below, the charger may be opened and closed on one or more ends or sides to place it around the subject neck like a collar.

In operation, the Patient Charger typically develops an axial magnetic field in alignment with the Microstimulator in the neck. The loop is sized to accommodate the largest neck and provide sufficient power to charge the battery in the adjustments to assure that sufficient charge is being transferred to Microstimulator.

Recharge time for the Microstimulator may be dependent on how much energy is drained between recharges by the patient. This may depend upon the patient settings and how often the patient charges. Patients may be able to charge as infrequently as every month. This may allow the clinician to recommend a charging schedule that is most convenient for the patient; such as when a care giver is available. The neck loop makes charging a hands free operation once the device is put around the neck.

Figure 32:
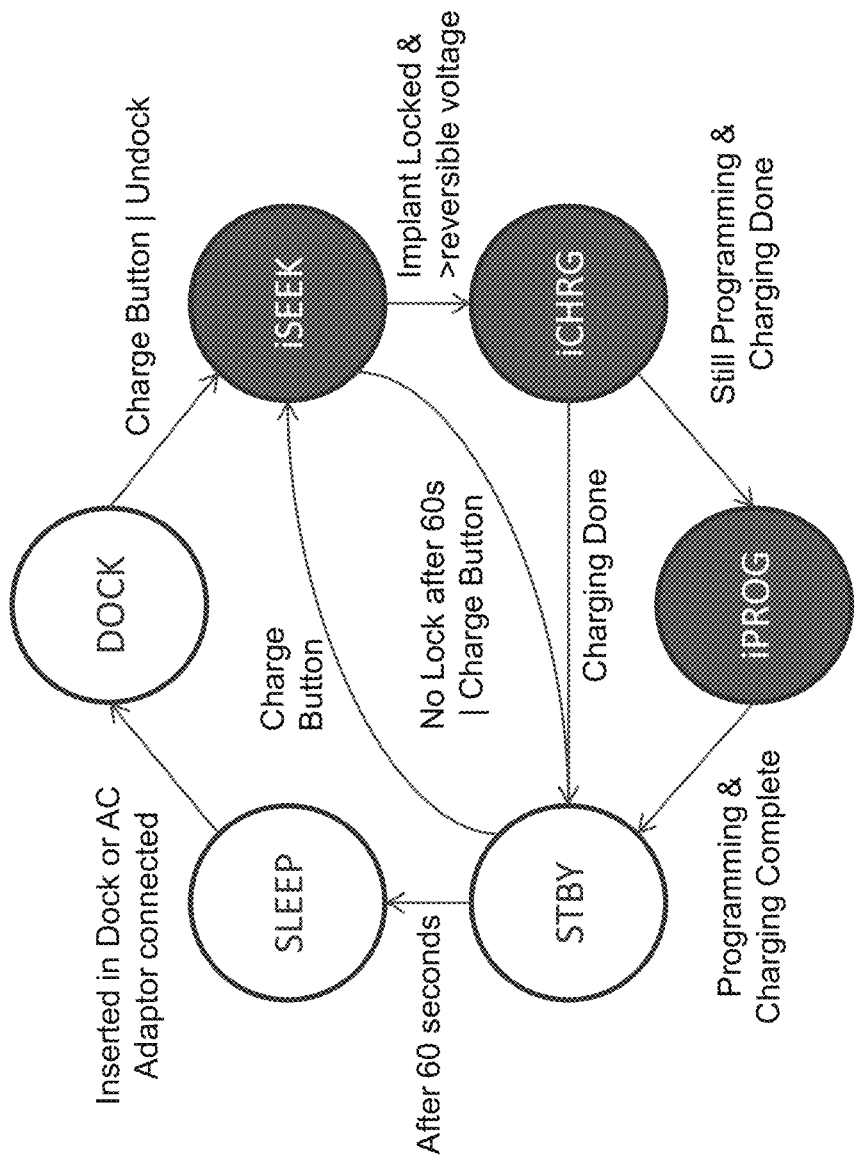
FIG. 32 is a state diagram illustrating the functions of one variation of a charger as described herein.

The operation of one variation of a charger is described in the context of the state diagram shown in FIG. 32. Other variations may include some of these states, or different states; the example shown in FIG. 32 illustrates just one embodiment of operation of a charger. The white-colored states indicate that the Patient Charger is acting alone, the shaded states are when the Microstimulator is locked to the Patient Charger. The states described below may be included.

The DOCK state occurs when the Patient Charger is in Charging Dock and is replenishing, or finished replenishing its own battery. Microstimulator charging is not permitted while in the Charging Dock.

The iSEEK state (or Implant Seek state) occurs when the Patient Charger is out of the Charging Dock and the handle is closed, the Patient Charger automatically starts searching for the Microstimulator (iSEEK) for 60 seconds. Once the Patient Charger detects the Microstimulator, has supplied enough energy to start charging, and established a quality communication link, iCHRG mode is entered. The patient can use the Charging button on the Patient Charger to retry searching or stop searching.

The iCHRG state (or Implant charging state) is started once the Patient Charger has linked to Microstimulator and the Microstimulator has started charging its internal battery. Once charging is complete, and the battery is topped off, STBY mode may be entered. Normal charge is indicated by a Green light on the Charging button, completion of topping off is indicated by a blue light. Topping off the battery occurs when the Patient Charger is left on the neck beyond the normal charging time. This is an optional patient has each time he or she charges the Microstimulator, and takes much longer than normal charging.

The Charging state may only start when the Microstimulator Battery is above the 'reversible' battery voltage and the Charger itself has sufficient charge. If the battery has dropped below the 'reversible' voltage the manufacturer may be contacted for further assistance and reimplantation may be required. During Microstimulator charging, the Microstimulator RTC may be synchronized to the crystal controlled Patient Charger RTC. The Microstimulator event logs may also be uploaded to the Patient Charger. The Patient Charge keeps a complete history of all events that were recorded on the Microstimulator.

The iPROG state occurs if the Prescription Pad is connected to the Patient Charger the Clinician may perform many operations including: Microstimulator Charging, Programming, Diagnostics, and Firmware Update. Some of these operations may require a non-interrupted link and may be restarted if there is an interruption. The Clinician may be notified if this is the case. The Microstimulator may continue to charge during this operation. The system may stay in iPROG until the Prescription Pad specifically disconnects.

The iSTBY state occurs after the Patient Charger has completed charging the Microstimulator but has not been put back into the Dock.

The SLEEP state occurs when the Patient Charger is not docked or in use. The charger may be put into a very low power (sleep) state when only the RTC is active. The RTC is typically always active.

The SETUP state occurs when the user is changing the Patient Charger options on the LCD screen.

Figure 33:
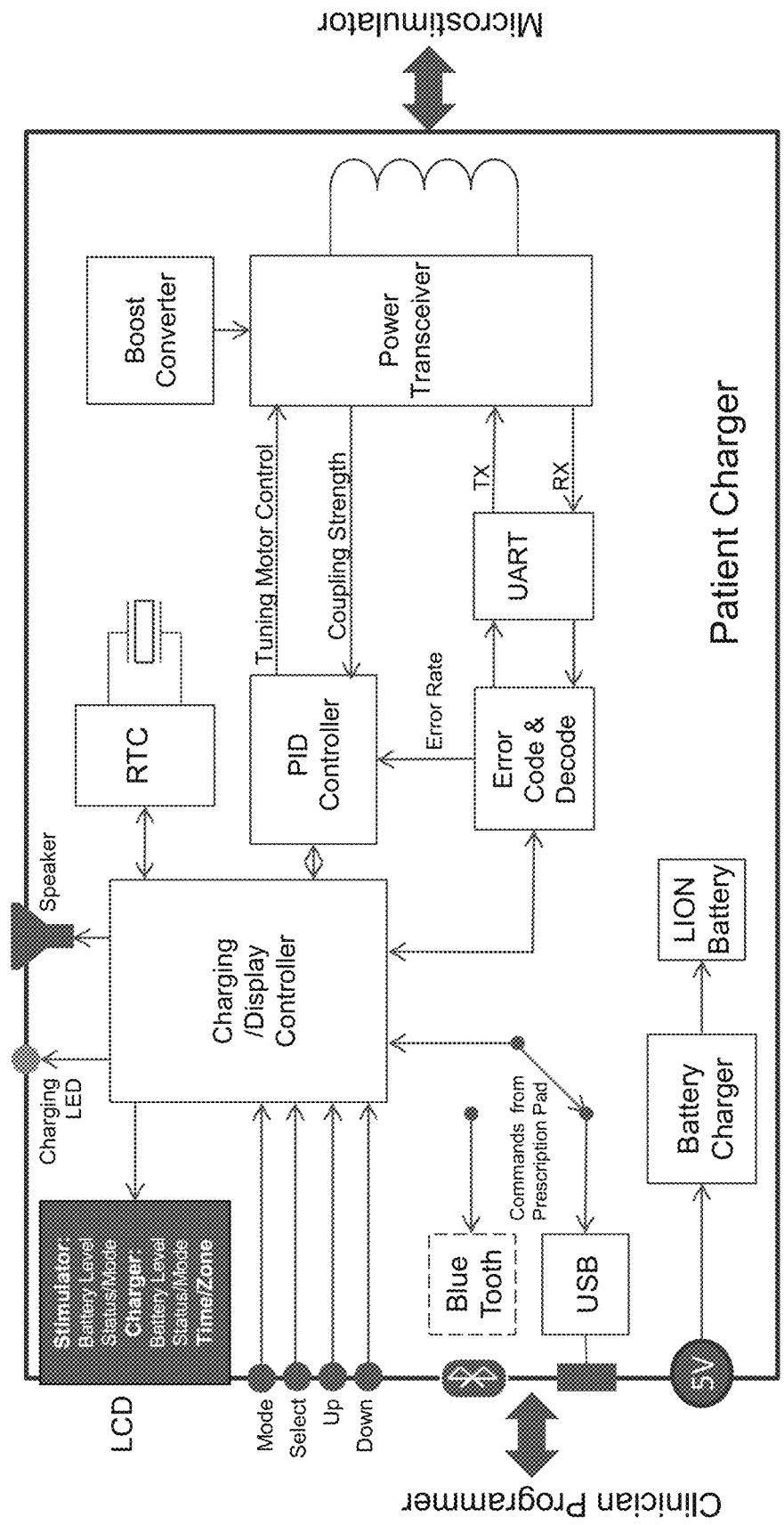
FIG. 33 is a functional diagram of one variation of a charger as described herein.

FIG. 33 illustrates one variation of a functional diagram of a charger. In this example, the charger includes a plastic cover that may cover all metal parts electrically isolated from the user. As described above, the antenna may be sized to fit the largest neck size of 50 cm circumference (≈16 cm diameter), and the largest head size of 63 cm circumference with some allowance for hair with a target of 72 cm circumference (≈23 cm diameter). It is assumed that the closed loop size of 15.5 cm may be used on even the smallest neck. Loop power may be sufficient to charge the Microstimulator up to 45 degrees out of alignment. The weight of the assembly may be minimized and no greater than a few pounds (e.g., less than 1 pound, less than 0.5 pounds, less than 0.25 pounds, less than 0.1 pound, etc.). The device may be dust and water protected.

In FIG. 33, the system control includes a charging/display Controller that may be control overall function of the Patient Charger. An external controller (e.g., Prescription Pad) can send requests to the Patient Charger wirelessly or thorough a wired connection (e.g., through a USB or Bluetooth interface). In some variations, communications with the Microstimulator may be through an RS-232 Interface operating a 4800 bps baud and the frame may be configured as follows: 1 start bit, 8 data bits, 1 even parity bit and one stop bit. The UART may have the ability to detect overruns, noise, frame, and parity errors. The Patient Charger may be able to reload the entire Microstimulator code image over the Power Transceiver. (Additional error coding is disabled during this operation so the code image may be checked after load).

Data to the Microstimulator may be encoded to withstand single, double and burst errors. The error rate signal may be available for use by the PID controller. The controller may also include a Power Transceiver that provides charging power to the Microstimulator in a predetermined frequency range. The frequency and tuning of the Transceiver are typically controlled through a proportional integral derivative (PID) control loop feedback. The Power Transceiver may have a Coupling Strength signal that indicates the coupling coefficient between the Microstimulator and the Patient Charger. The Collector Voltage on the Power Transceiver may be set through the Boost Converter. The boost converter may be controlled by the CPU and may produce volts and amps and may have a predetermined startup time (Z). The temperature of the coil may be monitored and may be shut down if the temperature increases more than 2 degrees centigrade over ambient.

In some variations, the loop (Charger Coil) of the charger may have an average closed diameter of approximately 16±1 cm. In variations in which the loop is expanded to fit over the patient's head, the average open diameter may be approximately 23±2 cm. The loop may be made of any appropriate material for transmitting power to the implant (e.g., by induction). For example, in some variations, the loop comprises turns of gauge-stranded wire with mil thick insulation. A shroud may cover the wire bundle.

As mentioned, the battery in the charger may be a rechargeable lithium ION battery, which may provide enough power for 1 hour of Microstimulator charging between charges of the charger itself. The LION battery may be protected by a thermal switch, and the LION battery may be disconnected when the voltage drops below TBD volts. The LION battery may be charged through a 5V power plug and may charge within 2 hours. The primary internal power supply fed from the LION battery may be 3.3V.

In some variations the charger also includes a display or output. For example, an LCD screen may provide information to the user on a 96×96 bit graphic monochrome screen. One or more inputs or controls may also be included. For example, four buttons may allow the patient the ability to set Patient Charger functions. A Charge button may allow the user to move the Patient Charger back and forth between Stand-by and Microstimulator charging and the charger may show the status of Microstimulator battery charging. A color-indicator may indicate charge status by color coding (e.g., Blue, Green, Yellow or Red). In some variations a speaker may provide audio cues and have 5 volume levels. In addition, an optical or mechanical switch may indicate that the handle is open or closed in relevant variations of the charger.

Figure 34A:
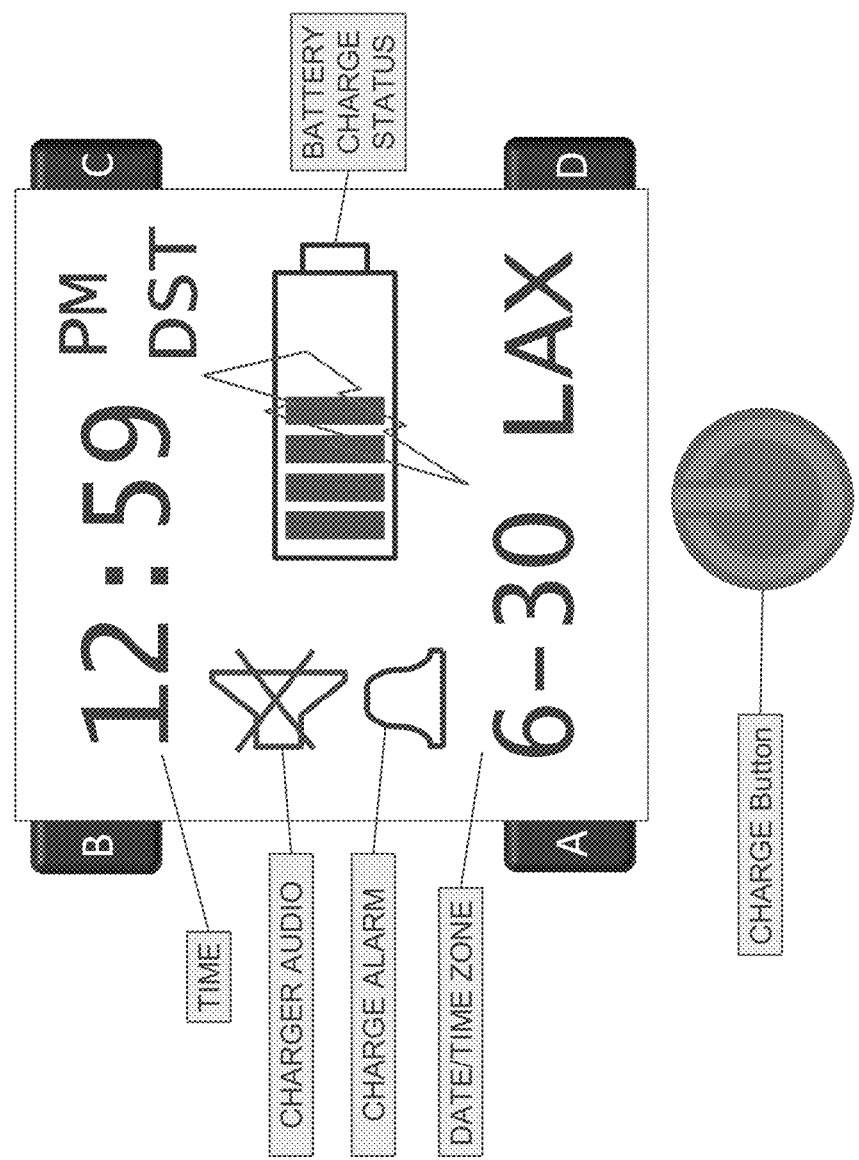
FIGS. 34A-34F illustrate different charger displays that may be used.

For example, FIGS. 34A-34D illustrate various exemplary display screens that may be used with the chargers described herein. For example, in FIG. 34A, the display screen (e.g., an LCD screen) provides information to assist the patient and clinician in maintenance and programming of an implanted microstimulator. In FIG. 34A, the setup buttons A-D are shown alongside the screen and the Charge button is shown below the screen.

The charger may indicate the mode or status (e.g., "DOCK Mode" when the charger is in the dock or plugged into an AC Adapter, etc.). The charger may display the time (in 12 or 24 hour mode) and indicate that day light savings time is set (DST). The date shows the month and day, the year is only shown during setup, and it may also indicate the time zone with a representative city. The Charger battery status indicates the charge status of the Patient Charger. A symbol (such as a lightning bolt) may indicate whether the battery is charging and only may occur when the Charger Mode is in DOCK and the AC Adapter is connected. Charger audio typically indicates the level of acoustic feedback given to the user. In FIG. 34A it is shown muted, but different loudness levels are represented by 4 different speaker sizes. A charge alarm may be set as a reminder to the patient to charge there system from the Prescription Pad.

Figure 34B:
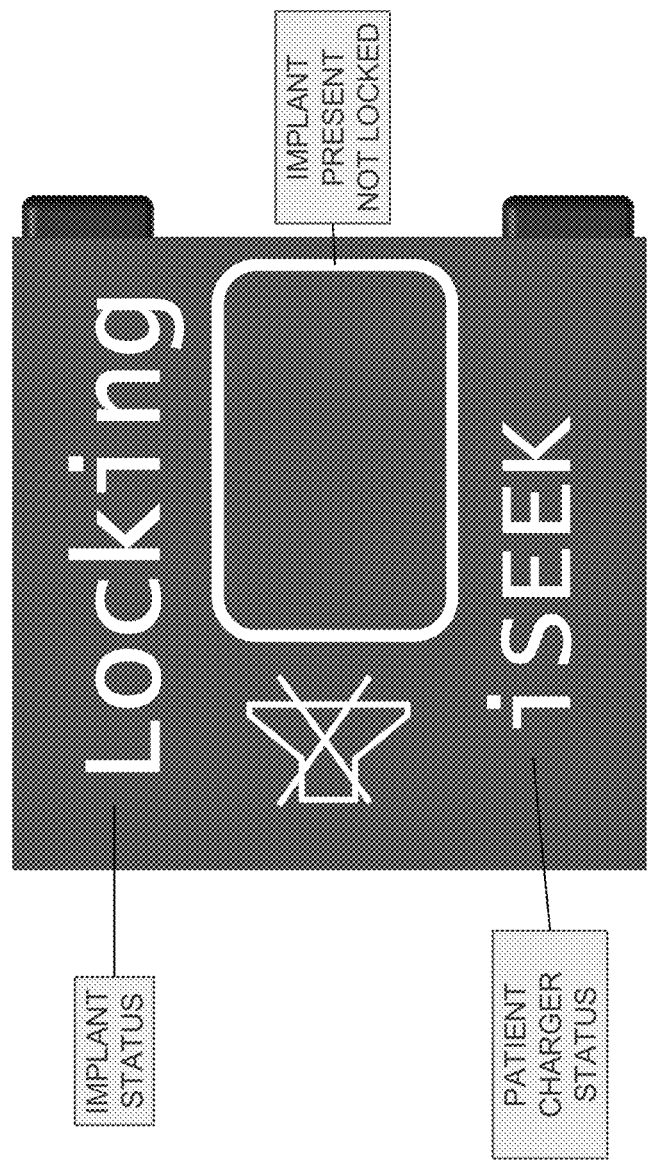

When the charger is in the iSEEK mode (e.g., when the Patient Charger is around the neck and ready to charge, e.g., with the handle closed, and/or when the CHARGE Button has been pressed), the display may be similar to that shown in FIG. 34B. In this example, the screen color is inverted to indicate a Microstimulator Operation, the Patient Charger status is displayed (iSEEK), the implant present symbol (shown as an outline of an implant) and the 'Locking' implant status is shown when the coil has detected the presence of the Microstimulator but has not started charging.

Figure 34C:
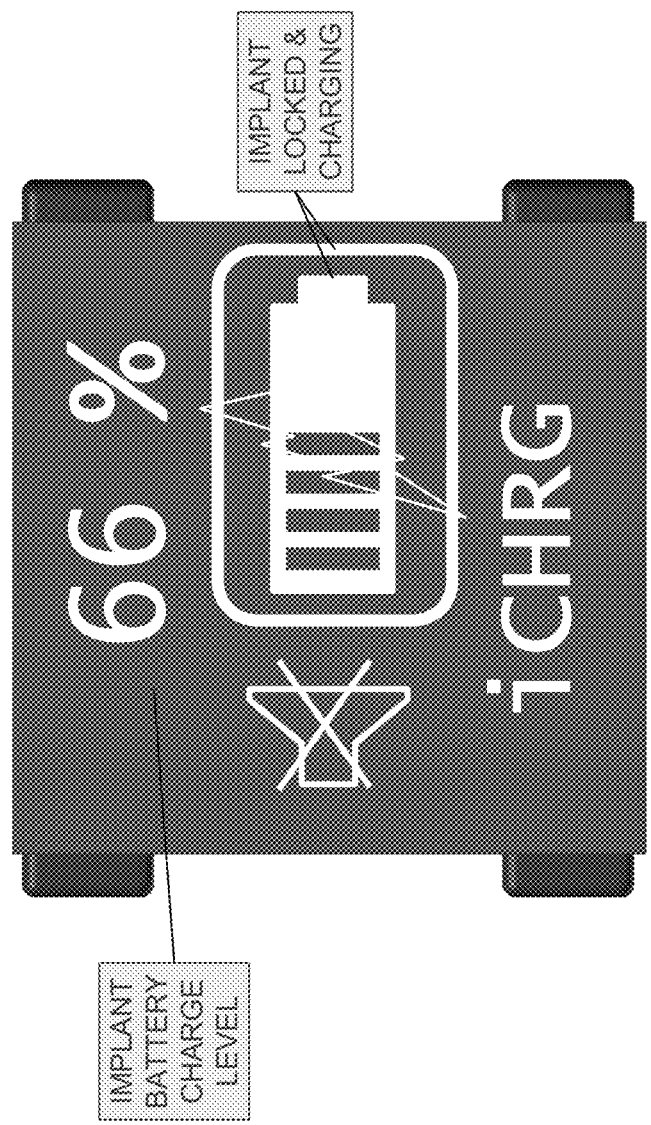

FIG. 34C shows an example of a display on the charger when the device is in the iCHRG mode (when the Microstimulator starts charging). In this example, the Battery Charging symbol may appear inside the Implant symbol. The Implant Battery Status is shown with both a numeric and a graphical display of battery charge level. The numeric charge level may go over 100% when topping off the battery. The charging symbol (e.g., lightning bolt) appears when the device is charging and is synchronized to the Charger button LED. As mentioned, the Implant Battery Level indicates the implant battery level. 75% charge is considered a full charge, so the charging indicator may stay energized for 60 seconds after a full charge is indicated.

Figure 34E:
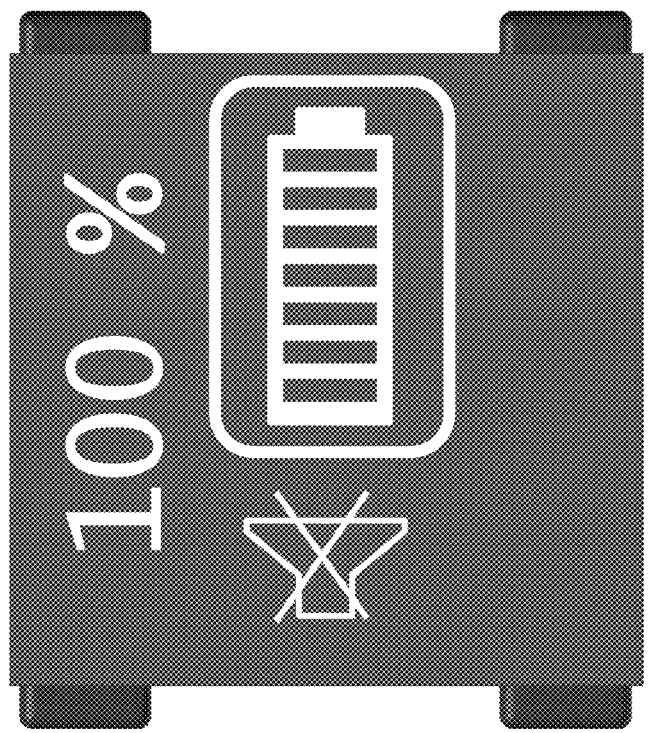
Figure 34D:
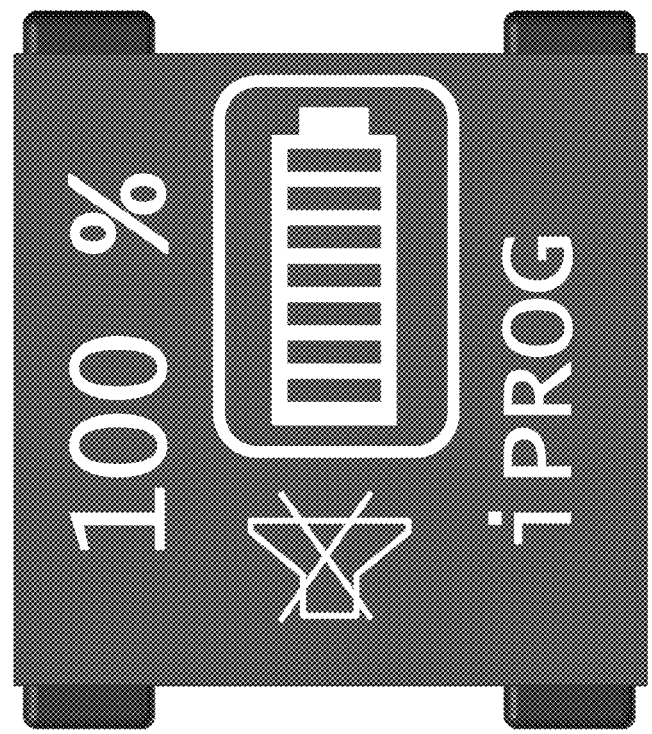
Figure 34F:
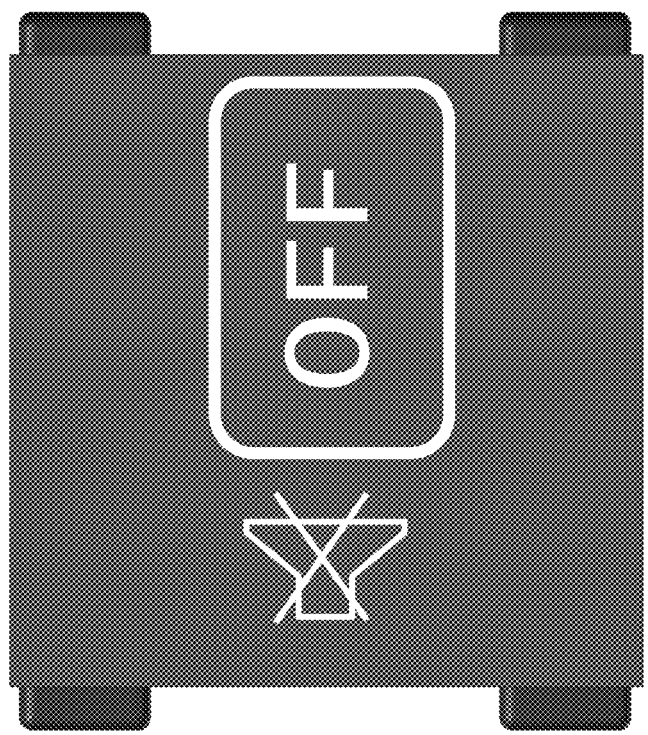

FIG. 34D is an example of a display from the charger when it is in the iPROG mode when an external controller (e.g., a Prescription Pad) is communicating control instructions to the implant through the Patient Charge. The state of the battery is independent of iPROG. FIG. 34E illustrates one example of a display screen when the charger is in a Standby mode (e.g., after charging and programming is complete). An emergency shutoff display is shown in FIG. 34F. In some variations, the microstimulator can be turned off by pressing all 4 buttons simultaneously for 30 seconds; the patient may also be asked to push a sequence of buttons to verify that the patient wants to turn the device off. Once the implant is turned off it can only be turned back on by the Clinician. The charger may display when the implant is in an off state, as illustrated in FIG. 34F.

The charger may receive information from the implant and/or from an external controller (e.g., prescription pad). The charger may pass along instructions to and collect data from the microstimulator. For example, software of firmware may be downloaded into the Microstimulator from the charger when commanded from the Prescription Pad, and data may be uploaded from the Microstimulator when commanded from the Prescription Pad. In some variations, the charger may be updated or restored by the Prescription Pad when the Charger is put into a "boot" mode.

The charger may generally include a microcontroller having a CPU, clock, RAM, EPROM, ADC (receiving/regulating battery voltage, ambient temperature, coil temperatures, and transmitter coupling strength). The microcontroller may also boost supply control signals and stepper motor control signals.

Figure 35A:
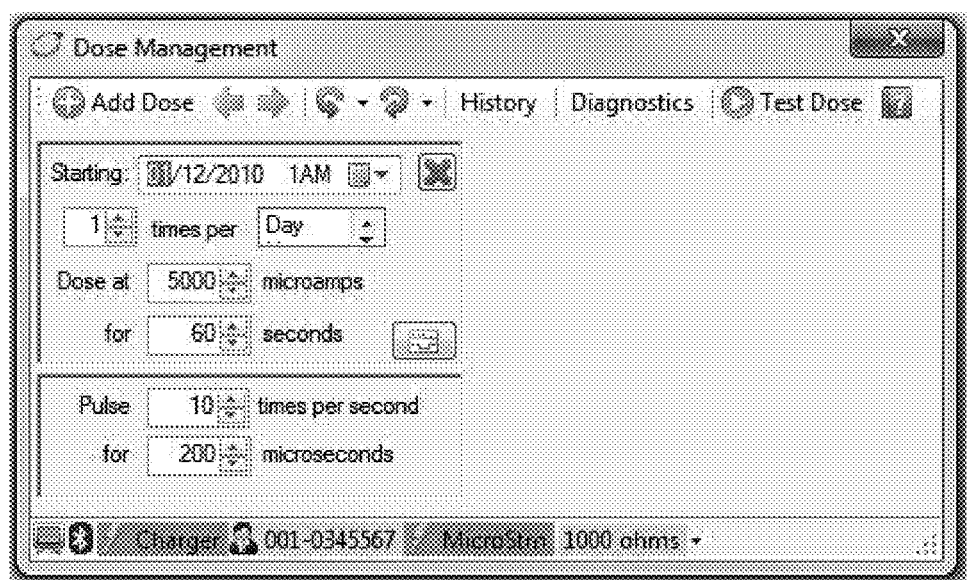
FIG. 35A shows an exemplary control screen for controlling dosage of the system described.

In general the charger may interface with an external controller such as a prescription pad. The prescription pad may include software, hardware and/or firmware for controlling the operation of the implant and/or charger. The charger may serve to relay instructions (and receive data) to and from the microcontroller implant and the controller. For example, a controller may regulate the dosing from the implant. FIG. 35A shows one variation of a dosing management control screen that may be used to set the dosage level (and interval) for the microstimulator implant. Although the variations described herein typically use a separate external controller, in some variations the external controller and the charger may be integrated together into a single device.

In FIG. 35A, the control screen shows a tool bar that allows for an increased/decreased dose to be selected, and allows for more than one (e.g., four) sequential doses to be added. The screen also includes Back and Forward buttons to allow toggling between different doses. The active dose is highlighted and selected when the screen comes up. When multiple doses are displayed the dose may be selected by clicking or using the back and forward selector arrows. A Test Dose control may also be included, which may allow stimulation with the selected dose for 1, 5 or 60 seconds with the selected program. A key (e.g., space bar) can immediately stop the stimulation. The Stimulate button turns green if stimulation is successfully, yellow if current sources are out of compliance, or red if stimulation cannot be delivered. The Impedance value is updated when Stimulate is pressed. Various icons may also indicate the status of one or more components (including the microstimulator and charger). For example, a charger icon may indicate that the charger is connected and operating with sufficient battery charger. If the battery is to low an icon may indicate the condition, and it may not be usable. Text may be shown, as well as a colored bar indicating the state of the battery (<10% is red, <25% is yellow, otherwise it is green). A person icon may indicate that a Microstimulator was found and identified on the patient, and in some variations may display the serial number of the implant. If a microstimulator is not found the person icon is grey, and if an issue is identified with the microprocessor an error icon may be shown The electrode impedance of the microstimulator may also be displayed. For example, the electrode impedance shown may be the last impedance taken, and it may be updated when a connection is established to the microstimulator or before a test stimulation. This value it can be manually refreshed. The screen may also show the current level (A) in microamperes and typically ranges from 0 to 5000 in 25 uA increments. The timing (S) in seconds typically indicates the duration the stimulus may be on during each dosage ranging from 1 to 1000 seconds (e.g., default: 60). The (Pulse) icon allows the pulse waveform to be customized. Pulse (F) times per second sets the frequency of the pulse train between 1 and 50 Hz (default: 10 Hz). The pulse width (PW) in microseconds is the pulse width generated in microseconds and ranges from 50-1000 uS (default: 200 uS) in 50 uS intervals. In general, values may be entered and then tested with the Stimulate button. The Stimulate button turns green if stimulation is successful, turns yellow if current sources are out of compliance, and turns red if stimulation cannot be delivered. The Impedance value is updated when Stimulate is pressed.

In some variations the system stores the patient history, which may include a listing of all doses executed, and the impedances at the start of a Dosing program (only the first dose of a program). The list can be saved or appended to an existing file that is stored under the Microstimulator Serial Number. When appending a file, duplicates may be eliminated. This history may be kept internally, or it may be transferred for analysis or storage. For example, a history file can be transferred to a server for recoding in a patient's medical records.

Figure 35B:
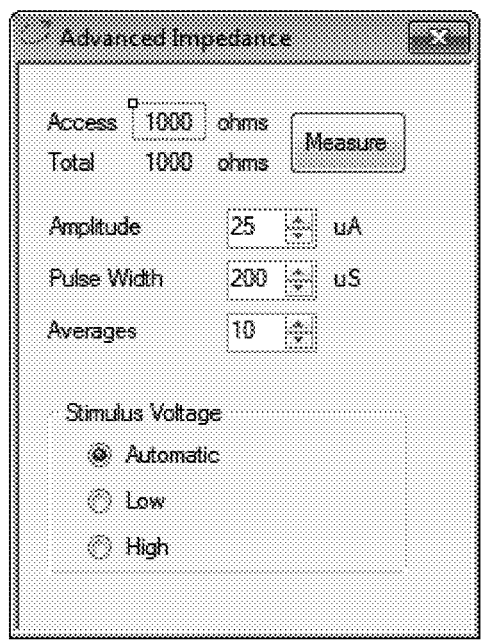
FIG. 35B shows an exemplary advanced impedance control screen.

Additional (e.g., "advanced") parameters may also be regulated or controlled. For example, an advanced Impedance Screen may allow a clinician to modify impedance parameters to debug electrode problems. For example, FIG. 35B shows a control screen for setting advanced parameters. In this example, the access impedance is measured at the leading edge of the pulse, the total impedance is measured and the end of the positive pulse. Amplitude can be adjusted in 25 uA steps. In this example, the pulsewidth can be modified in 50 uS steps. The number of averages can be set to reduce measurement noise in increments of 1.

The systems described herein may also include diagnostics for diagnosing problems with one or more components.

Figure 35C:
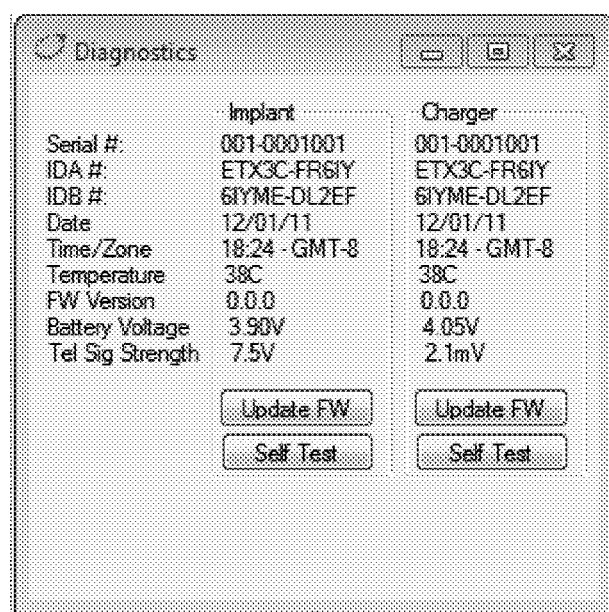
FIG. 35C shows an exemplary diagnostic screen.
Figure 36B:
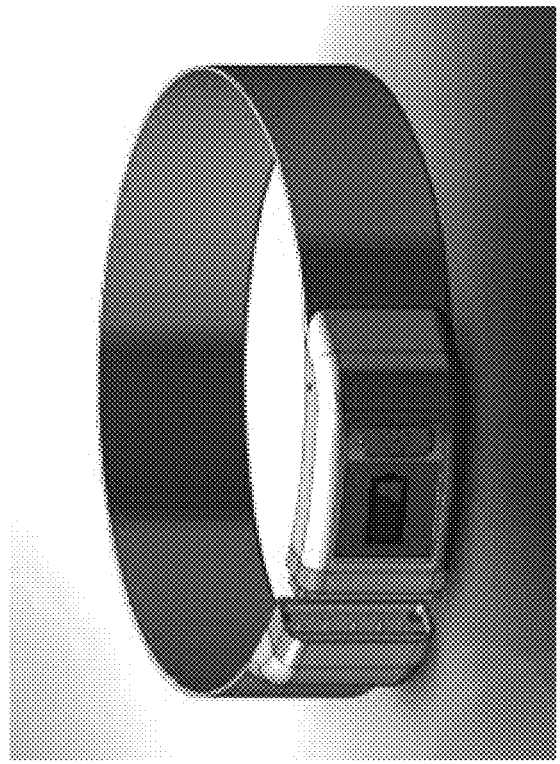
FIGS. 36A and 36B illustrate one variation of a charger for charging and controlling a microstimulator implant.
Figure 36A:
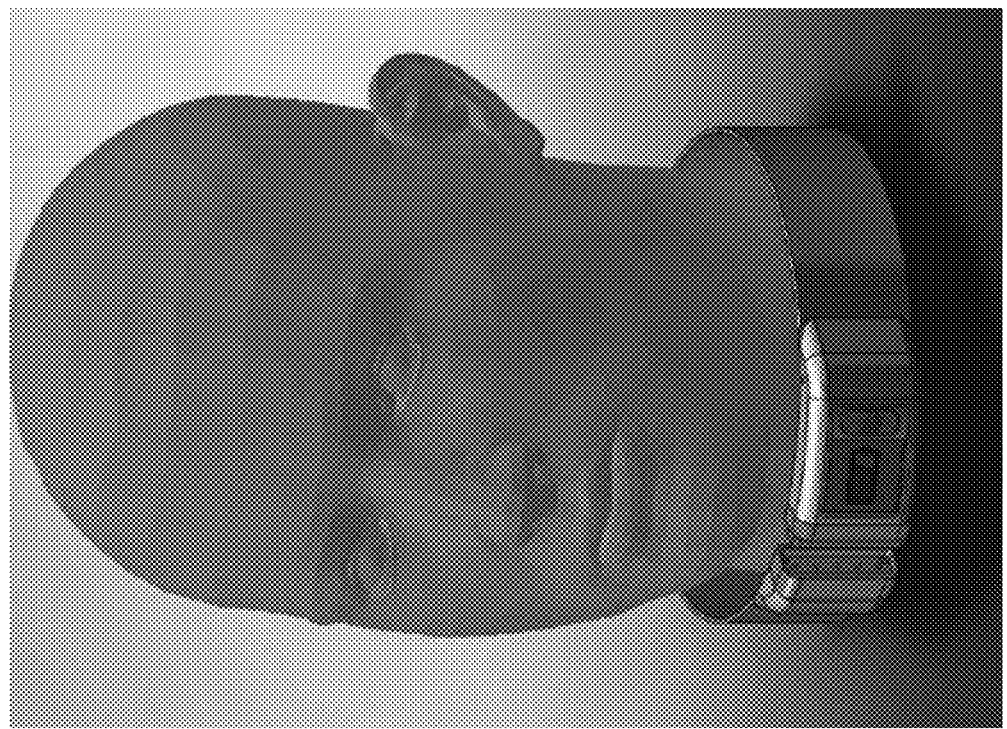

For example, the system (e.g., external controller) may display a diagnostics screen that shows key parameters and allows Self Test and Firmware updates. FIG. 35C illustrates one example of a diagnostics screen. In this example, the screen displays the serial number of both the Charger and Implant presented (if none are present the clinician may be asked for the information). The screen also shows an IDA and IDB number (electronic readable IDs), date and time information, temperature information (e.g., the temperature of Charger Coil and Implant Microprocessor), list firmware/ software versions, indicate the battery voltage from both units, indicate the received telemetry signal strength from both units, and execute a self test from both units (and display the results of the self-test).

Example 2: Charger

One variation of a charger (referred to herein as an "energizer") is described in FIGS. 36-43. In this example, the energizer for powering and programming the microstimulator attaches around the patient's neck like a necklace or collar. FIG. 36A shows one variation of the energizer around the subject's neck. In this example, about an average of 20 seconds of charging will be required per day for NCAP treatment using an implant as described above, and it is recommended that the patient charges at least every week (e.g., for approximately 20*7=3 minutes), even though it is possible not to charge for up to a month requiring a 20-30 minutes to charge.

In this example, the Energizer consists of 4 components: Coil and Magnetic Coil Connector Assembly, Electronic Module, Battery Module, and Acoustic Module.

Figure 37:
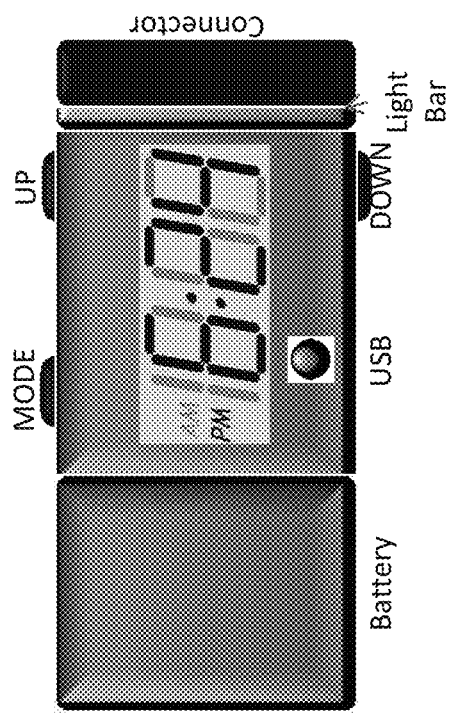
FIG. 37 shows one variation of a coil and magnetic connector assembly.

FIG. 37 shows one variation of a coil and magnetic connector assembly. In this example, the Coil is 13 Turns of a bundle of 26 gauge magnet wire (N conductors) spaced at 100 mils. The connector uses spring load connectors, 2 per connection (20 milliohms per connection) and gold landings resulting in 130 milliohms. The Inductance is around 40 uH and Q is over 200. The battery module in this example is a 650 mA/hr Li-Polymer battery with a built in temperature sensor. It is attached to the coil assembly and connects to the Electronic Module with 3 flexible wires. The charge and discharge rate is 1 C. The charge rate may be slower than one hour depending due to thermal protection. The battery back is packages in a plastic container that is 5.8 mm×42 mm×34 mm.

An acoustic module may include a 16 D×2.5 mm speaker that can generate 82 dB SPL above 500 Hz.

In operation, an Energizer creates a magnetic field of approximately 47-94 A/m (0.6-1.2 Oe) at a frequency between 127-135 KHz. This low frequency range was chosen for several reasons: 1) it is acceptable to radiate in the range in most countries around the world, 2) staying with radiated limits biologic limits is possible, 3) absorption by the human body is minimal and field penetrates with minimal attenuation, 4) conductive materials block the field has less of an effect, 5) high efficiency electrical circuits are easily achieved at lower frequencies. The primary disadvantage of lower frequencies is that a higher inductance resonator coil is required in the body.

The magnetic field may be generated by clocking the transmitter at the carrier frequency (CF) at the system resonant frequency. The collector voltage (CV) may be set to provide sufficient power to energize Microstimulator coil to charge battery and power MCU, but it does not necessarily directly indicate voltage induced in implant. The CV may also be set to allow various positions on neck and movement, and to compensate for energy loss due to Forward and Backwards telemetry. Finally, the CV may be set so that it does not overpower and cause excessive Microstimulator heating.

At least two charging coil schemas may be used: a solenoid and a pancake coil. A solenoid was chosen due to the required implant depth of normally around 2-5 cm. A solenoid generates a fairly uniform field and makes positioning of the coil unimportant. A pancake coil would require precise positioning and excessive power to reach coil to coil spacing in excess of 2 cm. The challenge with the solenoid was to find a system that would be comfortable for the patient. That was achieved by using a magnetic spring loaded connector, and the system is further aided by the fact that charging times are very short, never more than 20 minutes, but usually less than 1 minute.

Figure 38:
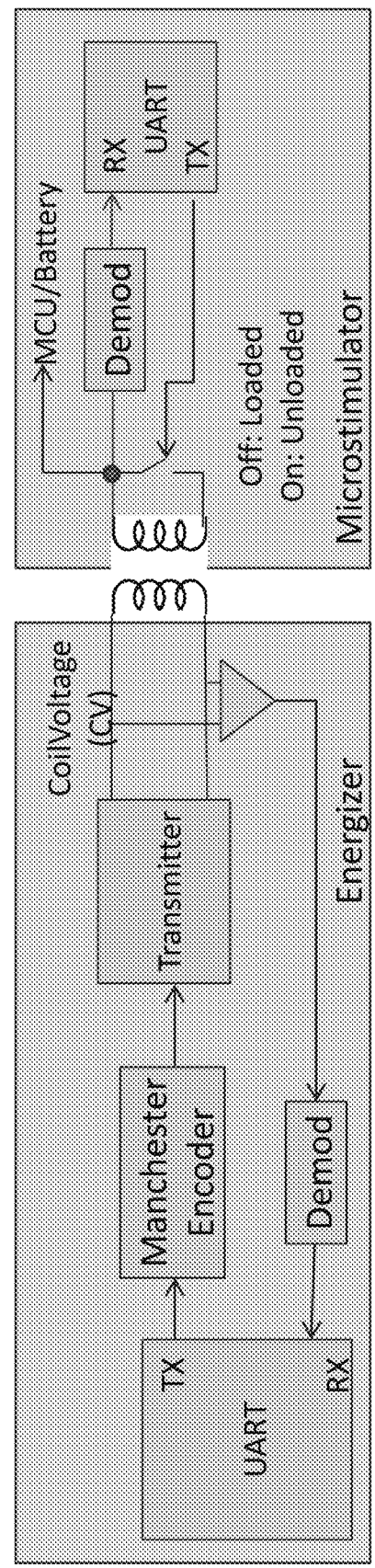
FIG. 38 is a schematic of the transmission of power between the charger and a microstimulator.

The Energizer and Microstimulator coils may be tuned to resonate so that energy is transferred with the maximum efficiency from the Energizer to Microstimulator. The Microstimulator in turn harvests the energy from the Energizer created magnetic field to power itself. The power harvested is less than 15 mW. FIG. 38 shows a schematic diagram of the transfer of power between an energizer and a microstimulator Tuning, or maximizing the mutual inductance between the two coils may be performed by using resonators that are physically adjusted to approximately 133 KHz±4 KHz. Fine tune adjustments may be made dynamically by varying the Energizer frequency with the allocated 127-135 KHz frequency band. Another method to be employed for electronic tuning that may be used induces a static flux in series inductor in the Energizer coil to electronically modify the inductance (see, e.g., U.S. Pat. No. 3,631,534).

Energy transfer is controlled by throttling the magnetic field. The magnetic field is typically created by a high efficiency Class-D amplifier. The induced coil voltage on the resonator is controlled by the collector voltage driving the amplifier. It is important to only provide sufficient power to the implant as not to saturate the Microstimulator circuits or overheat the Microstimulator, a condition which can easily be achieved. Energy transfer varies significantly with vertical position so feedback is required. Feedback is obtained through two mechanisms, the most obvious being to query the Microstimulator telemeter incoming energy level, a much less obvious method that measures the difference in Energizer coil voltage between the presence and absence of the Microstimulator. With that measure the energy being absorbed by the Microstimulator can be calculated with sufficient accuracy to control the Energizer collector voltage.

The telemetry system in this example is implemented that two standard microprocessor UARTs communication with a RS-232 type half duplex protocol where the Energizer is the master. Two rates 1200 and 4800 baud may be implemented. Forward telemetry modulates the transmitter collector voltage to send data across. To keep the Microstimulator demodulator as simple as possible a DC balanced Manchester code may be employed with a simple zero crossing data slicer. The RS-232 code itself does not need to be DC balanced, but the presence of start and stop bits are sufficient to allow sufficient energy transfer during communications.

The Microstimulator resonated may be put into one of two states with a shorting switch. When the switch is open the Microstimulator is operating normally, receiving power and telemetry, and is loading the Energizer. When the Microstimulator switch is closed the coil is not longer tuned to the Energizer coil and the Microstimulator ceases to receive power, and the load that the Microstimulator normally asserts on the Energizer is removed. This switch provides several functions: it may be used to send back telemetry data to the Energizer, used by the Energizer to measure the power absorption by the Microstimulator, and/or used by the Microstimulator to turn off power absorption in case the Microstimulator becomes too hot or the internal voltage becomes too high.

The Microstimulator may respond to all packets by toggling the load switch with the UART. Data is sent in NRZ format (e.g., back telemetry). The Energizer may measure the coil voltage, removing the ≈130 KHz carrier and extracting the resulting data stream that is effectively the peak coil voltage updated at a rate of 20 KHz. The Energizer converts this analog voltage into a digital word and slices the data to produce bits that are fed to the UART. This is done in the digital domain because a sophisticated min/max peak detector can be implemented that does not require DC balanced data and can respond within 1-2 symbols.

Power is adjusted by achieving a target modulation depth on received back telemetry data. The target modulation depth is determined by calibrating the system through measurements of power transfer to the Microstimulator. It is unknown at this point when calibration will occur: once for all systems, once for each system, on power up of each system, continuously as the Energizer coil moves around.

Recall that an electronic module with the battery module is shown in FIG. 37. The electronic module in this example is 1.5 tall by 1.8 wide and connects to the coil. It is attached to the coil with two flexible wires.

The module may have a custom LCD for displaying time and alarms. A Mode Switch (SW3) may be used, e.g., in the upper left corner, along with UP and DOWN switches (SW2 & SW1). A MicroUSB port with charging LED (D2) may be in the lower left. A RGB LED may be on the right side just below the LCD and a light guide will route the light to a visible band called the light bar.

As mentioned, the energizer example described may also include a patient charger RF interface module. For example, the energizer may communicate to the Microstimulator through an RF Interface. The RF Interface typically receives serial NRZ data from the MCU UART, converts it to Manchester code that modulates the coil to power and communicate with the Microstimulator. When not transmitting data or idles the RF Interface receives data from the Microstimulator. This data is received in an Analog form and is sent to the MCU ADC where it is sliced and fed into the MCU UART. The MCU is responsible for setting the RF Interface power level and the frequency of operation.

The MCU in this example operates as a master sending packets to the Microstimulator and expecting response within an allocated period. The Packet protocol contains preambles to synchronize communications and error checking to assure that data is reliable. MCU generates serial NRZ transmission to the RF interface and is responsible for: insuring contiguous bits/words in a packet so as not to disrupt the Manchester receiver at either 1200 or 4800 baud; and/or maintaining a high state when not transmitting; maintaining somewhat constant power (e.g. when idling sending alternating data rather than long blocks of idle characters.

The MCU receives filtered analog data that represents the RF carrier level and converts it to digital data for: slicing data when return data is expected, to extract serial NRZ data that is presented to the MCU UART for decoding; monitoring modulation depth of returning data to estimate and optimize the power level sent to the Microstimulator (power is optimized to provide sufficient power to charge battery but not to over-heat Microstimulator); and/or monitoring coil voltage levels to verify expected coil voltages and assure system is operating correctly. The MCU may also program the RF Interface to modulate either carrier modulation or collector voltage modulation or both, and the MCU may adjust the carrier frequency to maximize the mutual coupling between the Energizer and Microstimulator resonators.

Figure 39:
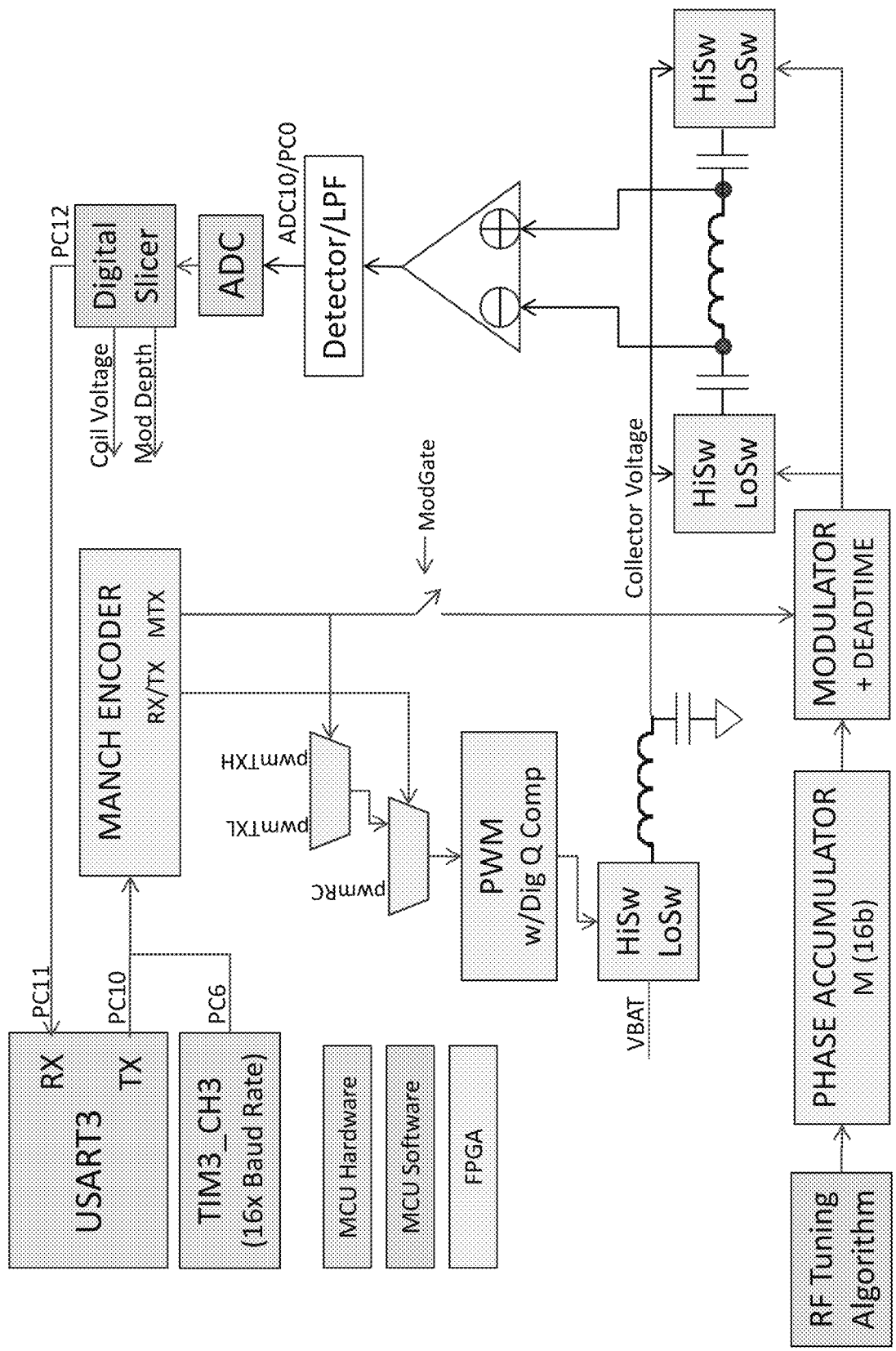
FIG. 39 shows a functional block diagram of the system operation for one variation of a charger.

The RF Interface section consists of functionality implemented by MCU hardware and software, Programmable Logic Device (PLD), and analog circuitry. The functional block diagram is shown in FIG. 39.

In operation, the MCU generates NRZ data from USART3 and from TIM3_CH3 a clock that is within 1% of 16× the baud rate. The Manchester Encoder converts this NRZ data to Manchester data (MTX) resynchronizing to the start bit every word. As soon as start bits enter the Manchester Encoder the (RX/TX) bit goes high and stays high until the last stop bit is sent. The RX/TX bit uses two multiplexers to select either the pwmRC during receive mode and the pwmTXL or pwmTXH during transmit mode to feed to the Pulse Width Modulator (PWM). The PWM uses these values to drive the High and Low switches to generate the collector voltage. When transitioning between these pwm values digital Q compensation smooths the transitions utilizing a digital filter to control the overshoot and undershoot reducing extraneous frequency components.

The RF Tuning Algorithm adjusts Phase Accumulator to generate a carrier frequency with 5 Hz resolution programmed with the 16 bit M register. The RF Tuning Algorithm has not been determined but most likely uses a measure of modulation depth from the Digital Slicer. The Modulator+Deadtime logic drives the High and Low Switches in the H-Bridge configuration to excite the coil. 1/MCO of deadtime is inserted to avoid current waste through simultaneous activation of the High and Low Switches. If the MCU has programmed the GatedMod bit then the MTX bit gates the carrier on and off assuring that switching occurs on the edges.

The voltage is measured across the coil and the carrier is extracted feeding an analog signal to the ADC with a bandwidth of less than 20 KHz. A digital slicer is implemented in software that slices the signal with the short term average of the signal allowing USART synchronization with a minimum number of preamble characters in the response packet. The short term average is determined by minimum and maximum peak detectors that are reset at the symbol rate and smoothed appropriately.

Figure 40:
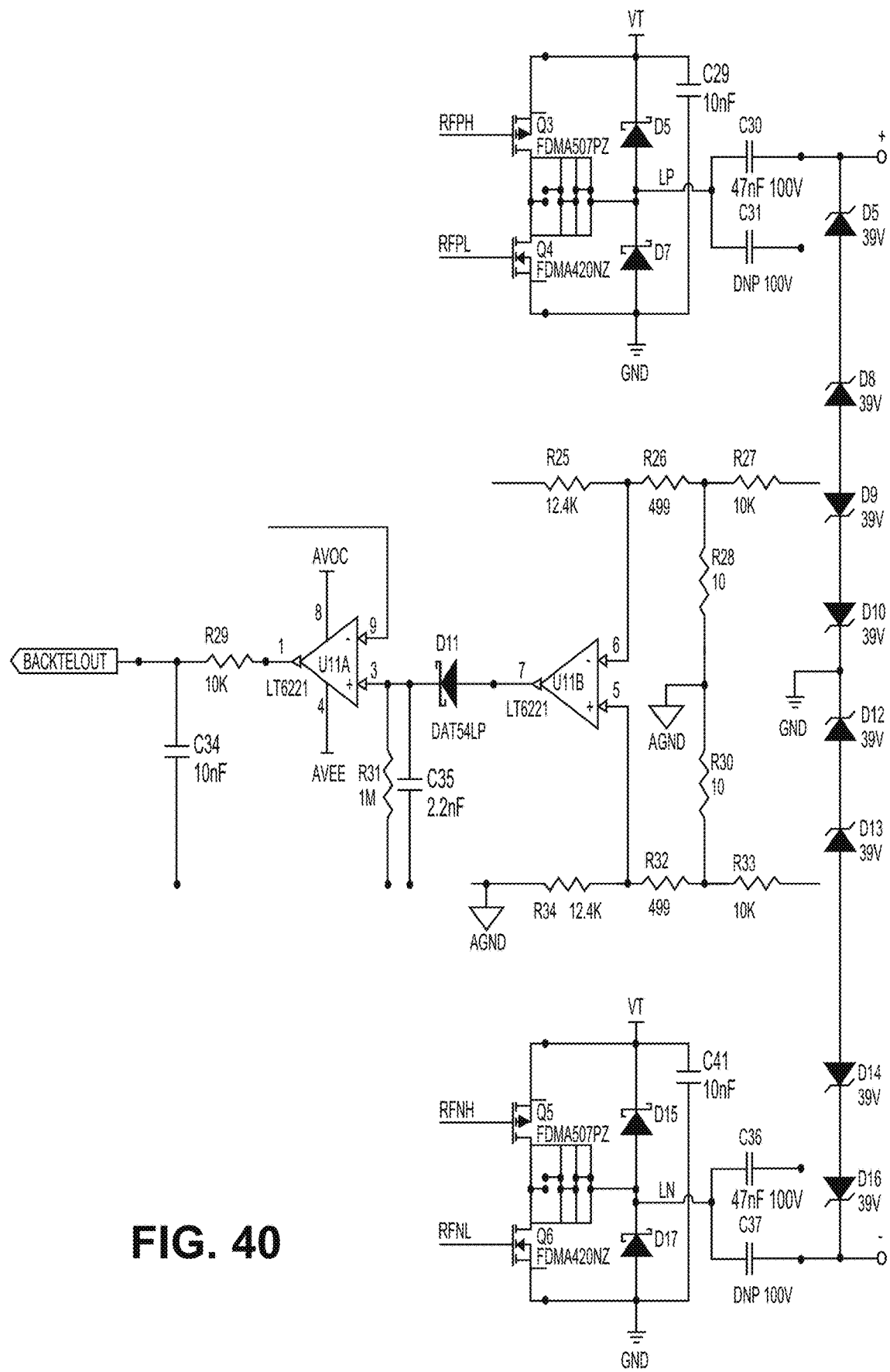
FIG. 40 shows a Class-D amplifier and the back telemetry data detector for use with a charger.

The Class-D amplifier and the back telemetry data detector is shown in FIG. 40. An H-bridge topology is implemented through PMOS (Q3 & Q5) and NMOS switches (Q4 & Q5). These switches are driven by a PLD implementing the logic described earlier. The coil is connected through two series capacitors C30 and C36 surrounding a coil. Zener diodes prevent the coil voltage from exceeding +/−80 volts. VT is the so-called Collector Voltage and 1V generates around +/−50V on the coil.

VT is generated using a PWM converter shown in the following diagram in a very efficient manner. The PMOS and NMOS switches are driven by the PLD and VT is modulated with data. The carrier frequency for this circuit is 500 KHz about 4× higher than the RF carrier frequency. Referring to FIG. 40, the data detector is implemented by measuring the voltage across the coil with a difference amplifier implemented by U11B. The LT6621 has a 50 MHz GBW product which is able to track coil modulation on the 135 KHz carrier with little loss of fidelity. The voltage is divided by 1000× to scale the +/−80V range to the +/−3.3 volt range of the system. After the voltage difference is obtained D11 & C53 rectifies the waveform and U11A implements a 2 pole 20 KHz low pass filter prior to ADC conversion. Due to the very high Q of the coil the actual frequency content of the signal is much less than 20 KHz permitting slower ADC conversion rates.

As mentioned briefly above, the energizer user interface typically consists of a Clock LCD display, Up, Down and Select Keys for setting the time, Alarms, and Emergency Microstimulator off. In some variations the display includes a multicolor LED indicating the state of charge of the Microstimulator. The LED may indicate that the Energizer is plugged into a USB power adapter or port and is charging. A speaker may be included to provide charging cues to the patient.

For example, the charger may include an MCU LCD controller that is used to control the time display.

As mentioned, the power system for the energizer (charger) may include an MCU. The MCU is typically always powered, even when the battery drops below 2.5V. Peripherals are enabled through VCCEN. The target operation of the circuitry is 3.3 Volts. It is the responsibility of the MCU to not let the battery drop below 3.4 volts. When the RF Interface is operating it can require up to 500 mA. This will limit the battery capacity to around 90% of what would be possible with a lower operating voltage.

Battery charging may occur through a MicroUSB port. The input is designed to be operated at 5V but can tolerate 30V. Charging will occur when the port is between 4.5-6.4 volts. An AC adaptor or USB cable to a USB device can be used for charging. If hardware detects a USB source charge will be limited to 100 mA not to pull down the USB device, otherwise charging can occur at full rate. There multiple temperature controls to avoid skin exposed surfaces from exceeding 41° C. while operating at 25° C. Table 8 describes some of the temperature monitors that may be included as part of the system.

TABLE 8

| Monitor | Function | Limitations |
| --- | --- | --- |
| Battery Thermistor | Protects battery from damage by limiting charge rate per JEITA standards. | |
| Charger Junction Temperature Sensor | Protects circuits from damage by limiting charge rate. | |
| External Charger Temperature Sensor | Software periodically senses to limit charge rate when possible skin temperature reaches 41° C. Since MCU does not control charging temperature is always monitored. Software controls fast charging through BATSET. | Will not completely stop charging. If charger is left in hot location for charging it will still charge at a slow rate. The device can be in an environment where even slow charging can cause the temperatures to rise beyond desired levels. Even though the system will not power it is the responsibility of the user to check the device temperature before application. |

TABLE 8-continued

| Monitor | Function | Limitations |
| --- | --- | --- |
| System Level Temperature Sensor inside MCU | Software will monitor both the External Charger Temperature and MCU temperature to assure that temperatures are within range before Microstimulator operations are enabled. | The device itself can be left in the sun, be applied, and cause burns even without being powered. It is the responsibility of the user to check the device temperature before application. |

In Table 8, BATSET=Float allows the charger to charge at fast rate if all conditions are met, BATET=Low forces the charger to charge at slow rate; and BATSET=High allows charge to charge at fast rate if all conditions are met.

While the methods, devices and systems for treating chronic inflammation by modulating the inflammatory reflex have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention. In particular, the methods and systems described herein may be used in conjunction with other chronic inflammation treatments and systems, including pharmaceutical treatments.

What is claimed is:

1. A leadless, implantable microstimulator device, the device comprising:
   a hermetically sealed capsule body;
   an electrode saddle on a first side of the capsule body, wherein the electrode saddle comprises an electrode saddle body having a first concave region and a second concave region, wherein the first concave region is separated along the length of the hermetically sealed capsule body by a non-concave gap region from the second concave region, wherein a first electrode is molded into the first concave region and a second electrode is molded into the second concave region; and
   an electronic assembly within the sealed capsule body;
   wherein the electronic assembly comprises a microcontroller configured to control the application of electrical energy to a nerve held against the electrode saddle by applying energy between the first electrode and the second electrode.

2. The device of claim 1, wherein the capsule body comprises a tubular body.

3. The device of claim 1, wherein the capsule body comprises a Zirconia tube.

4. The device of claim 1, wherein the first electrode is integrated into the first concave region and the second electrode is integrated into the second concave region.

5. The device of claim 1, wherein the electrode saddle body is integrally formed with the capsule body.

6. The device of claim 1, wherein the electrode saddle body is attached to the outside of the capsule body.

7. The device of claim 1, wherein the surface area of the first electrode and the second electrode configured to electrically contact the nerve is greater than 15 mm$^2$.

8. The device of claim 1, wherein the microcontroller is configured to apply a dose of up to 5 mA.

9. The device of claim 1, wherein the total volume of the device is less than 1.5 cubic centimeters (cc).

10. A leadless, implantable microstimulator device, the device comprising:
- a hermetically sealed cylindrical capsule body;
- an electrode saddle extending from a first side of the capsule body and configured to partially enclose a nerve, wherein the electrode saddle comprises an electrode saddle body, wherein the electrode saddle body comprises a first concave region and a second concave region, wherein the first concave region is separated along the length of the hermetically sealed cylindrical capsule body by a non-concave gap region from the second concave region, wherein a first electrode is molded into the first concave region and a second electrode is molded into the second concave region; and
- an electronic assembly within the sealed capsule body in electrical contact with the first and second electrodes;
- wherein the electronic assembly comprises a microcontroller configured to control the application of electrical energy to a nerve held against the electrode saddle by applying energy between the first electrode and the second electrode.

11. The device of claim 10, wherein the capsule body comprises a tubular body.

12. The device of claim 10, wherein the capsule body comprises a Zirconia tube.

13. The device of claim 10, wherein the first electrode is integrated into the first concave region and the second electrode is integrated into the second concave region.

14. The device of claim 10, wherein the electrode saddle body is integrally formed with the capsule body.

15. The device of claim 10, wherein the electrode saddle body is attached to the outside of the capsule body.

16. The device of claim 10, wherein the surface area of the first electrode and the second electrode configured to electrically contact the nerve is greater than 15 mm$^2$.

17. The device of claim 10, wherein the microcontroller is configured to apply a dose of up to 5 mA.

18. The device of claim 10, wherein the total volume of the device is less than 1.5 cubic centimeters (cc).

19. The device of claim 1, wherein each of the first concave region and the second concave region are configured to at least partially surround the nerve.

20. The device of claim 1, wherein the electrode saddle body comprises a polymer material.

21. The device of claim 10, wherein each of the first concave region and the second concave region are configured to at least partially surround the nerve.

22. The device of claim 10, wherein the electrode saddle body comprises a polymer material.

* * * * *